US011160972B2

(12) United States Patent
Freeman et al.

(10) Patent No.: US 11,160,972 B2
(45) Date of Patent: Nov. 2, 2021

(54) GARMENTS FOR WEARABLE CARDIAC MONITORING AND TREATMENT DEVICES

(71) Applicant: ZOLL Medical Corporation, Chelmsford, MA (US)

(72) Inventors: Gary A Freeman, Waltham, MA (US); James A Patterson, III, Claridge, PA (US); Christopher L Swenglish, Connellsville, PA (US); Jason T Whiting, Gibsonia, PA (US)

(73) Assignee: ZOLL Medical Corporation, Chelmsford, MA (US)

( * ) Notice: Subject to any disclaimer, the term of this patent is extended or adjusted under 35 U.S.C. 154(b) by 186 days.

(21) Appl. No.: 16/369,118

(22) Filed: Mar. 29, 2019

(65) Prior Publication Data

US 2019/0298987 A1 Oct. 3, 2019

Related U.S. Application Data

(60) Provisional application No. 62/650,478, filed on Mar. 30, 2018.

(51) Int. Cl.
*A61N 1/04* (2006.01)
*A61B 5/00* (2006.01)
(Continued)

(52) U.S. Cl.
CPC ............ *A61N 1/0484* (2013.01); *A61B 5/256* (2021.01); *A61B 5/316* (2021.01); *A61B 5/363* (2021.01);
(Continued)

(58) Field of Classification Search
CPC ........ A61N 1/0484; A61N 1/08; A61B 5/256; A61B 5/6804; A61B 5/6805; A61B 5/6823; A61B 5/0245
See application file for complete search history.

(56) References Cited

U.S. PATENT DOCUMENTS

| 4,849,733 A | 7/1989 | Conigliaro et al. |
| 4,928,690 A | 5/1990 | Heilman et al. |

(Continued)

FOREIGN PATENT DOCUMENTS

| DE | 102005060985 | 6/2007 |
| WO | 2015056262 | 4/2015 |

OTHER PUBLICATIONS

Meziane, N., et al., Dry electrodes for electrocardiography, Physiol. Meas. 34 (2013) R47-R69,24 pages.
(Continued)

*Primary Examiner* — Eric D. Bertram
(74) *Attorney, Agent, or Firm* — Zoll Medical Corporation

(57) ABSTRACT

A wearable cardiac monitoring and treatment device includes a garment, a plurality of ECG electrodes and a plurality of therapy electrodes supported by the garment. A fastener is configured to secure the garment about a torso of the patient for a prescribed duration. A disengagement sensor to provides an indication of disengagement of the fastener prior to expiration of the prescribed duration in which the garment is no longer secured about the torso of the patient. The device includes a therapy delivery circuit coupled to the plurality of therapy electrodes and configured to deliver one or more therapeutic pulses. A controller coupled to therapy delivery circuit is configured to analyze an ECG signal monitored by the plurality of ECG electrodes and, upon detecting one or more treatable arrhythmias, cause the therapy delivery circuit to deliver the one or more therapeutic pulses to the patient.

20 Claims, 46 Drawing Sheets

(51) Int. Cl.

| | | |
|---|---|---|
| *A61B 5/316* | (2021.01) | |
| *A61B 5/363* | (2021.01) | |
| *A61B 5/256* | (2021.01) | |
| *A61N 1/08* | (2006.01) | |
| A61B 5/0245 | (2006.01) | |
| A61N 1/39 | (2006.01) | |
| A61B 5/0205 | (2006.01) | |
| A61B 5/25 | (2021.01) | |
| A61B 5/361 | (2021.01) | |

(52) U.S. Cl.
CPC .......... *A61B 5/6804* (2013.01); *A61B 5/6805* (2013.01); *A61B 5/6823* (2013.01); *A61N 1/08* (2013.01); *A61B 5/0006* (2013.01); *A61B 5/0205* (2013.01); *A61B 5/0245* (2013.01); *A61B 5/25* (2021.01); *A61B 5/361* (2021.01); *A61N 1/3925* (2013.01)

(56) References Cited

U.S. PATENT DOCUMENTS

| | | |
|---|---|---|
| 5,078,134 A | 1/1992 | Heilman et al. |
| 5,741,306 A | 4/1998 | Glegyak et al. |
| 5,944,669 A | 8/1999 | Kaib |
| 6,065,154 A | 5/2000 | Hulings et al. |
| 6,215,395 B1 | 4/2001 | Slaughter et al. |
| 6,280,461 B1 | 8/2001 | Glegyak et al. |
| 7,867,056 B2 | 1/2011 | Scheininger et al. |
| 7,912,540 B2 | 3/2011 | Palti |
| 8,099,163 B2 | 1/2012 | Jung et al. |
| 8,167,678 B2 | 5/2012 | Castellano |
| 8,352,012 B2 | 1/2013 | Besio |
| 8,369,944 B2 | 2/2013 | Macho et al. |
| 8,419,502 B2 | 4/2013 | Liu |
| 8,560,044 B2 | 10/2013 | Kurzweil et al. |
| 8,644,925 B2 | 2/2014 | Volpe et al. |
| 8,758,081 B2 | 6/2014 | Yuasa et al. |
| 8,818,478 B2 | 8/2014 | Scheffler et al. |
| 8,825,174 B2 | 9/2014 | Panting |
| 8,840,573 B2 | 9/2014 | Neustaedter et al. |
| 9,007,216 B2 | 4/2015 | Oskin et al. |
| 9,131,901 B2 | 9/2015 | Volpe et al. |
| 9,272,131 B2 | 3/2016 | Kaib |
| 9,402,955 B2 | 8/2016 | Oestreich |
| 9,427,564 B2 | 8/2016 | Kaib et al. |
| 9,462,974 B2 | 10/2016 | Kaib et al. |
| 9,782,578 B2 | 10/2017 | Kaib et al. |
| 2002/0032386 A1* | 3/2002 | Sackner ............... A61B 5/0205 600/536 |
| 2008/0287769 A1 | 11/2008 | Kurzweil et al. |
| 2008/0287770 A1 | 11/2008 | Kurzweil et al. |
| 2012/0062110 A1 | 3/2012 | Rabe et al. |
| 2012/0158074 A1 | 6/2012 | Hall |
| 2015/0217121 A1 | 8/2015 | Subramanian et al. |
| 2016/0045156 A1* | 2/2016 | Kaib ...................... A61B 5/35 600/388 |
| 2016/0256104 A1 | 9/2016 | Romem et al. |
| 2016/0274162 A1* | 9/2016 | Freeman ................. A61N 1/39 |
| 2018/0168508 A1* | 6/2018 | Biel ...................... A61B 5/282 |
| 2019/0192867 A1* | 6/2019 | Savage ............... A61N 1/3904 |
| 2019/0282115 A1* | 9/2019 | Volpe ................... G16H 50/20 |

OTHER PUBLICATIONS

Hoffmann, Klaus-Peter, Flexible dry surface-electrodes for ECG long-term monitoring, Proceedings of the 29th Annual International Conference of the IEEE EMBS, Cite Internationale, Lyon France, Aug. 23-26, 2007, 4 pages.

British Standards Institution, Biological evaluation of medical devices—Part 10: Tests for irritation and delayed-typed hypersensitivity, BS EN ISO 10993-10:2002, Oct. 2002, 62 pages.

Association for the Advancement of Medical Instrumentation, American National Standard, Biological evaluation of medical devices—Part 10: Tests for irritation and skin sensitization, ANSI/AAMI/ISO 10993-10:2010, 88 pages.

Prats-Boluda, G., et al., Active flexible concentric ring electrode for non invasive surface bioelectrical recordings, Measurement Science and Technology. 23(12): 1-10. doi:10.1088/0957-0233/23/12/125703, 18 pages.

Lidón-Roger, José Vicente, et al., Textile Concentric Ring Electrodes for ECG Recording Based on Screen-Printing Technology, Sensors 2018, 18, 300; doi:10.3390/s18010300, 15 pages.

Besio, W. et al., Development of a Tri-polar Concentric Ring Electrode for Acquiring Accurate Laplacian Body Surface Potentials, Annals of Biomedical Engineering, vol. 34, No. 3, Mar. 2006, pp. 426-435, 10 pages.

\* cited by examiner

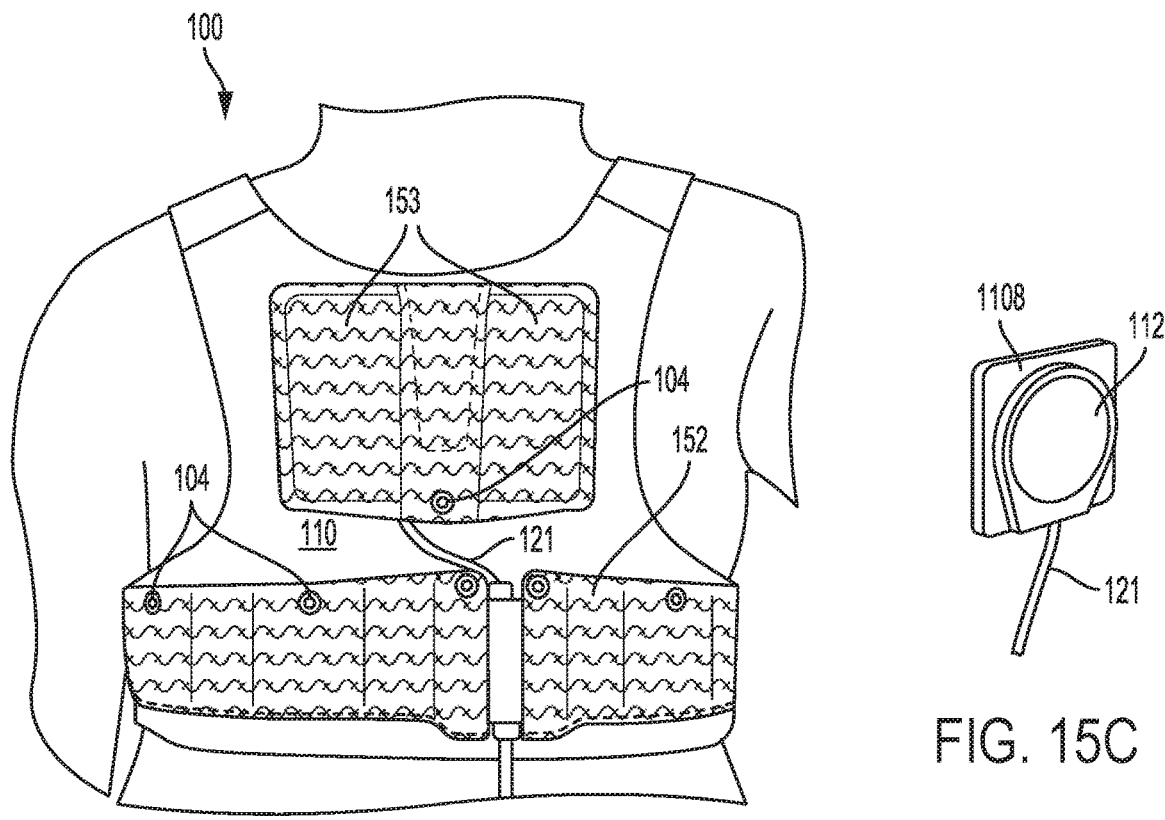
FIG. 15A
FIG. 15C
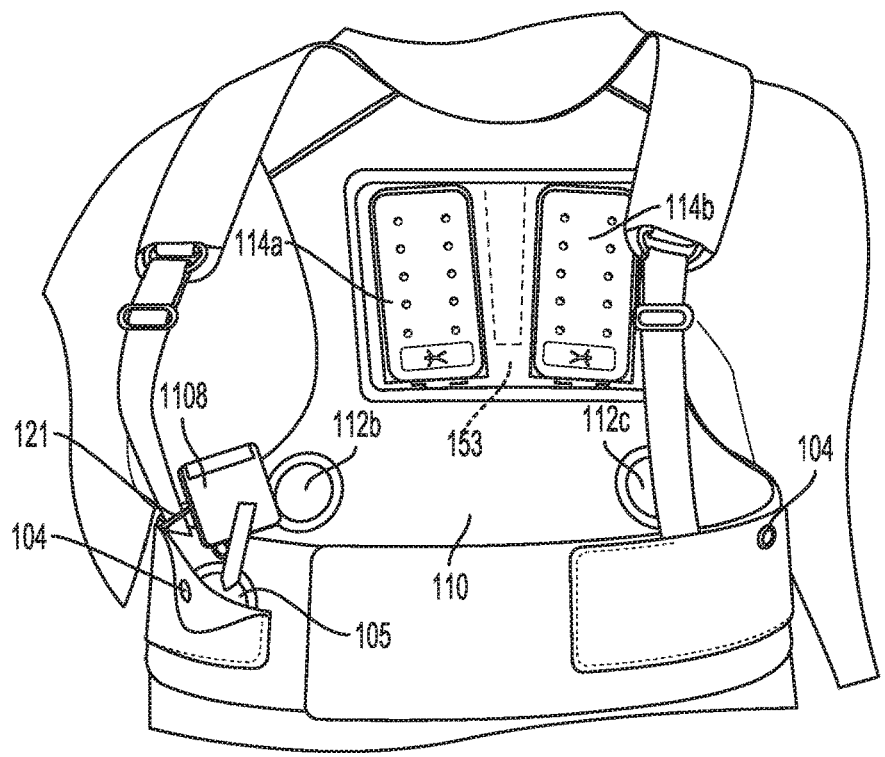
FIG. 15B

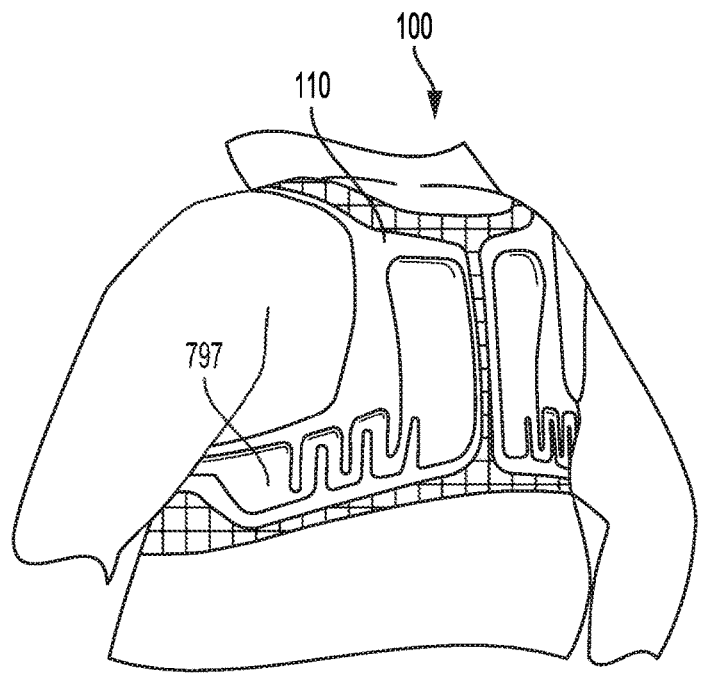
FIG. 24A
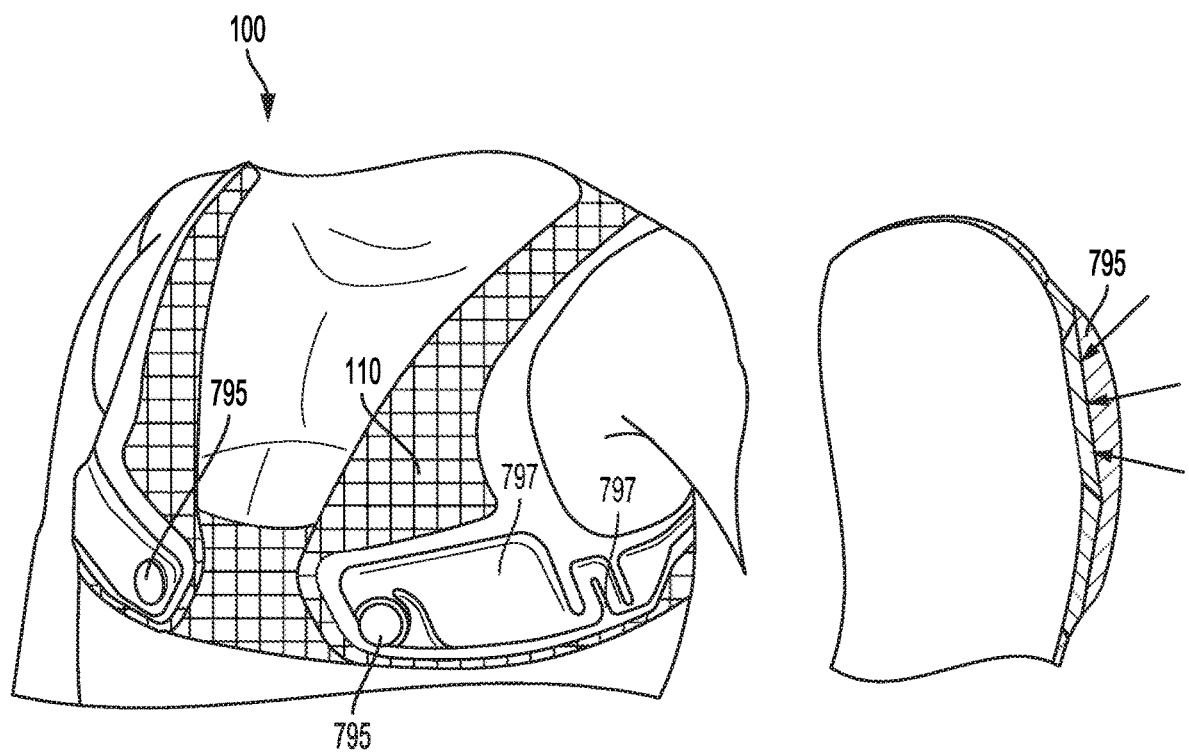
FIG. 24B
FIG. 24C

GARMENTS FOR WEARABLE CARDIAC MONITORING AND TREATMENT DEVICES

CROSS-REFERENCE TO RELATED APPLICATIONS

This application claims priority under 35 U.S.C. § 119(e) to U.S. Provisional Patent Application Ser. No. 62/650,478 filed Mar. 30, 2018, titled "Garments For Wearable Cardiac Monitoring And Treatment Devices," the entirety of which is hereby incorporated by reference.

BACKGROUND

The present disclosure is directed to garments for use with wearable cardiac monitoring and treatment devices.

A wide variety of electronic and mechanical devices monitor and treat medical conditions. In some examples, depending on the underlying medical condition being monitored or treated, medical devices such as cardiac monitors or defibrillators may be surgically implanted or externally connected to a patient. In some cases, physicians may use medical devices alone or in combination with drug therapies to treat conditions such as cardiac arrhythmias.

One of the most deadly cardiac arrhythmias is ventricular fibrillation, which occurs when normal, regular electrical impulses are replaced by irregular and rapid impulses, causing the heart muscle to stop normal contractions. Normal blood flow ceases, and organ damage or death can result in minutes if normal heart contractions are not restored. Because the victim has no perceptible warning of the impending fibrillation, death often occurs before medical assistance can arrive. Other cardiac arrhythmias can include excessively slow heart rates known as bradycardia or excessively fast heart rates known as tachycardia. Cardiac arrest can occur when the heart experiences various arrhythmias that result in the heart providing insufficient levels of blood flow to the brain and other vital organs for the support of life. Such arrhythmias include, for example, ventricular fibrillation, ventricular tachycardia, pulseless electrical activity (PEA), and asystole (heart stops all electrical activity).

Cardiac arrest and other cardiac health ailments are a major cause of death worldwide. Various resuscitation efforts aim to maintain the body's circulatory and respiratory systems during cardiac arrest in an attempt to save the life of the patient. Implementing these resuscitation efforts quickly improves the patient's chances of survival. Implantable cardioverter/defibrillators (ICDs) or external defibrillators (such as manual defibrillators or automated external defibrillators (AEDs)) have significantly improved success rates for treating these otherwise life-threatening conditions. Such devices operate by applying corrective electrical pulses directly to the patient's heart. Ventricular fibrillation or ventricular tachycardia can be treated by an implanted or external defibrillator, for example, by providing a therapeutic shock to the heart in an attempt to restore normal rhythm. To treat conditions such as bradycardia, an implanted or external pacing device can provide pacing stimuli to the patient's heart until intrinsic cardiac electrical activity returns.

Example external cardiac monitoring and/or treatment devices include cardiac monitors, the ZOLL LifeVest® wearable cardioverter defibrillator available from ZOLL Medical Corporation, and the AED Plus also available from ZOLL Medical Corporation.

External pacemakers, defibrillators and other medical monitors designed for ambulatory and/or long-term use have further improved the ability to timely detect and treat life-threatening conditions. For example, certain medical devices operate by continuously monitoring the patient's heart through one or more sensing electrodes for treatable arrhythmias and, when such is detected, the device applies corrective electrical pulses directly to the heart through two or more therapy electrodes.

Example cardiac monitoring and treatment devices can include a vest or garment worn by the patient and monitoring and treatment monitor coupled to electrodes disposed in the vest or garment. These devices are prescribed for continuous wear by the patient for long periods of time. As such, the vest or garment must be optimized for patient comfort and efficacious device operation. Further, patients are generally discouraged from discontinuing use of the device without consulting with their caregivers. Accordingly, the devices are to be worn in compliance with caregiver instructions to ensure maximum protection from adverse events.

SUMMARY

In one example, a wearable cardiac monitoring and treatment device includes a garment configured to be worn continuously about a torso of a patient for an extended period of time, a plurality of electrocardiogram (ECG) sensing electrodes supported by the garment and configured to monitor an ECG signal of the patient, and a plurality of therapy electrodes supported by the garment and configured to provide one or more therapeutic pulses to the patient. The device includes a fastener configured to secure the garment about the torso of the patient for a prescribed duration and a disengagement sensor configured to provide an indication of a disengagement of the fastener prior to expiration of the prescribed duration in which the garment is no longer secured about the torso of the patient. The device also includes a therapy delivery circuit electrically configured to deliver the one or more therapeutic pulses to the patient through the plurality of therapy electrodes and a controller electrically coupled to the plurality of ECG sensing electrodes and the therapy delivery circuit. The controller is configured to detect an arrhythmia condition of the patient based on the monitored ECG signal of the patient and cause the therapy delivery circuit to deliver the one or more therapeutic pulses to the patient on detecting the arrhythmia condition.

Implementations of the device may include one or more of the following features.

In some examples, the disengagement sensor is electrically coupled to the controller and configured to provide the indication of the disengagement of the fastener prior to the expiration of the prescribed duration by generating a signal in response to mechanical disengagement of the fastener. In examples, the controller is configured to receive the signal generated in response to the mechanical disengagement and provide an alert. In examples, the disengagement sensor includes at least one of a capacitive sensor, a hall effect sensor, a reed switch, and an optical proximity sensor. In examples, the controller is configured to store a flag indicative of the mechanical disengagement in a memory of the device for later retrieval. In examples, the alert includes a notification sent to a remote server. In examples, at least one user interface is communicatively coupled to the controller, and the alert includes a notification that is at least one of displayed and transmitted at a user interface. In examples, the alert includes at least one of a tactile alert, an audible alert, and a visual alert.

In examples, additionally or alternatively to an electrically coupled disengagement sensor, the fastener includes a breakaway element that provides physical evidence of the disengagement of the fastener. In examples, the physical evidence can be a physical structure that is at least one of permanently unsealed, broken, separated, and ruptured. In examples, the fastener includes a breakaway element that includes a color-changing element that permanently changes color in response to being stretched beyond a predetermined limit.

In some examples, the device further includes a conductive thread integrated into the garment and configured for coupling to at least one of the controller, the plurality of ECG sensing electrodes, the plurality of therapy electrodes, and the disengagement sensor. In examples, the conductive thread can be woven into the warp and weft of the garment. In examples, the conductive thread can be stitched into the garment. In examples, the conductive thread can be routed in a pocket between two sewn layers of the garment. In examples, the conductive thread can be integrated in an insulated wire attached to or restrained by fasters to the garment.

In examples, the garment includes at least one of a vest worn about the torso of the patient, a wrap-around garment, and a one-shoulder garment configured to be worn about one shoulder and wrap around an upper torso of the patient.

In examples, the device further includes a tensioner for tightening the garment about the torso of the patient while the garment is being worn. The tensioner can be integrated with the fastener.

In some examples, the device further includes at least one integrated vertically corrugated support zone proximate at least one of the plurality of ECG sensing electrodes.

In examples, the device further includes one or more capacitors coupled to the therapy delivery circuit. The therapy delivery circuit can be configured to deliver a discharge of energy from the one or more capacitors.

In some examples, the device further includes at least one user interface communicatively coupled to the controller.

In examples, the controller includes a plurality of modules including one or more capacitors, the therapy delivery circuit, a processor, a user interface, and a network interface, and the plurality of modules are distributed about and secured within the garment.

In examples of the device, the garment is configured to be permeable to transmission of moisture and water vapor from an inner layer towards an outer layer of the garment. For example, the garment can be configured to have a moisture vapor transmission rate of between 100 g/m2/day to 250 g/m2/day. For example, the garment can be configured to have a moisture vapor transmission rate of between 250 g/m2/day to 20,000 g/m2/day. For example, the garment can be configured to have a moisture vapor transmission rate of between 20,000 g/m2/day to 50,000 g/m2/day. In examples of the device, the garment can be configured to be air permeable to promote ventilation through the garment.

In some examples of the device, the garment includes a material that does not result in significant skin irritation after a period of at least about 24 hours following removal of the garment. In certain examples of the device, the garment includes a material that does not result in significant skin irritation after a period of wear of at least about 24 hours.

In some examples of the device, at least one of the plurality of ECG sensing electrodes, the plurality of therapy electrodes, the therapy delivery circuit, and the controller are housed in one or more water-resistant housings. The one or more water-resistant housings can each have a liquid ingress protection rating selected from one or more of: level 3, level 4, level 5, level 6, level 7, and level 8, in accordance with IEC standard 60529.

In yet some examples, a wearable cardiac monitoring and treatment device includes a garment configured to be worn about a torso of a patient for an extended period of time, a plurality of ECG sensing electrodes supported by the garment and configured to be in electrical contact with the patient, and a plurality of therapy electrodes supported by the garment and configured to deliver one or more therapeutic pulses to the patient. The device also includes a plurality of separate modules. The plurality of separate modules include cardiac monitoring circuitry electrically coupled to the plurality of ECG sensing electrodes and disposed in the garment and configured to monitor a cardiac activity of the patient, a therapy delivery circuit configured to control delivery of the one or more therapeutic pulses to the patient, and a controller in communication with the plurality of separate modules. The controller is configured to detect an arrhythmia condition of the patient based on the monitored cardiac activity of the patient, and cause the therapy delivery circuit to provide the one or more therapeutic pulses to the patient in response to detecting the arrhythmia condition of the patient.

Implementations of the device may include one or more of the following features.

The device also includes a plurality of compartments accessible from an outer surface of the garment and configured to receive the plurality of ECG sensing electrodes, the plurality of therapy electrodes, and the plurality of the separate modules, and support, on the outer surface of the garment, wires extending between the plurality of sensing electrodes, the plurality of therapy electrodes, and the plurality of the separate modules.

In some examples, the device further include apertures in at least a portion of the plurality of compartments for providing direct contact between a skin of the patient and the plurality of ECG sensing electrodes configured for insertion into the plurality of compartments.

In some examples, the device further includes at least one thermoform shell integrated into at least one of the plurality of compartments for receiving at least one of the plurality of therapy electrodes.

In examples of the device, the plurality of ECG sensing electrodes, the plurality of therapy electrodes and the plurality of the separate modules each have a size and shape and the plurality of compartments are sized and shaped for receiving each of the plurality of ECG sensing electrodes, the plurality of therapy electrodes and the plurality of the separate modules.

In examples of the device, the plurality of compartments are elastomeric for tautly holding received ECG sensing electrodes, the plurality of therapy electrodes and the plurality of the separate modules.

In examples of the device, the plurality of compartments each have sloped sidewalls and one or more receiving contacts therein for engaging one or more electrical contacts of a ECG sensing electrode, a therapy electrode or one of the plurality of the separate modules.

In some examples of the device, the one or more therapeutic pulses delivered to the patient are defibrillation pulses. In some examples of the device, the one or more therapeutic pulses delivered to the patient are pacing pulses.

In examples of the device, the garment further includes a fastener configured to secure the garment about the torso of the patient for a prescribed duration and a disengagement sensor configured to provide an indication of a disengagement of the fastener prior to expiration of the prescribed duration in which the garment is no longer secured about the torso of the patient. In some examples, the fastener includes a breakaway element that provides physical evidence of the disengagement of the fastener. In examples, the disengagement sensor is electrically coupled to the controller and configured to provide the indication of the disengagement of the fastener prior to the expiration of the prescribed duration by generating a signal in response to mechanical disengagement of the fastener. The controller is configured to receive the signal generated in response to the mechanical disengagement and provide an alert.

In some examples, the device further includes a conductive thread integrated into the garment and configured for coupling to at least one of the controller, the plurality of ECG sensing electrodes, the plurality of therapy electrodes, and the disengagement sensor.

In examples of the device, the garment includes at least one of a vest worn about the torso of the patient, a wrap-around garment, and a one-shoulder garment configured to be worn about one shoulder and wrap around an upper torso of the patient. The garment can include at least one of pleated straps or a pleated torso panel. The garment can include at least one of adjustable straps, elastic straps, and disengageable straps. The garment can defines a continuous loop and further include an expandable side panel closed with a fastener. The garment can be configured to receive interchangeable, anatomically conformed front torso panels.

In examples, the device further includes one or more compartments or retention loops for holding and routing one or more wires against the outer surface of the garment. The one or more wires are configured to couple to at least two of the controller, the plurality of ECG sensing electrodes, the plurality of therapy electrodes, the therapy delivery circuit, and the disengagement sensor.

In still yet some examples, a wearable cardiac monitoring and treatment device includes a garment configured to be worn continuously about a torso of a patient for an extended period of time, a plurality of electrocardiogram (ECG) sensing electrodes supported by the garment and configured to monitor an ECG signal of the patient, and a plurality of therapy electrodes supported by the garment and configured to provide one or more therapeutic pulses to the patient. The device includes a controller electrically coupled to the plurality of ECG sensing electrodes and the therapy delivery circuit. The controller is configured to detect an arrhythmia condition of the patient based on the monitored ECG signal of the patient, and cause the therapy delivery circuit to deliver the one or more therapeutic pulses to the patient on detecting the arrhythmia condition. The device also includes a tensioner for tightening the garment about the torso of the patient while the garment is being worn.

Implementations of the device may include one or more of the following features.

In some examples, the tensioner is configured to cause the garment to secure the plurality of ECG sensing electrodes on the torso of the patient to facilitate the detection of the arrhythmia condition of the patient.

In some examples, the tensioner is configured to cause the garment to secure the plurality of therapy electrodes on the torso of the patient to facilitate the delivery of the one or more therapeutic pulses to the patient.

In some examples, the tensioner is configured to allow the patient to adjust a fit of the garment in accordance with the patient's comfort preferences.

In some examples, the device further includes a fastener configured to secure the garment about the torso of the patient for a prescribed duration. In some examples, the tensioner is configured for tensioning the garment without disengaging the fastener. In some examples, the tensioner is integrated with the fastener.

In examples, the device further includes a disengagement sensor configured to provide an indication of a disengagement of the fastener prior to expiration of the prescribed duration in which the garment is no longer secured about the torso of the patient. In examples, the fastener includes a breakaway element that provides physical evidence of the disengagement of the fastener. In examples, additionally or alternatively to a breakaway element, the disengagement sensor is electrically coupled to the controller and configured to provide the indication of the disengagement of the fastener prior to the expiration of the prescribed duration by generating a signal in response to mechanical disengagement of the fastener. In some examples, the controller is configured to receive the signal generated in response to the disengagement and provide an alert.

In some examples, the device further includes a conductive thread integrated into the garment and configured for coupling to at least one of the controller, the plurality of ECG sensing electrodes, the plurality of therapy electrodes, and the disengagement sensor. In examples, the conductive thread can be woven into the warp and weft of the garment. In examples, the conductive thread can be stitched into the garment. In examples, the conductive thread can be routed in a pocket between two sewn layers of the garment. In examples, the conductive thread can be integrated in an insulated wire attached to or restrained by fasters to the garment.

In examples, the garment includes at least one of a vest worn about the torso of the patient, a wrap-around garment, and a one-shoulder garment configured to be worn about one shoulder and wrap around an upper torso of the patient.

In some examples, the garment of the device further includes at least one integrated vertically corrugated support zone proximate at least one of the plurality of ECG sensing electrodes.

In examples, the device further includes one or more capacitors coupled to the therapy delivery circuit. The therapy delivery circuit can be configured to deliver a discharge of energy from the one or more capacitors.

In some examples, the device further includes at least one user interface communicatively coupled to the controller.

In examples of the device, the garment is configured to be permeable to transmission of moisture and water vapor from an inner layer towards an outer layer of the garment. For example, the garment can be configured to have a moisture vapor transmission rate of between 100 g/m2/day to 250 g/m2/day. For example, the garment can be configured to have a moisture vapor transmission rate of between 250 g/m2/day to 20,000 g/m2/day. For example, the garment can be configured to have a moisture vapor transmission rate of between 20,000 g/m2/day to 50,000 g/m2/day. In examples of the device, the garment can be configured to be air permeable to promote ventilation through the garment.

In some examples of the device, the garment includes a material that does not result in significant skin irritation after a period of at least about 24 hours following removal of the garment. In certain examples of the device, the garment includes a material that does not result in significant skin irritation after a period of wear of at least about 24 hours.

In some examples of the device, at least one of the plurality of ECG sensing electrodes, the plurality of therapy electrodes, the therapy delivery circuit, and the controller are housed in one or more water-resistant housings. The one or more water-resistant housings can each have a liquid ingress protection rating selected from one or more of: level 3, level 4, level 5, level 6, level 7, and level 8, in accordance with IEC standard 60529.

In some examples, a wearable cardiac monitoring and treatment device, includes a garment configured to be worn continuously about a torso of a patient for an extended period of time. The device includes a plurality of electrocardiogram (ECG) sensing electrodes supported by the garment and configured to monitor an ECG signal of the patient, and a plurality of therapy electrodes supported by the garment and configured to provide one or more therapeutic pulses to the patient. A therapy delivery circuit is electrically configured to deliver the one or more therapeutic pulses to the patient through the plurality of therapy electrodes. The device includes one or more sensors supported by the garment, the one or more sensors configured to monitor one or more physiological signals of the patient. The device includes a controller electrically coupled to the plurality of ECG sensing electrodes and the therapy delivery circuit. The controller is configured to detect an arrhythmia condition of the patient based on the monitored ECG signal of the patient, cause the therapy delivery circuit to deliver the one or more therapeutic pulses to the patient on detecting the arrhythmia condition, detect that the garment is no longer worn about the torso of the patient prior to expiration of at least a prescribed duration of wear, and issue a notification that the garment is no longer worn about the torso of the patient.

Implementations of the device may include one or more of the following features.

In examples, detecting that the garment is no longer worn about the torso includes detecting a loss of signal for at least a threshold period of time from at least one of one or more of the plurality of ECG sensing electrodes and one or more of the one or more sensors prior to expiration of at least the prescribed duration of wear. In examples, the detection of the loss of signal is preceded by continuous monitoring of the ECG signal without detecting an arrhythmia condition.

In examples, the controller issues the notification that the garment is no longer worn about the torso of the patient in response to the detection of the loss of signal for at least the threshold period of time. In examples, the threshold period of time includes a duration ranging from 1 to 5 minutes. In some examples, the patient could control the duration under the direction of a physician or caregiver and configure the threshold period of time to a duration lasting minutes, hours, and/or days. In examples, the threshold period of time could be 1-5 minutes, 1-10 minutes, 1-30 minutes, 1 hour, 2 hours, 5 hours, 1 day, or 2 days. In examples, the threshold period of time includes a duration ranging from 1-30 seconds, such that the controller is configured to immediately provide the notification upon detecting the loss of signal. In examples, the notification includes at least one of an audible, visible, and haptic alert provided to at least one of the patient and a remote caregiver.

In examples, the one or more sensors includes at least one of a blood oxygen sensor, a patient temperature sensor, a galvanic skin response (GSR) sensor, a bioimpedance sensor, a pethysmographic sensor, a near infrared spectroscopy (NIRS) sensor, a glucose level sensor, a tissue fluid level sensor, a pulmonary vibration sensor, and a patient movement sensor.

In examples, the device also includes a fastener configured to secure the garment about the torso of the patient for at least the prescribed duration of wear, and a disengagement sensor configured to provide an indication of a disengagement of the fastener prior to expiration of at least the prescribed duration of wear in which the garment is no longer secured about the torso of the patient. In examples, the disengagement sensor is electrically coupled to the controller and configured to provide the indication of the disengagement of the fastener prior to the expiration of at least the prescribed duration by generating a signal in response to mechanical disengagement of the fastener. In examples, the controller is configured to receive the signal generated in response to the mechanical disengagement and provide the notification that the garment is no longer worn about the torso of the patient.

The details of one or more implementations of the subject matter described in this specification are set forth in the accompanying drawings and the description. Other features and advantages will be apparent from the description, drawings, and the claims. In the figures, each identical or nearly identical component that is illustrated in various figures is represented by a like numeral. For purposes of clarity, not every component may be labeled in every figure.

BRIEF DESCRIPTION OF THE DRAWINGS

FIG. 15A depicts a backside view of an embodiment of a patient-worn medical device having concealed wires.

FIG. 15B depicts a front view of an embodiment of a patient-worn medical device having concealed wires.

FIG. 15C depicts an embodiment of a sensor for use with the embodiment of the patient-worn medical device of FIGS. 15A and 15B.

FIG. 24A depicts a rear perspective view of an embodiment of a patient-worn medical device.

FIG. 24B depicts a front perspective view of the device of FIG. 24A.

FIG. 24C depicts a magnified view of a portion of the device of FIGS. 24A and 24B.

DETAILED DESCRIPTION

Figure 1:
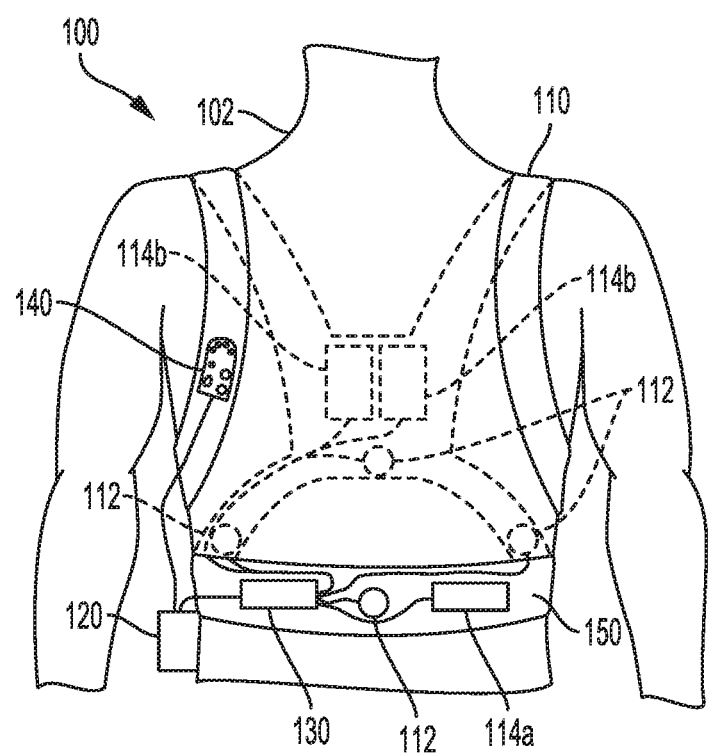
FIG. 1 depicts an embodiment of a patient-worn medical device.

This disclosure relates to a patient-worn cardiac monitoring and treatment device (hereinafter also referred to as a "wearable medical device" or simply "device") that detects one or more treatable arrhythmias based on physiological signals from a patient. The treatable arrhythmias include those that may be treated by defibrillation pulses, such as ventricular fibrillation (VF) and shockable ventricular tachycardia (VT), or by pacing pulses, such as bradycardia, tachycardia, and asystole. A wearable medical device as disclosed herein monitors a patient's physiological conditions, e.g., cardiac signals, respiratory parameters, and patient activity, and delivers potentially life-saving treatment to the patient. The medical device can include a plurality of sensing electrodes that are disposed at various locations on the patient's body and configured to monitor the cardiac signals of the patient such as electrocardiogram (ECG) signals. In some implementations, the device can also be configured to allow a patient to report his/her symptoms including one or more skipped beat(s), shortness of breath, light headedness, racing heart, fatigue, fainting, and chest discomfort. The device determines an appropriate treatment for the patient based on the detected cardiac signals and/or other physiological parameters prior to delivering a therapy to the patient. The device then causes one or more therapeutic shocks, for example, defibrillating and/or pacing shocks, to be delivered to the body of the patient. The wearable medical device includes a plurality of therapy electrodes disposed on the patient's body and configured to deliver the therapeutic shocks. Systems and techniques are disclosed herein to improve the ergonomics of garments and/or aspects of garments that are part of such a wearable medical device.

The devices described here are prescribed to be worn continuously and for long durations of time, often over the course of several weeks or months. For example, a prescribed duration can be a duration for which a patient is instructed by a caregiver to wear the device in compliance with device use instructions. A device designed for an extended duration of wear may be prescribed for some or all of the designed duration as described subsequently.

A sudden cardiac arrest or other arrhythmia condition can strike at any time and with little warning. Patients are encouraged to comply with the device use guidelines, including wearing the device at all times including while showering or sleeping. To improve patient compliance with these guidelines, the devices described herein are lightweight, comfortable, and discreet so that they may be worn under the patient's clothing. Moreover, the devices are configured to allow for uncomplicated assembly and disassembly as required. In some implementations described herein, the devices include various features that promote comfort in accordance with patient's comfort preferences, even weight distribution, ease of assembly and disassembly, and discreet wear while continuing to protect the patient from adverse cardiac events. In certain implementations described herein, the device can be locked or otherwise secured about the body of the patient for the duration of the prescribed period of use. For example, the device may be locked about the patient's body in a manner so as to indicate when the patient or other person removes or attempts to remove the device prior to the end of the prescribed duration.

In implementations, the garment portion of the device is configured to be worn or otherwise secured about the torso of the patient. A plurality of energy storage units are operably connected to a therapy delivery circuit. The plurality of energy storage units as well as the therapy delivery circuit are housed within a plurality of physically separate modules. In some implementations, these modules are housed in various locations within the garment. For example, the modules can be located in compartments or otherwise distributed within the garment so as to create an ergonomic distribution of the modules. The energy storage units are configured to store energy for at least one therapeutic pulse. The therapy delivery circuit is configured to cause the delivery of the at least one therapeutic pulse via the plurality of therapy electrodes. In implementations, the energy storage units are electrically coupled by one or more cables to the plurality of therapy electrodes. For example, the one or more cables are electrically insulated and physically isolated from the skin of the patient and other components of the device when the garment is assembled along with the includes plurality of energy storage units, therapy delivery circuit, and therapy electrodes.

As noted above, the wearable medical device, including the garment, is configured for continuous and long-term wear by a patient. Accordingly, embodiments of the device address enhanced patient comfort and ease of use, including donning and removing the device and interacting with and adjusting the device while worn. In some implementations, loose cables, or wires, are routed securely to prevent snagging or interference with patient movement. In some implementations, the garment includes a fastener configured to secure the garment about the torso of the patient. The fastener may be configured for accessibility by arthritic patients and patients with reduced range of motion. Some implementations of the garment include skin interfaces that improve comfort by reducing patient contact with potential irritants in the device. Additionally, the garment features one or more configurations for securing device sensors disposed on an inner fabric of the garment and held against the patient's skin in a comfortable manner. These configurations, for example, prevent the sensors from excessive lateral movement, flipping over, or losing contact with the patient during wear. In this manner, the garments can eliminate or minimize sensor signal noise and other artifacts. In some examples, the device includes elements that enable adjusting the locations of one or more of the sensing electrodes, therapy electrodes, and certain controller components, such as the capacitors and battery.

In implementations, the wearable medical device includes a fastener configured to lock or otherwise secure the garment about the torso of the patient for a prescribed duration. For example, a disengagement sensor can be provided to indicate if and when the fastener is disengaged prior to expiration of the prescribed duration. In implementations, the disengagement sensor is electrically coupled to the controller and configured to provide an indication of the disengagement. For instance, the disengagement sensor can provide the indication of the disengagement by generating an electrical signal in response to mechanical disengagement of the fastener. For example, as described later, the disengagement sensor can include a proximity sensor, such as a capacitive sensor, a hall effect sensor, a reed switch, or an optical proximity sensor. Alternatively or additionally, premature disengagement and removal of the wearable medical device can be detected by one of more electrodes losing contact with the body of the patient and not sensing, for example, an ECG signal, for longer than a threshold period. Alternatively or additionally, the disengagement sensor can include a physical structure that provides physical evidence of disengagement. For example, such a structure can include a breakaway element that is permanently unsealed, broken, separated, ruptured, or otherwise compromised upon disengagement. The breakaway element can include, for example, a frangible wrapper that permanently separates into two or more portions. In some implementations, the breakaway element can include a color-changing element that permanently changes color in response to being stretched beyond a predetermined limit.

In some configurations, for example, the controller receives the electrical signal generated in response to the mechanical disengagement of the fastener and provides an alert. In embodiments, the alert is a flag stored in memory for later retrieval. In embodiments, the alert is a notification sent to a remote server. In other embodiments, the device includes at least one user interface communicatively coupled to the controller, and the alert is a notification displayed or transmitted at a user interface of the device. In some implementations, the alert may be one or more of a tactile alert, an audible alert, or a visual alert. In implementations, the device includes a conductive wire integrated into the garment to electrically couple the disengagement sensor to the controller. The wire can be integrated into the garment, for example, by weaving it into the warp and weft of the garment, stitching it into one or more layers of the garment, or retaining the conductive wire against an interior or exterior surface of the garment with one or more retention loops or restraints. In some implementations, the controller is configured to provide an alert during the period of disengagement of the device from the patient, including disengagement of one or more of the sensing electrodes, therapy electrodes, and controller components so that the patient is reminded to reattach the disengaged device or components.

As described above, the wearable medical device described herein is capable of continuous use by the patient. Such continuous use can be substantially or nearly continuous in nature. During substantially continuous or nearly continuous use, the wearable medical device may be continuously used except for sporadic periods during which the use temporarily ceases (e.g., while the patient bathes, while the patient is refit with a new and/or a different garment, while the battery is charged/changed, while the garment is laundered, etc.). Such substantially continuous or nearly continuous use as described herein may nonetheless qualify as continuous use. In some implementations, the patient may remove the wearable medical device for a short portion of the day (e.g., for half an hour while bathing).

Further, the wearable medical device can be configured as a long term or extended use medical device. Such devices can be designed to be used by the patient for an extended period of time, for example, a period of 24 hours or more, several days, weeks, months, or even years. Accordingly, the extended period of use can be uninterrupted until a physician or other caregiver provides specific prescription to the patient to stop use of the wearable medical device. For example, the wearable medical device can be prescribed for use by a patient for a period of at least one week. In an example, the wearable medical device can be prescribed for use by a patient for a period of at least 30 days. In an example, the wearable medical device can be prescribed for use by a patient for a period of at least one month. In an example, the wearable medical device can be prescribed for use by a patient for a period of at least two months. In an example, the wearable medical device can be prescribed for use by a patient for a period of at least three months. In an example, the wearable medical device can be prescribed for use by a patient for a period of at least six months. In an example, the wearable medical device can be prescribed for use by a patient for an extended period of at least one year.

Regardless of the period of wear, the use of the wearable medical device can include continuous or nearly continuous wear by the patient as previously described. For example, the continuous use can include continuous wear or attachment of the wearable medical device to the patient. In implementations, the continuous attachment is through one or more of the electrodes as described herein during both periods of monitoring and periods when the device may not be monitoring the patient but is otherwise still worn by or otherwise attached to the patient. Continuous use can include continuously monitoring the patient while the patient is wearing the device for cardiac-related information (e.g., electrocardiogram (ECG) information, including arrhythmia information, cardiac vibrations, etc.) and/or non-cardiac information (e.g., blood oxygen, the patient's temperature, glucose levels, tissue fluid levels, and/or pulmonary vibrations). For example, the wearable medical device can carry out its continuous monitoring and/or recording in periodic or aperiodic time intervals or times (e.g., every few minutes, hours, once a day, once a week, or other interval set by a technician or prescribed by a caregiver). Alternatively or additionally, the monitoring and/or recording during intervals or times can be triggered by a user action or another event.

As noted above, the wearable medical device can be configured to monitor other physiologic parameters of the patient in addition to cardiac related parameters. For example, the wearable medical device can be configured to monitor, for example, pulmonary vibrations (e.g., using microphones and/or accelerometers), breath vibrations, sleep related parameters (e.g., snoring, sleep apnea), and tissue fluids (e.g., using radio-frequency transmitters and sensors), among others.

In implementations, an example wearable medical device can include an in-hospital continuous monitoring defibrillator and/or pacing device such as, for example, an in-hospital wearable defibrillator. A patient being monitored by an in-hospital defibrillator and/or pacing device may be confined to a hospital bed or room for a significant amount of time (e.g., 90 percent or more of the patient's stay in the hospital). As a result, a user interface can be configured to interact with a user other than the patient (e.g., a nurse, a technician, a home caretaker, a patient care representative, etc.) for device-related functions such as initial device baselining, setting and adjusting patient parameters, and changing the device batteries. In implementations, an example of a wearable medical device can include a short-term continuous monitoring defibrillator and/or pacing device, for example, a short-term outpatient wearable defibrillator. For example, such a short-term outpatient wearable defibrillator can be prescribed by a caregiver, such as a physician, for patients presenting with syncope at a hospital or emergency care facility. The short-term device can be configured to monitor patients presenting with syncope by, for example, analyzing the patient's cardiac activity for aberrant patterns that can indicate abnormal physiological function. For example, such aberrant patterns can occur prior to, during, or after the onset of symptoms. In such an example implementation of the short-term wearable defibrillator, the electrode assembly can be adhesively attached to the patient's skin. Short-term wear includes periods of fewer than 24 hours, fewer than 48 hours, fewer than 72 hours, less than a week, and less than two weeks. Short-term wear includes, for example, durations up to and including but no longer than 14 days.

FIG. 1 illustrates an example medical device 100 that is external, ambulatory, and wearable by a patient, and configured to implement one or more configurations described herein. The medical device 100 is an external or non-invasive medical device, which, for example, is located external to the body of the patient and configured to provide transcutaneous therapy to the body. The medical device 100 is an ambulatory medical device, which, for example, is capable of and designed for moving with the patient as the patient goes about his or her daily routine. The medical device 100 can be bodily-attached to the patient in a manner similar to the LifeVest® wearable cardioverter defibrillator (WCD) available from ZOLL® Medical Corporation (Chelmsford, Mass.).

The medical device 100 can include one or more of the following: a garment 110, one or more sensing electrodes 112 (e.g., ECG sensing electrodes) configured to be in electrical contact with the patient, a plurality of therapy electrodes 114a and 114b (collectively referred to herein as therapy electrodes 114), a medical device controller 120, a connection pod 130, a user interface device 140, a belt 150, or any combination of these. In some examples, at least some of the components of the medical device 100 can be configured to be affixed to the garment 110 (or in some examples, permanently secured into the garment 110), which can be worn about the patient's torso. Additional implementations of sensing electrode arrangements and therapy electrode arrangements on a patient-worn medical device are provided herein in subsequent sections.

The medical device controller 120 can be operatively coupled to the sensing electrodes 112, which can be affixed to the garment 110. In embodiments, the sensing electrodes 112 are assembled into the garment 110 or removably attached to the garment, using, for example, hook and loop fasteners, thermoform press fit receptacles, snaps, and magnets, among other restraints. In some implementations, the sensing electrodes 112 can be a permanent portion of the garment 110. The medical device controller 120 also can be operatively coupled to the therapy electrodes 114. For example, the therapy electrodes 114 can also be assembled into the garment 110, or, in some implementations, the therapy electrodes 114 can be a permanent portion of the garment 110.

The sensing electrodes 112 can be configured to detect one or more cardiac signals such as ECG signals. Example sensing electrodes 112 include a metal electrode with an oxide coating such as tantalum pentoxide electrodes, as described in, for example, U.S. Pat. No. 6,253,099 entitled "Cardiac Monitoring Electrode Apparatus and Method," the content of which is incorporated herein by reference.

The connection pod 130, in some examples, includes a signal processor configured to amplify, filter, and digitize the cardiac signals prior to transmitting the cardiac signals to the medical device controller 120. One or more of the therapy electrodes 114 is configured to deliver one or more therapeutic defibrillating shocks to the body 102 of the patient when the medical device 100 determines that such treatment is warranted based on the signals detected by the sensing electrodes 112 and processed by the medical device controller 120. Example therapy electrodes 114 include, for example, conductive metal electrodes such as stainless steel electrodes that include, in certain implementations, one or more conductive gel deployment devices configured to deliver conductive gel to the metal electrode prior to delivery of a therapeutic shock.

Figure 2:
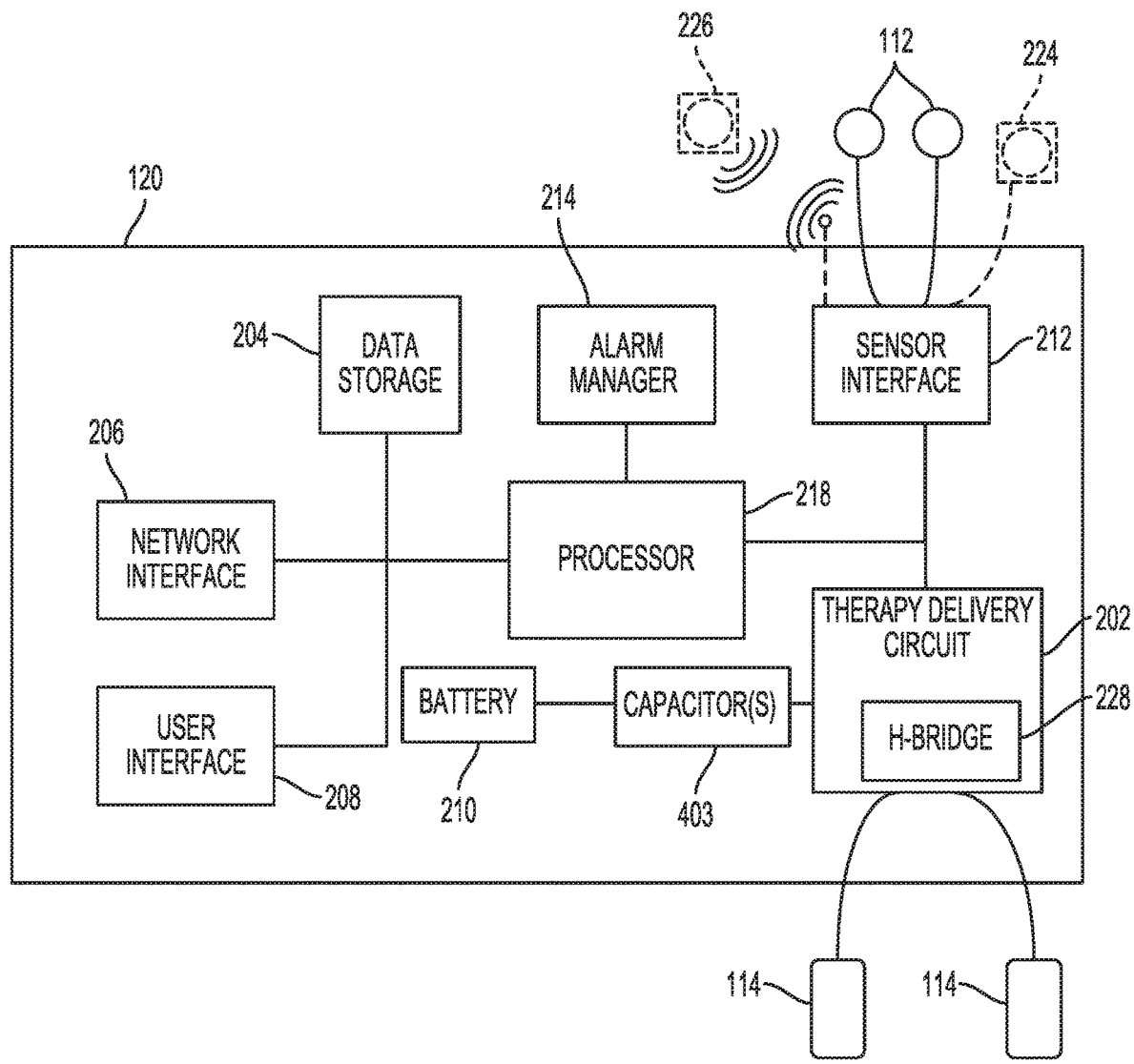
FIG. 2 depicts a schematic diagram of an embodiment of a medical device controller of a patient-worn medical device.

FIG. 2 illustrates a sample component-level view of the medical device controller 120. As shown in FIG. 2, the medical device controller 120 can include a therapy delivery circuit 202 including a polarity switching component such as an H-bridge 228, a data storage 204, a network interface 206, a user interface 208, at least one battery 210, a sensor interface 212, an alarm manager 214, least one processor 218, one or more capacitors 403, and a battery 210. A patient monitoring medical device can include a medical device controller 120 that includes like components as those described above, but does not include the therapy delivery circuit 202.

The therapy delivery circuit 202 is coupled to two or more therapy electrodes 114 configured to provide therapy to the patient (e.g., the therapy electrodes 114 as described above in connection with FIG. 1). For example, the therapy delivery circuit 202 includes, or is operably connected to, circuitry components that are configured to generate and provide the therapeutic shock. The circuitry components include, for example, resistors, one or more capacitors, relays and/or switches, an electrical bridge such as an H-bridge 228 (e.g., an H-bridge including a plurality of insulated gate bipolar transistors or IGBTs that deliver and truncate a therapy pulse), voltage and/or current measuring components, and other similar circuitry arranged and connected such that the circuitry work in concert with the therapy delivery circuit and under control of one or more processors (e.g., processor 218) to provide, for example, one or more pacing or defibrillation therapeutic pulses.

Pacing pulses can be used to treat cardiac arrhythmias such as bradycardia (e.g., in some implementations, less than 30 beats per minute) and tachycardia (e.g., in some implementations, more than 150 beats per minute) using, for example, fixed rate pacing, demand pacing, anti-tachycardia pacing, and the like. Defibrillation pulses can be used to treat ventricular tachycardia and/or ventricular fibrillation.

In implementations, each of the therapy electrodes 114 has a conductive surface adapted for placement adjacent the patient's skin and has an impedance reducing means contained therein or thereon for reducing the impedance between a therapy electrode and the patient's skin. In implementations, the patient-worn arrhythmia monitoring and treatment device 100 may include gel deployment circuitry configured to cause the delivery of conductive gel substantially proximate to a treatment site (e.g., a surface of the patient's skin in contact with the therapy electrode 114) prior to delivering therapeutic shocks to the treatment site. As described in U.S. Pat. No. 9,008,801, titled "WEARABLE THERAPUETIC DEVICE," issued on Apr. 14, 2015 (hereinafter the "'801 patent"), which is hereby incorporated herein by reference in its entirety, the gel deployment circuitry may be configured to cause the delivery of conductive gel immediately before delivery of the therapeutic shocks to the treatment site, or within a short time interval, for example, within about 1 second, 5 seconds, 10 seconds, 30 seconds, or one minute before delivery of the therapeutic shocks to the treatment site. Such gel deployment circuitry may be coupled to or integrated within a therapy electrode 114 or other therapy delivery device as a single unit. When a treatable cardiac condition is detected and no patient response is received after device prompting, the gel deployment circuitry can be signaled to deploy the conductive gel. In some examples, the gel deployment circuitry may be constructed as one or more separate and independent gel deployment modules. Such modules may be configured to receive removable and/or replaceable gel cartridges (e.g., cartridges that contain one or more conductive gel reservoirs). As such, the gel deployment circuitry may be permanently disposed in the garment as part of the therapy delivery systems, while the cartridges may be removable and/or replaceable.

In some implementations, the gel deployment modules may be implemented as gel deployment packs and include at least a portion of the gel deployment circuitry along with one or more gel reservoirs within the gel deployment pack. In such implementations, the gel deployment pack, including the one or more gel reservoirs and associated gel deployment circuitry may be removable and/or replaceable. In some examples, the gel deployment pack, including the one or more gel reservoirs and associated gel deployment circuitry, and the therapy electrode can be integrated into a therapy electrode assembly that can be removed and replaced as a single unit either after use, or if damaged or broken.

Continuing with the description of the example medical device controller 120 of FIG. 2, in implementations, the one or more capacitors 403 is a plurality of capacitors (e.g., two, three, four or more capacitors) comprising a capacitor bank 402. These capacitors 403 can be switched into a series connection during discharge for a defibrillation pulse. For example, four capacitors of approximately 650 g can be used. In one implementation, the capacitors can have between 200 to 2500 volt surge rating and can be charged in approximately 5 to 30 seconds from a battery 210 depending on the amount of energy to be delivered to the patient. Additional implementations of capacitor properties and arrangements on a patient-worn medical device 100 are provided herein in subsequent sections.

For example, each defibrillation pulse can deliver between 60 to 400 joules (J) of energy. In some implementations, the defibrillating pulse can be a biphasic truncated exponential waveform, whereby the signal can switch between a positive and a negative portion (e.g., charge directions). An amplitude and a width of the two phases of the energy waveform can be automatically adjusted to deliver a predetermined energy amount.

The data storage 204 can include one or more of non-transitory computer readable media, such as flash memory, solid state memory, magnetic memory, optical memory, cache memory, combinations thereof, and others. The data storage 204 can be configured to store executable instructions and data used for operation of the medical device controller 120. In certain implementations, the data storage 204 can include executable instructions that, when executed, are configured to cause the processor 218 to perform one or more functions.

In some examples, the network interface 206 can facilitate the communication of information between the medical device controller 120 and one or more other devices or entities over a communications network. For example, where the medical device controller 120 is included in an ambulatory medical device (such as medical device 100), the network interface 206 can be configured to communicate with a remote computing device such as a remote server or other similar computing device. The network interface 206 can include communications circuitry for transmitting data in accordance with a Bluetooth® wireless standard for exchanging such data over short distances to an intermediary device(s) (e.g., a base station, a "hotspot" device, a smartphone, a tablet, a portable computing device, and/or other devices in proximity of the wearable medical device 100). The intermediary device(s) may in turn communicate the data to a remote server over a broadband cellular network communications link, The communications link may implement broadband cellular technology (e.g., 2.5G, 2.75G, 3G, 4G, 5G cellular standards) and/or Long-Term Evolution (LTE) technology or GSM/EDGE and UMTS/HSPA technologies for high-speed wireless communication. In some implementations, the intermediary device(s) may communicate with a remote server over a Wi-Fi™ communications link based on the IEEE 802.11 standard.

In certain implementations, the user interface 208 can include one or more physical interface devices such as input devices, output devices, and combination input/output devices and a software stack configured to drive operation of the devices. These user interface elements may render visual, audio, and/or tactile content. Thus, the user interface 208 may receive input or provide output, thereby enabling a user to interact with the medical device controller 120. In some implementations, the user interface 208 may be implanted as a hand-held user interface device. (See, for example, the user interface device 140 of FIG. 1.) For instance, the hand-held user interface device may be a smartphone or other portable device configured to communicate with the controller 120 via the network interface 206. In an implementation, the hand-held user interface device may also be the intermediary device for facilitating the transfer of information from the device 100 to the remote server.

As described, the medical device controller 120 can also include at least one battery 210 configured to provide power to one or more components, such as the one or more capacitors 403, integrated in the medical device controller 120 or, in some embodiments, into the garment 110 of the medical device 100. The battery 210 can include a rechargeable multi-cell battery pack. In one example implementation, the battery 210 can include three or more 2200 mAh lithium ion cells that provide electrical power to the other device components within the medical device controller 120. For example, the battery 210 can provide its power output in a range of between 20 mA to 1000 mA (e.g., 40 mA) output and can support 24 hours, 48 hours, 72 hours, or more, of runtime between charges. In certain implementations, the battery capacity, runtime, and type (e.g., lithium ion, nickel-cadmium, or nickel-metal hydride) can be changed to best fit the specific application of the medical device controller 120.

The sensor interface 212 can be coupled to one or more sensors configured to monitor one or more physiological parameters of the patient. As shown in FIG. 2, the sensors may be coupled to the medical device controller 120 via a wired or wireless connection. The sensors can include one or sensing electrodes 112 (e.g., electrocardiogram (ECG) electrodes 112), vibrations sensors 224, and tissue fluid monitors 226 (e.g., based on ultra-wide band radiofrequency devices).

The sensing electrodes 112 can monitor, for example, a patient's ECG information. For example, the sensing electrodes 112 can include conductive electrodes with stored gel deployment (e.g., metallic electrodes with stored conductive gel configured to be dispersed in the electrode-skin interface when needed), or dry electrodes (e.g., a metallic substrate with an oxide layer in direct contact with the patient's skin). The sensing electrodes 112 can be configured to measure the patient's ECG signals. The sensing electrodes 112 can transmit information descriptive of the ECG signals to the sensor interface 212 for subsequent analysis.

The vibration sensors 224 can detect a patient's cardiac or pulmonary (cardiopulmonary) vibration information. For example, the cardiopulmonary vibrations sensors 224 can be configured to detect heart valve vibration values including any one or all of S1, S2, S3, and S4. From these heart valve vibration values, certain electromechanical metrics may be calculated, including any one or more of electromechanical activation time (EMAT), percentage of EMAT (% EMAT), systolic dysfunction index (SDI), and left ventricular systolic time (LVST). The cardiopulmonary vibrations sensors 224 may also be configured to detect hear wall motion, for example, by placement of the sensor 224 in the region of the apical beat. The vibrations sensors 224 can include an acoustic sensor configured to detect vibrations from a subject's cardiac or pulmonary (cardiopulmonary) system and provide an output signal responsive to the detected vibrations of the targeted organ. For instance, in some implementations, the vibrations sensors 224 are able to detect vibrations generated in the trachea or lungs due to the flow of air during breathing. The vibrations sensors 224 can also include a multi-channel accelerometer, for example, a three channel accelerometer configured to sense movement in each of three orthogonal axes such that patient movement/body position can be detected. The vibrations sensors 224 can transmit information descriptive of the cardiopulmonary vibrations information or patient position/movement to the sensor interface 212 for subsequent analysis.

The tissue fluid monitors 226 can use radio frequency (RF) based techniques to assess changes of accumulated fluid levels over time. For example, the tissue fluid monitors 226 can be configured to measure fluid content in the lungs (e.g., time-varying changes and absolute levels), for diagnosis and follow-up of pulmonary edema or lung congestion in heart failure patients. The tissue fluid monitors 226 can include one or more antennas configured to direct RF waves through a patient's tissue and measure output RF signals in response to the waves that have passed through the tissue. In certain implementations, the output RF signals include parameters indicative of a fluid level in the patient's tissue. The tissue fluid monitors 226 can transmit information descriptive of the tissue fluid levels to the sensor interface 212 for subsequent analysis.

The sensor interface 212 can be coupled to any one or combination of sensing electrodes/other sensors to receive other patient data indicative of patient parameters. Once data from the sensors has been received by the sensor interface 212, the data can be directed by the processor 218 to an appropriate component within the medical device controller 120. For example, if cardiac data is collected by the cardiopulmonary vibrations sensor 224 and transmitted to the sensor interface 212, the sensor interface 212 can transmit the data to the processor 218 which, in turn, relays the data to a cardiac event detector. The cardiac event data can also be stored on the data storage 204.

An alarm manager 214 can be configured to manage alarm profiles and notify one or more intended recipients of events specified within the alarm profiles as being of interest to the intended recipients. These intended recipients can include external entities such as users (e.g., patients, physicians, and monitoring personnel) as well as computer systems (e.g., monitoring systems or emergency response systems). The alarm manager 214 can be implemented using hardware or a combination of hardware and software. For instance, in some examples, the alarm manager 214 can be implemented as a software component that is stored within the data storage 204 and executed by the processor 218. In this example, the instructions included in the alarm manager 214 can cause the processor 218 to configure alarm profiles and notify intended recipients according to the configured alarm profiles. In some examples, alarm manager 214 can be an application-specific integrated circuit (ASIC) that is coupled to the processor 218 and configured to manage alarm profiles and notify intended recipients using alarms specified within the alarm profiles. Thus, examples of alarm manager 214 are not limited to a particular hardware or software implementation.

In some implementations, the processor 218 includes one or more processors (or one or more processor cores) that each are configured to perform a series of instructions that result in manipulated data and/or control the operation of the other components of the medical device controller 120. In some implementations, when executing a specific process (e.g., cardiac monitoring), the processor 218 can be configured to make specific logic-based determinations based on input data received, and be further configured to provide one or more outputs that can be used to control or otherwise inform subsequent processing to be carried out by the processor 218 and/or other processors or circuitry with which processor 218 is communicatively coupled. Thus, the processor 218 reacts to a specific input stimulus in a specific way and generates a corresponding output based on that input stimulus. In some example cases, the processor 218 can proceed through a sequence of logical transitions in which various internal register states and/or other bit cell states internal or external to the processor 218 may be set to logic high or logic low. As referred to herein, the processor 218 can be configured to execute a function stored in software. For example, such software may be stored in a data store coupled to the processor 218 and configured to cause the processor 218 to proceed through a sequence of various logic decisions that result in the function being executed. The various components that are described herein as being executable by the processor 218 can be implemented in various forms of specialized hardware, software, or a combination thereof. For example, the processor can be a digital signal processor (DSP) such as a 24-bit DSP processor. The processor can be a multi-core processor, e.g., a processor having two or more processing cores. The processor can be an Advanced RISC Machine (ARM) processor such as a 32-bit ARM processor. The processor can execute an embedded operating system and include services provided by the operating system that can be used for file system manipulation, display & audio generation, basic networking, firewalling, data encryption and communications.

In implementations, the therapy delivery circuit 202 includes, or is operably connected to, circuitry components that are configured to generate and provide the therapeutic shock. As described previously, the circuitry components include, for example, resistors, one or more capacitors 403, relays and/or switches, an electrical bridge such as an H-bridge 228 (e.g., an H-bridge circuit including a plurality of switches, (e.g. insulated gate bipolar transistors or IGBTs, silicon carbide field effect transistors (SiC FETs), metal-oxide semiconductor field effect transistors (MOSFETS), silicon-controlled rectifiers (SCRs), or other high current switching devices)), voltage and/or current measuring components, and other similar circuitry components arranged and connected such that the circuitry components work in concert with the therapy delivery circuit 202 and under control of one or more processors (e.g., processor 218) to provide, for example, one or more pacing or defibrillation therapeutic pulses.

In implementations, the device 100 further includes a source of electrical energy, for example, the one or more capacitors 403, that stores and provides energy to the therapy delivery circuit 202. The one or more therapeutic pulses are defibrillation pulses of electrical energy, and the one or more treatable arrhythmias include ventricular fibrillation and ventricular tachycardia. In implementations, the one or more therapeutic pulses are biphasic exponential pulses. Such therapeutic pulses may be generated by charging the one or more capacitors 403 and discharging the energy stored in the one or more capacitors 403 into the patient. For example, the therapy delivery circuit 202 can include one or more power converters for controlling the charging and discharging of the one or more capacitors 403. In some implementations, the discharge of energy from the one or more capacitors 403 may be controlled by, for example, an H-bridge 228 depicted in FIG. 3. The H-bridge 228 of FIG. 3 controls the discharge of energy into the patient body 102 like the H-bridge circuit described in U.S. Pat. No. 6,280,461, titled "PATIENT-WORN ENERGY DELIVERY APPARATUS," issued on Aug. 28, 2001 (hereinafter the "'461 patent"), and U.S. Pat. No. 8,909,335, titled "METHOD AND APPARATUS FOR APPLYING A RECTILINEAR BIPHASIC POWER WAVEFORM TO A LOAD," issued on Dec. 9, 2014 (hereinafter the "'335 patent"), each of which is hereby incorporated herein by reference in its entirety.

Figure 3:
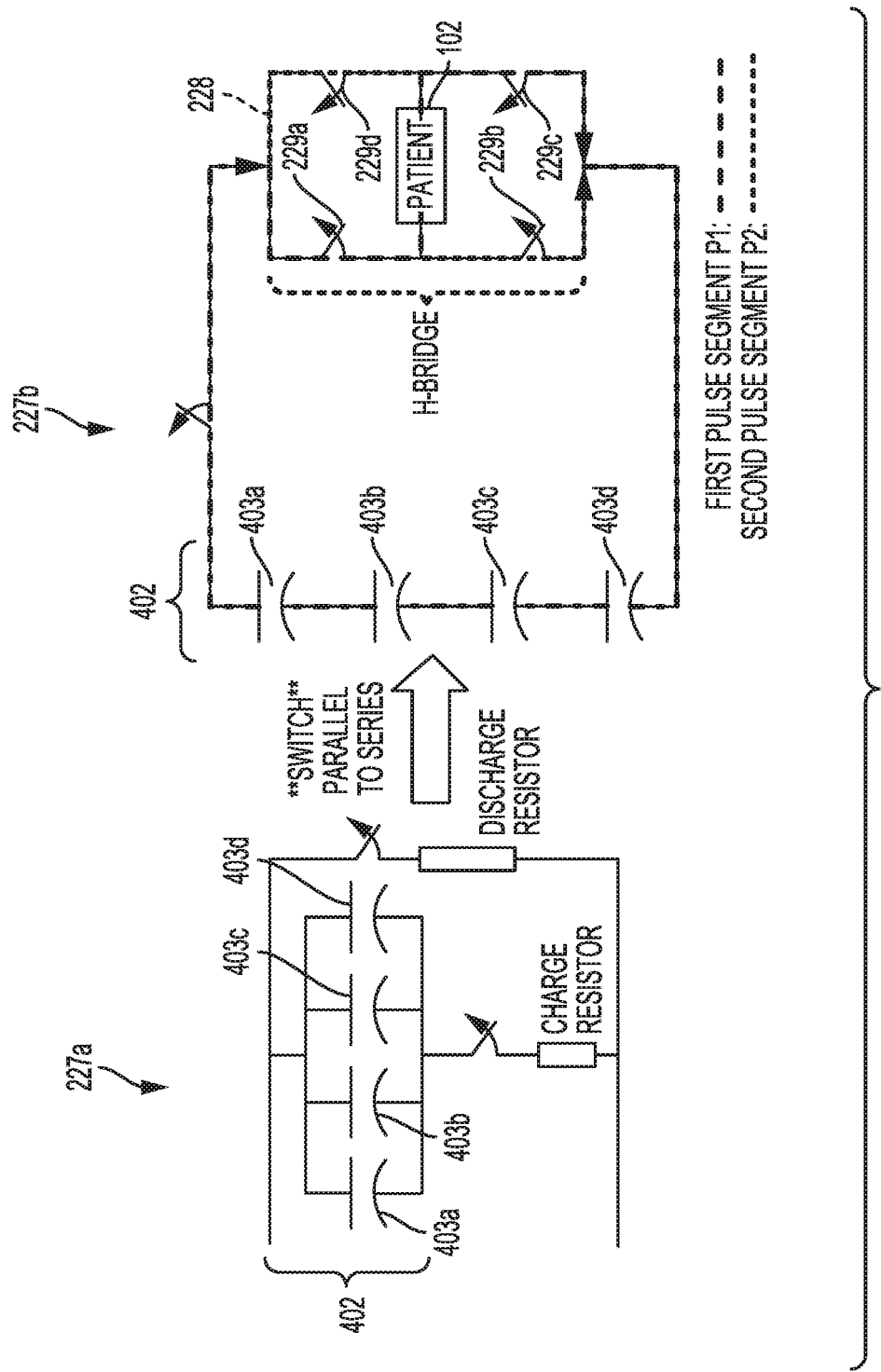
FIG. 3 depicts a schematic diagram of an embodiment of electrical components of a medical device controller of a patient-worn medical device.

As shown in the embodiment to FIG. 3, the H-bridge 228 is electrically coupled to a capacitor bank 402 including four capacitors 403a-d that are charged in parallel at a preparation phase 227a and discharged in series at a treatment phase 227b. In some implementations, the capacitor bank 402 can include more or fewer than four capacitors 403. During the treatment phase 227b, the H-bridge 228 applies a therapeutic pulse that causes current to flow through the body 102 of the patient in desired directions for desired durations. The H-bridge 228 includes H-bridge switches 229a-d that are opened and closed selectively by a switching transistor such as insulated gate bipolar transistors (IGBTs), silicon carbide field effect transistors (SiC FETs), metal-oxide semiconductor field effect transistors (MOSFETS), silicon-controlled rectifiers (SCRs), or other high current switching devices. Switching a pair of transistors to a closed position, for example switches 229a and 229c, enables current to flow in a first direction for first pulse segment P1. Opening switches 229a and 229c and closing switches 229b and 229d enables current to flow through the body 102 of the patient in a second pulse segment P2 directionally opposite the flow of the first pulse segment P1.

In embodiments, the device 100 further includes a garment 110 configured to be worn about the torso of the patient wherein at least one of the plurality of therapy electrodes 114 and the plurality of sensing electrodes 112 are disposed in the garment 110, like the garments described in U.S. Publication No. 2017/0143977, titled "GARMENTS FOR WEARABLE MEDICAL DEVICES," published on May 25, 2017, which is hereby incorporated herein by reference in its entirety. In implementations, the garment may be a belt, a sash, a vest, a holster, a shirt, a wrap-around garment, or a harness. In some implementations, the garment may be a one-shoulder garment configured to be worn about one shoulder and wrap around an upper torso of the patient. In these implementations, the garment 110 includes body-fitted portions for distributing components comfortably about the torso of the patient and other portions for aligning the plurality of sensing electrodes 112 and therapy electrodes 114 with clinically preferred positions for successful cardiac monitoring and treatment.

For example, the garment 110 may include a vest portion worn about an upper torso of the patient and a separate belt portion that is detachable from the vest. In this example, the sensing electrodes 112 and/or therapy electrodes 114 may be a permanent portion of the vest and the various modules (e.g., the therapy delivery circuit 202, the sensor interface 212, the processor 218, the network interface 206, and the user interface 208 described with regard to FIG. 2) may be removably or permanently attached to the belt portion. The belt may be detachable from the vest by, for example, a buckle, a hook-and-loop fastener, and/or a snap. In addition, one or more pieces of the garment may be designed to be inexpensive and/or disposable. For example, the vest portion of the garment may be disposable while the belt portion (including the various modules) may be laundered and redeployed to a new patient with a new vest portion.

Figure 4A:
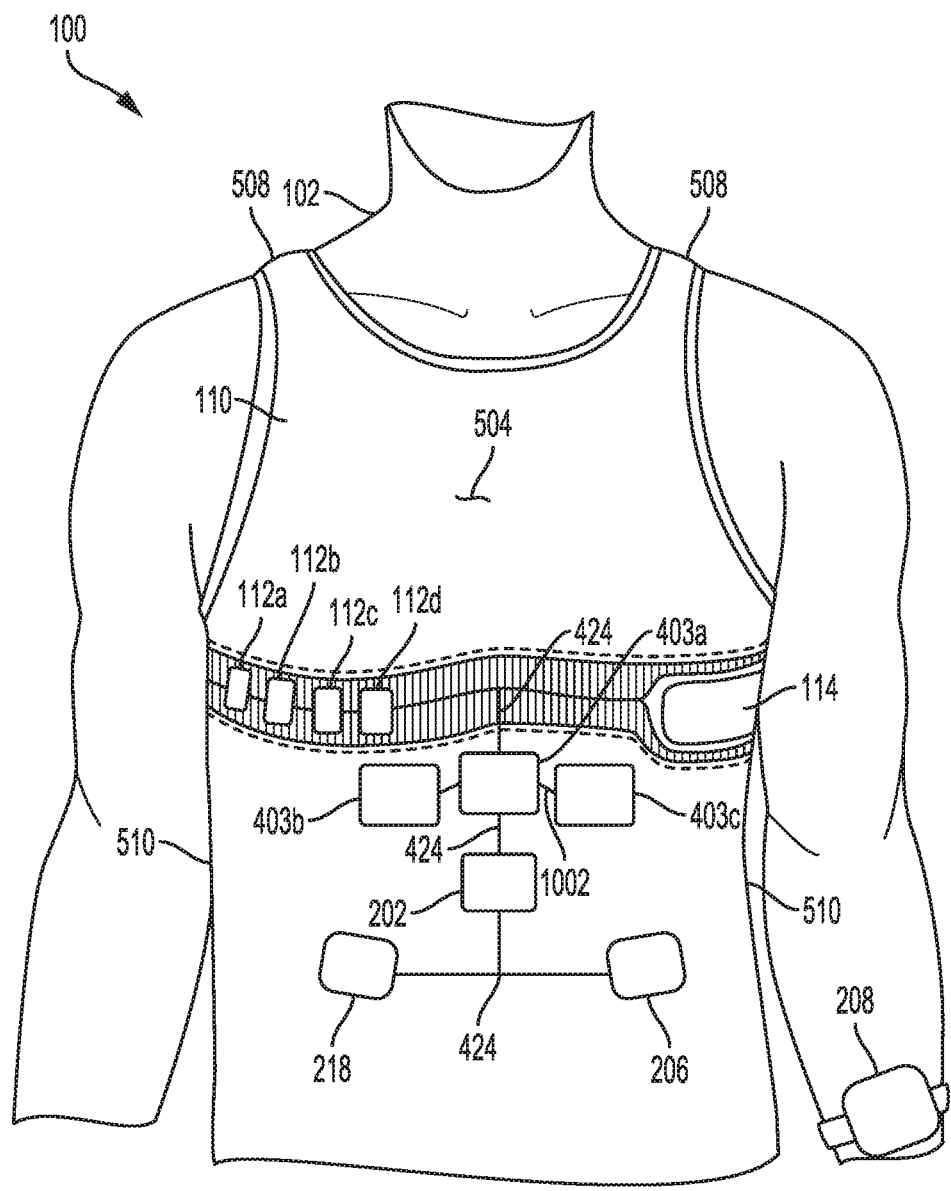
FIGS. 4A and 4B depict embodiments of a patient-worn medical device.
Figure 4B:
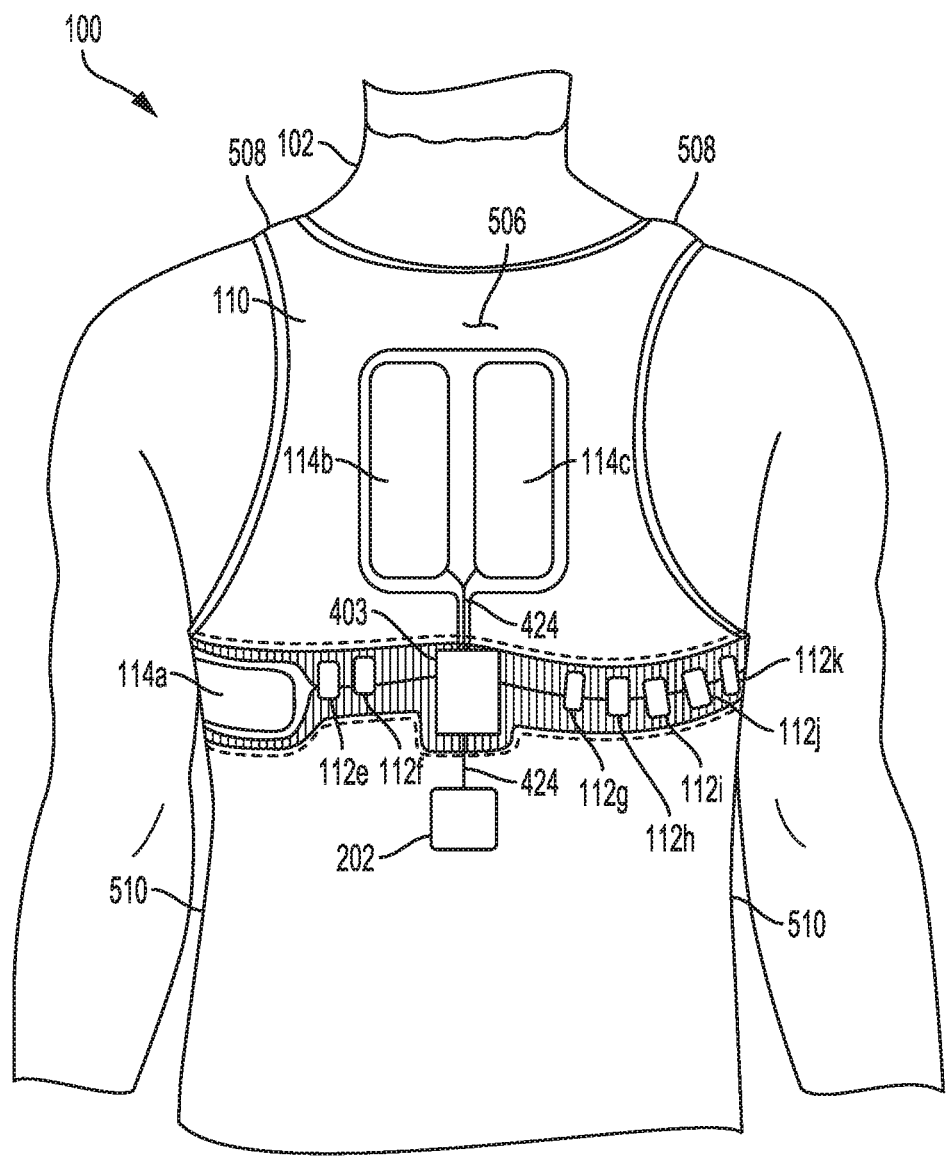

FIGS. 4A and 4B are front and rear views respectively of a patient wearing an example garment 110. As shown, in this example, the plurality of therapy electrodes 114 (e.g., 114a-c) and the plurality of sensing electrodes 112 (e.g., 112a-g) are permanent portions of the garment 110. For example, in implementations, the therapy electrodes 114 and sensing electrodes 112 are manufactured as integral components of the garment 110. For example, the therapy electrodes 114 and/or sensing electrodes 112 are formed within the warp and weft of the fabric. In some implementations, the therapy electrodes 114 and sensing electrodes 112 are supported between layers of the garment 110, for example, by stitching the layers around the edges of the therapy electrodes 114 or sensing electrodes 112. In implementations, the therapy electrodes 114 and the sensing electrodes 112 are formed partially or wholly of the warp and weft of the garment 110, including or spanning portions of conductive fabric forming one or more panels or swaths of the garment 110. In some implementations, the therapy electrodes 114 and sensing electrodes 112 are metallic plates or substrates that are formed as permanent portions of the garment 110. A metallic plate or substrate can be adhered to the fabric of the garment 110 by, for example, a polyurethane adhesive or a polymer dispersion adhesive such as a polyvinyl acetate (PVAc) based adhesive, or other such adhesive for securing metal or metal substrate to fabric. In examples, the sensing electrodes 112 are flexible, dry surface electrodes such as, for example, conductive polymer-coated nano-particle loaded polysiloxane electrodes mounted to the garment 110. In some examples, the sensing electrodes 112 are flexible, dry surface electrodes such as, for example silver coated conductive polymer foam soft electrodes mounted to the garment 110, or the sensing electrodes are screen printed onto the garment 110.

The garment 110 also includes the one or more capacitors 403 configured to store and deliver energy to the patient, and a therapy delivery circuit 202 to control the delivery of the energy. The plurality of capacitors 403 and the therapy delivery circuit 202 are each supported by the garment 110, for example, removably secured within the garment 110. In implementations, the one or more capacitors 403 are distributed about and secured within the garment 110, as described in detail subsequently. In some implementations, one or more components (e.g., modules) of the controller 120 (e.g. capacitors 403, therapy delivery circuit 202, processor 218) of the device 100 are distributed about and secured within the garment 110. In some examples, the plurality of capacitors 403 and the therapy delivery circuit 202 are each removably disposed on the garment 110 or within compartments of the garment. In embodiments, a plurality of modules (e.g., sensing electrodes 112, therapy electrodes 114, capacitors 403, therapy delivery circuit 202, processor 218, user interface 208) of the device 100 are supported by the garment 110. For example, the plurality of modules are distributed about and secured within the garment 110, as described in detail subsequently. For example, the plurality of modules are disposed on the garment 110. For example, the plurality of modules are removably disposed within compartments of the garment 110. For example, the plurality of modules are permanently affixed to the garment 110. For example, the plurality of modules are removably secured to the garment by a plurality of fasteners.

Figure 5A:
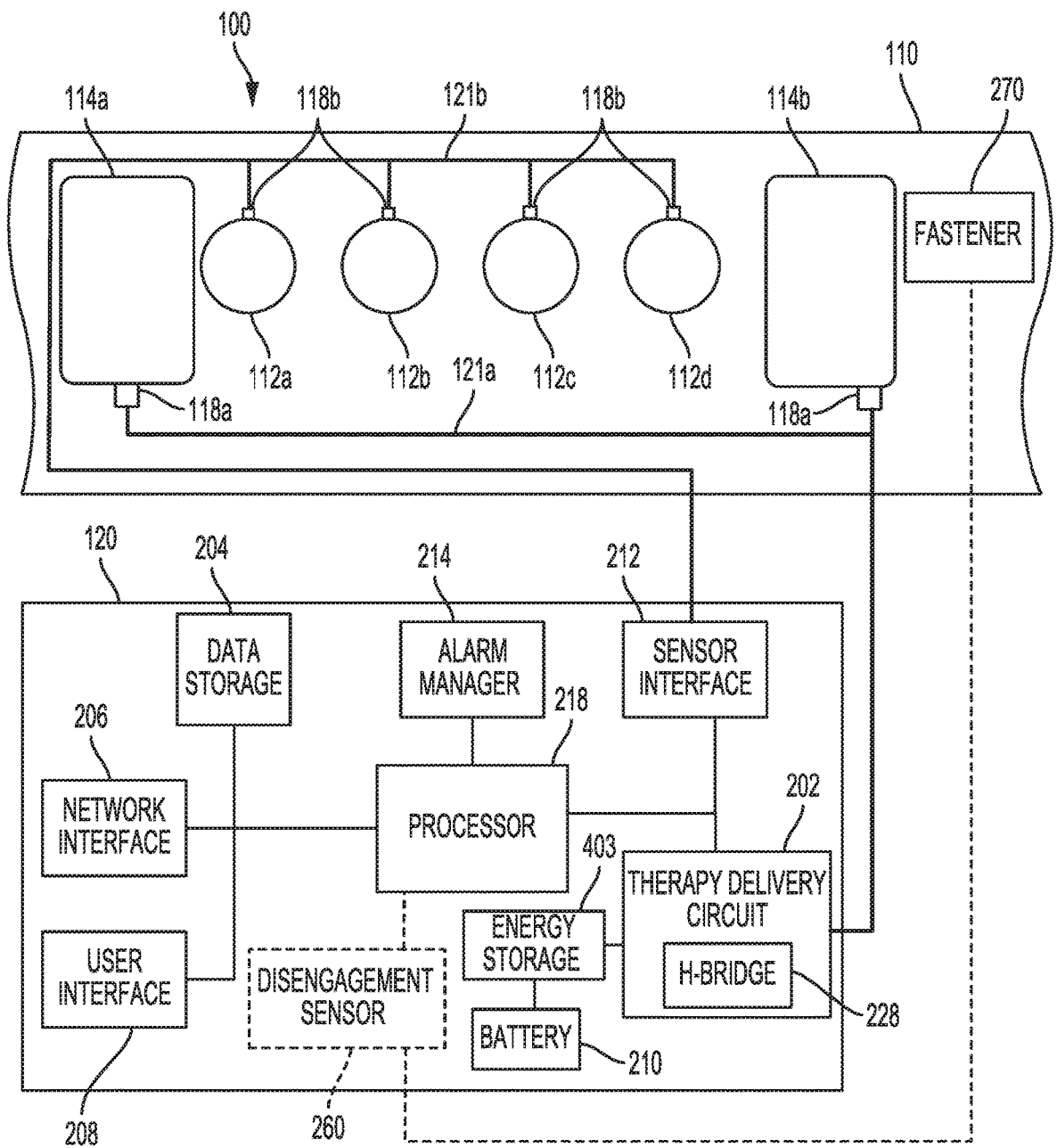
FIGS. 5A and 5B depict embodiments of schematics of electrical components of a patient-worn medical device.

FIG. 5A schematically depicts detachably coupled therapy electrodes 114a, 114b and sensing electrodes 112a-112d disposed within the garment 110. In implementations, the therapy electrodes 114 and the sensing electrodes 112 are electrically connected to the controller 120 and the therapy delivery circuit 202 by one or more wires 121a, 121b. The one or more wires 121a, 121b may be woven into the garment 110. The therapy electrodes 114 and sensing electrodes 112 are configured to electrically couple to one or more ends of the wires 121a, 121b upon attachment to the garment 110. Each of the therapy electrodes 114 and sensing electrodes 112 may connect electrically with the wires 121a, 121b upon coupling to an electrical connector 118a, 118b such as a snap or pin connector coupled to the wires 121a, 121b.

In some examples, the one or more wires 121a, 121b are integrated into the garment 110. In implementations, the one or more wires 121a, 121b can be supported between layers of the garment 110, for example, woven between at least two layers of fabric that together comprise the garment 110. In some implementations, the one or more wires 121a, 121b can be insulated in a cable routed discreetly in a hemline of the garment 110. In some examples, the one or more wires 121a, 121b can be stitched into one or more layers of the garment 110 or routed against an interior or exterior surface of the garment by one or more wire compartments or one or more retention loops or restraints. In some examples, the one or more wires 121a, 121b can be formed partially or wholly of the warp and weft of the garment 110, including or spanning portions of conductive fabric forming one or more panels or swaths of the garment 110.

In examples, the garment 110 includes receptacles, such as pockets or compartments, for receiving one or more of the therapy electrodes 114 and sensing electrodes 112. The receptacles contain therein one or more electrical connectors 118a, 118b for coupling the inserted therapy electrodes 114 and sensing electrodes 112 with the wires 121a, 121a.

Figure 41A:
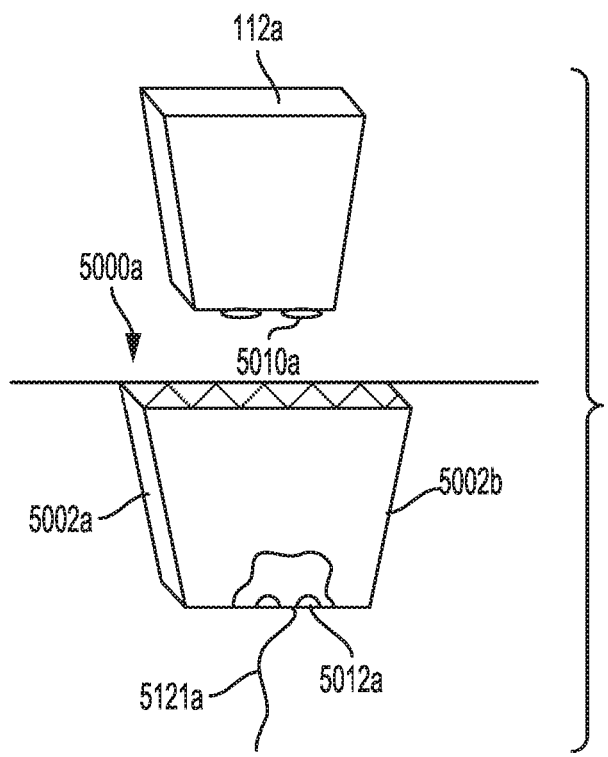
FIG. 41A depicts an embodiment of a poka-yoke sensor and receiving pocket of a patient-worn medical device.
Figure 41B:
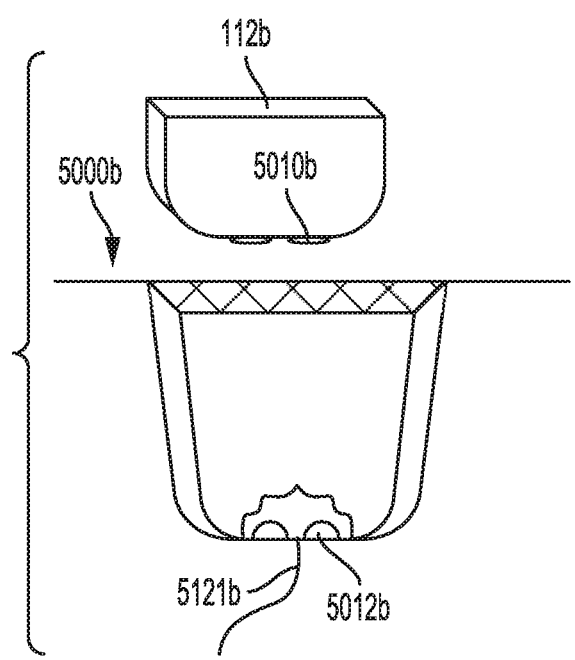
FIG. 41B depicts an embodiment of a poka-yoke sensor and receiving pocket of a patient-worn medical device

For example, the sensing or therapy electrodes and corresponding receptacles are each compatibly shaped and sized to allow the electrodes to fit in the receptacles in only one direction and orientation. To illustrate these features, FIGS. 41A and 41B show sensing electrodes 112a-b and receptacles 5000a-b that are all shaped and sized so that the sensing electrodes 112a-b fit in the receptacles 5000a-b in only one direction and orientation. For example, the receptacles 5000 may be made of a non-stretch material to form a cavity having sloped or tapered walls that align one or more electrical contacts 5010a-b on the sensing electrodes 112 with one or more receiving contacts 5012a-b disposed within the receptacle. For example, the receiving contacts 5012 are positioned at the bottom of the receptacle and are in communication with a wire 5121a-b in connection with the processor 218 described above with regard to FIG. 2. In embodiments, the receiving contacts 5012a, 5012b are spring loaded such that a small force, e.g. the gravitational force, applied to the sensing electrodes 112a, 112b forces the one or more electrical contacts 5010a-b into engagement with the one or more receiving contacts 5012a-b. Additional details on electrodes and receptacles that are shaped and sized to permit insertion in only a single direction or orientation can be found in U.S. Pat. No. 9,272,131, filed Oct. 24, 2014, and entitled "Flexible and/or Tapered Therapy Electrode".

In implementations, any one or more of the electrical components (e.g., sensing electrodes 112, therapy electrodes 114, the one or more capacitors 403, the therapy delivery circuit 202, the processor 218, and the network interface 206) may be sized and shaped for single-orientation insertion (e.g., single direction and rotation) into a receptacle having a similar size. The receiving receptacle or receptacles may be formed on or in the garment and may be sized to tautly hold the received electrical component. For example, the receiving receptacle or receptacles may be pockets formed of an elastomeric fabric or polymer that stretches to receive an electrical component and then contracts around the component to prevent dislodging. For example, the receiving receptacle or receptacles may be spandex pockets or thermoformed shells welded to the fabric.

In embodiments, the receptacle or receptacles are sized shaped to compliment the size and shape of the received electrical component. For example, the V-shaped sensing electrode 112A of FIG. 41A is inserted into a V-shaped receptacle 5000a. The side walls 5002a, 5002b of the receptacle 5000a are sloped to accommodate the sloped sidewalls of the sensing electrode 112a. The sensing electrode 112A thus inserts into the receptacle 5000a only in one orientation. The sloped sidewalls 5002a, 5002b of the receptacle 5000a guide the inserted sensing electrode 112a into a fully seated position such that the electrical contacts 5010a and receiving contacts 5012a mate blindly.

In some implementations, the receiving receptacle or receptacles additionally are formed such that each electrical component (e.g., the therapy electrodes) are inserted only in one direction and one rotational orientation. For example, the receiving receptacle or receptacles may be pockets formed so that the pocket narrows from front-to-back depth along the length of the pocket from the opening to the bottom of the receptacle so that a side cross section has approximately a right triangle shape. Similarly, the electrical component inserted into a narrowing pocket is flat on one side and sloped on an opposing side so that the pocket only receives the electrical component in a single rotational orientation. This ensures that components (e.g., the therapy electrodes) requiring a particular orientation relative to the skin of the patient are always inserted in a proper direction and orientation.

In some examples, the receiving receptacle or receptacles are shells formed of a polymer and sized and shaped to receive an electrical component in only one direction and orientation. The formed receptacle may include one or more features for accommodating orienting features on the surface of the electrical component, such a surface bevel or a protruding electrical connector.

Figure 5B:
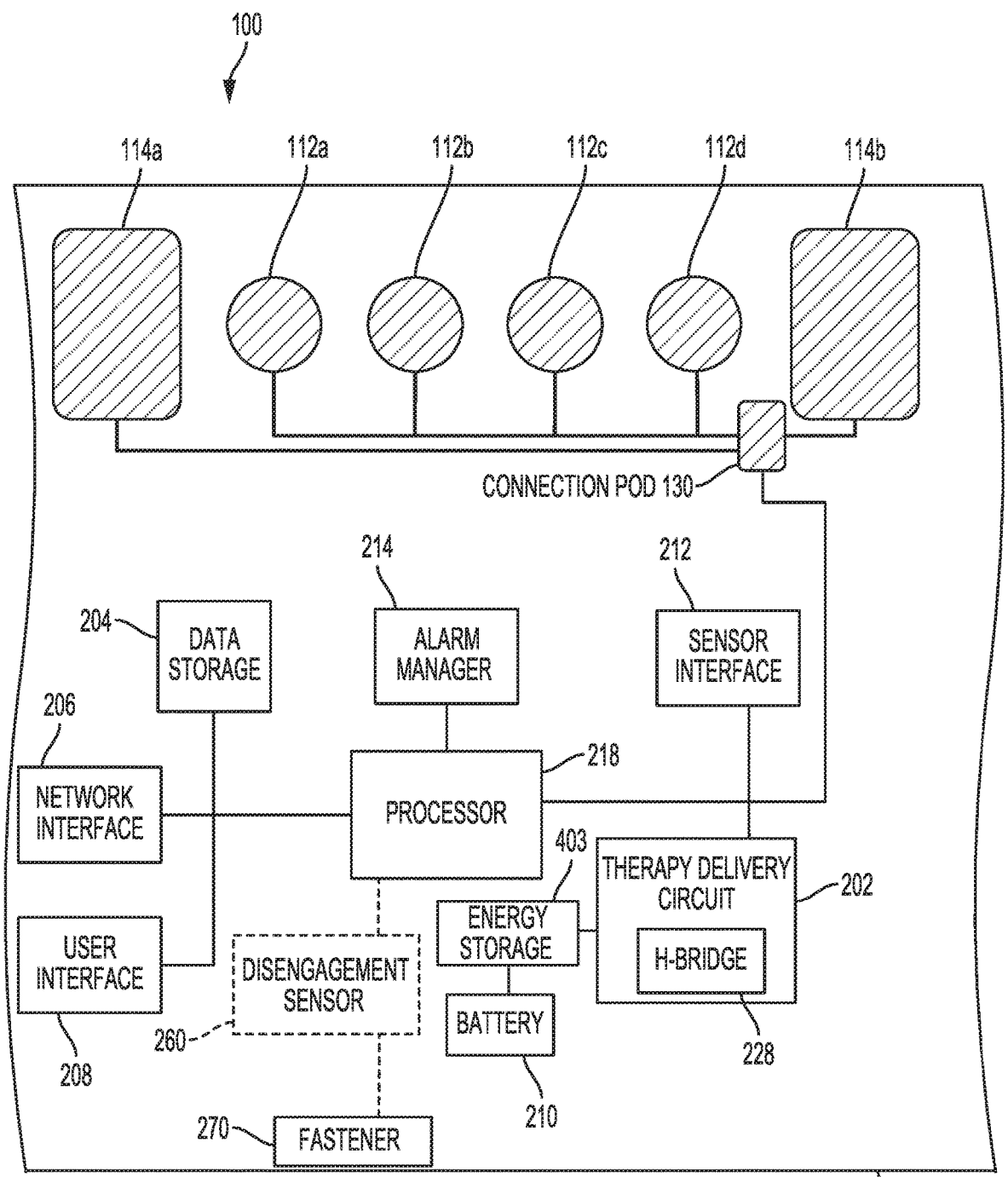

The examples relating to FIG. 5A describe electrical components received by receptacles integrated on or within the garment 110. FIG. 5B schematically depicts an embodiment of the plurality of therapy electrodes 114 (114a-b) and the plurality of sensing electrodes 112 (112a-d) that are a permanent portion of the garment 110. As indicated by the diagonal pattern, the therapy electrodes 114 and sensing electrodes 112 are manufactured as integral components of the garment 110. For example, the therapy electrodes 114 and/or the sensing electrodes 112 are formed of the warp and weft of the fabric. In certain implementations, the therapy electrodes 114 and the sensing electrodes 112 are formed from conductive fabric that is interwoven with non-conductive fibers of the fabric. In implementations, the therapy electrodes 114 and sensing electrodes 112 are formed as metallic plates or substrates that are adhered to the fabric of the garment 110. In FIG. 5B, the garment 110 of the patient-worn arrhythmia monitoring and treatment device 100 also includes one or more capacitors 403 configured to provide energy to the therapy delivery circuit 202, and the one or more capacitors 403 and the therapy delivery circuit 202 are supported by the garment 110. The one or more capacitors 403 are distributed about and integrated into the garment 110, as described in detail with regard to subsequently described embodiments.

As depicted in FIGS. 5A and 5B, embodiments of the device 100 also include additional features, such as a disengagement sensor 260 that indicates disengagement of a fastener 270 prior to the expiration of a prescribed duration of wear. In implementations, the disengagement sensor 260 is electrically coupled to the controller 120 and is configured to provide the indication of disengagement by generating a signal in response to mechanical disengagement of the fastener 270. Further detail regarding embodiments of disengagement sensors and indications of fastener disengagement are described subsequently with regard to FIGS. 38A through 40C.

Turning back to FIGS. 4A and 4B, the circuitry and components of a medical device controller (e.g., controller 120 as shown in FIG. 2) are distributed into one or more modules about the garment 110. The garment 110 includes a front portion 504 and a rear portion 506 that cover both an upper portion of the torso and a lower portion of the torso of the patient. As shown in FIG. 4A, the garment 110 includes shoulder portions 508 and side portions 510 that connect the front portion 504 to the rear portion 506 of the garment 110. The side portions 510 may extend from under the arms to near the waist line (e.g., to the bottom of the torso) in a similar fashion to a vest or a T-shirt. The shoulder portions 508 may be narrow strips of fabric constructed in a similar fashion to shoulder portions of vests. For example, the garment 110 may be comprised of stretchable, anti-microbial, breathable, and/or moisture-wicking fabric.

In some implementations, the ECG sensing electrodes 112 can be disposed at various predetermined locations, including different axial positions, around the body of the patient as shown and described in, for example, FIGS. 1A-F of U.S. Pat. No. 8,706,215, titled "WEARABLE AMBULATORY MEDICAL DEVICE WITH MULTIPLE SENSING ELECTRODES," issued on Apr. 22, 2014 (hereinafter the "'215 patent"), which is hereby incorporated herein by reference in its entirety. In some examples, the sensor interface 212 of the controller 120 in communication with the sensing electrodes 112 may include a multiplexer to control which ECG sensing electrode pairings are being monitored. For example, the sensor interface 212 may identify one or more optimal pairings (e.g., the pairings with the best signal quality) of sensing electrodes 112 and control a state of the multiplexer so as to receive ECG signals from the identified pairing(s). It is appreciated that the sensing electrodes 112 may be multiplexed manually. For example, the garment 110 may include multiple predetermined locations to receive ECG sensing electrodes 112 and a pairing may be selected by only connecting ECG sensing electrodes 112 at a subset of the predetermined locations.

One or more of the modules (e.g., the one or more capacitors 403, the therapy delivery circuit 202, the processor 218, and the network interface 206) of the controller 120 are distributed about the garment 110 so as to evenly distribute the weight of the medical device 100 on the left shoulder and the right shoulder of the patient. As illustrated in FIG. 4A, the user interface module 208 is implemented in a wrist-worn device such as a watch, bracelet, or fitness tracker. It is appreciated that other implementations of the user interface module 208 may be employed.

Figure 6:
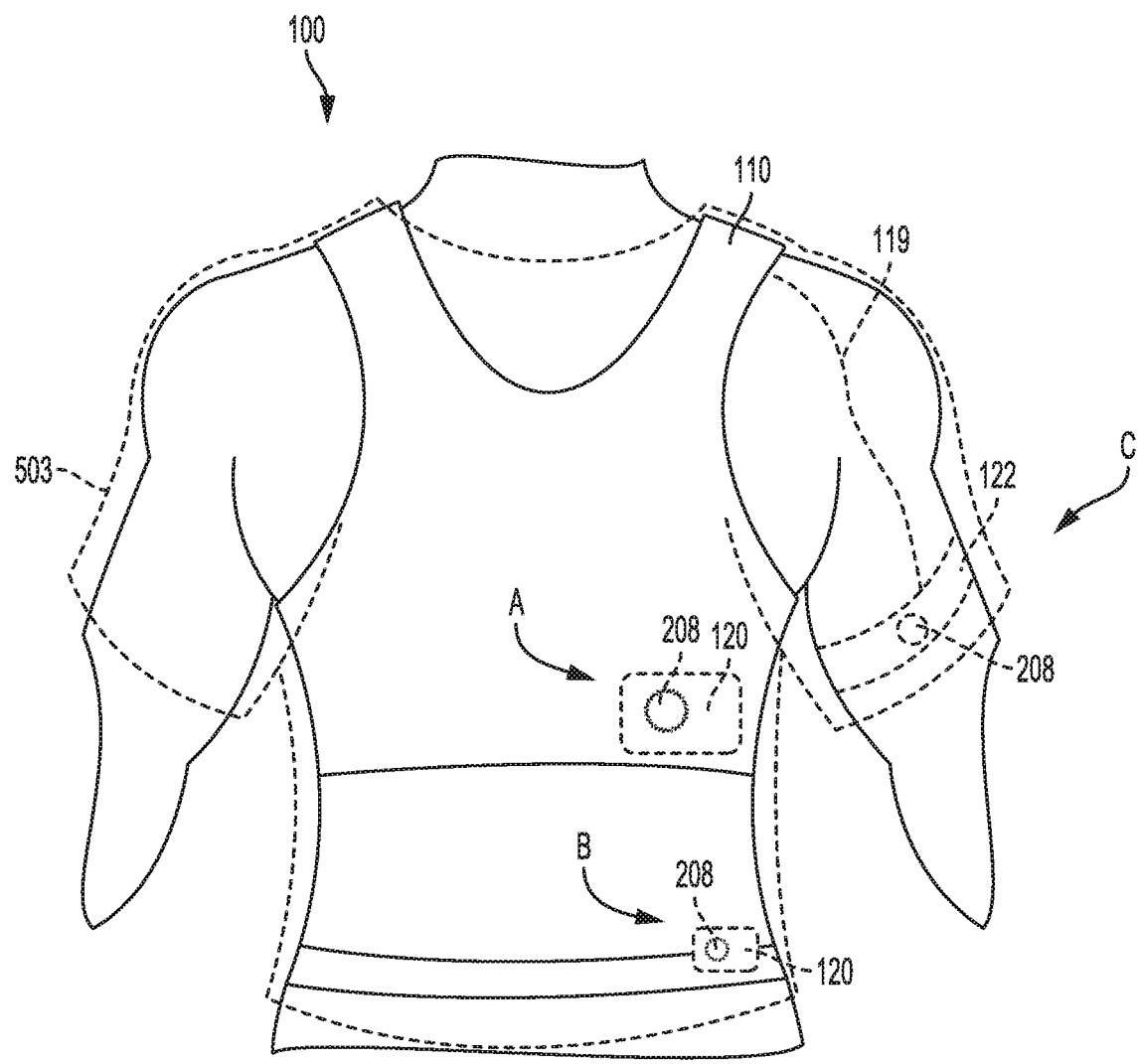
FIG. 6 depicts a front view of an embodiment of a patient worn medical device worn under clothing.

For example, as depicted in FIG. 6, the user interface 208 may be permanently disposed with or removably attached to the garment 110 and accessible by the patient. In implementations, the user interface 208 is integrated with the fabric of the garment 110, as indicated in position A. In implementations, the user interface 208 is in wired or wireless communication with the sensing electrodes 112 and therapy electrodes 114 and is located apart from the fabric of the garment 110. For example, the user interface may be integrated with a controller 120 and releasably attached to a waistband or belt by a spring loaded clip or a buckle, for example, as indicated in position B. In some implementations, the user interface 208 is in wired or wireless communication with the sensing electrodes 112 and therapy electrodes 114 and is located apart from the fabric of the garment 110 on a detachable and adjustable or self-adjusting arm band 122. In some examples, the arm band 122 is in electrical communication with the device 100 by a wire 119. In implementations, the user interface 208 is accessed while the patient is wearing clothing 503 over the device 100, and the user interface 208 is configured for facile manipulation through the fabric of clothing such that the user need not lift a shirt and expose their midriff or torso to interact with the device 100. For example, the user interface 208 may be a sizable button easily located by palpating over the clothing 503.

Returning to FIGS. 4A and 4B, the link between the network interface 206 and the user interface module 208 may be a wireless link while the link between the network interface 206 and the processor 218 may be a wired link (e.g., wired by a cable). Further, in examples, the wired links (if any) between the modules (e.g., the one or more capacitors 403, the therapy delivery circuit 202, the processor 218, and the network interface 206) include wires having different wire gauges. For example, the link 424 coupling the capacitors 403 to the therapy electrode 114 may support 2,500 volts and a 20,000 volt ESD while the link 424 between the processor 218 and the network interface 206 may have a lower voltage and ESD rating.

In some examples, one or more of the links 424 may be integrated into the garment 110. In some examples, one or more of the links 424 may be disposed between two layers of fabric of the garment 110. For example, the links 424 may be constructed from conductive thread, stranded wires, insulated cables (e.g., cables with a single wire, multiple wires, or stranded wires), and/or fiber optical cables integrated into the garment 110. In these examples, the garment 110 may be configured to receive each of the modules (e.g., the therapy electrodes 114, the sensing electrodes 112, the one or more capacitors 403, the therapy delivery circuit 202, the processor 218, and the network interface 206) and operably couple the modules to the links 424 integrated into the garment 110 when the modules are attached to the garment 110. In these examples, a user (e.g., a patient, a physician, a service representative, or a caregiver) can configure the wearable medical device 100 for monitoring or treatment based on the modules that are removably coupled to the garment 110. For example, the wearable medical device 100 may be configured as a wearable monitoring device by not installing the therapy electrodes 114. In this example, the treatment functionality of the wearable medical device 100 may be restored by attaching the therapy electrodes 114 to the garment 110.

Figure 7A:
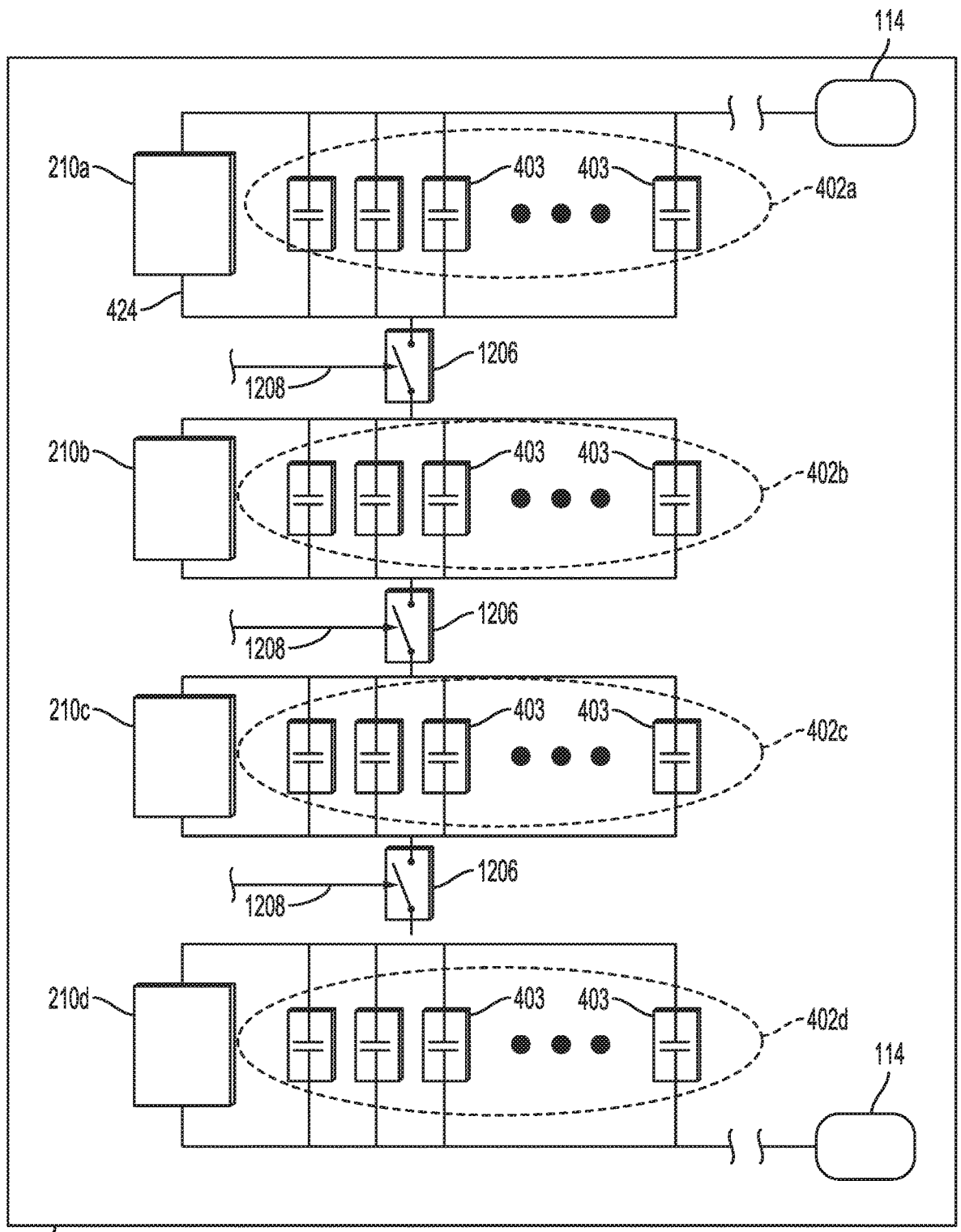
FIGS. 7A and 7B depict embodiments of an energy storage module of a patient-worn medical device.

In some examples, the plurality of capacitors 403 are integrated into the garment 110. For example, as illustrated in FIGS. 4A and 7A the charge capacity of the device 100 may be divided over a network of small capacitors 403 that are each integrated into separate regions of the garment 110 at various locations and coupled by conductive threading 424 or wiring. In some implementations, the garment 110 removably couples to a rechargeable battery 210 for powering the plurality of capacitors 403. In implementations, such as that of FIG. 4A, the plurality of capacitors 403a-403c may be integrated into various locations so as to evenly distribute weight across the garment 110. In some implementations, the plurality of capacitors 403 may be nested in a stacked configuration. For example, the plurality of capacitors 403 may be flat, film-type capacitors nested within a frame (not shown) integrated into the garment 110.

As noted above, a capacitor bank 402 comprises a plurality of capacitors 403 (e.g., capacitors 403a-d of FIG. 3). Energy storage is distributed over a plurality of relatively smaller capacitors 403 rather than one relatively larger capacitor having an energy storage capacity equal to that of the plurality of relatively smaller capacitors 403. The garment 110 advantageously carries an evenly distributed weight of the plurality of capacitors 403 rather than a localized weight of one relatively larger capacitor. This improves comfort during a long-term prescribed duration of wear. For example, the plurality of capacitors 403 may be flat-packed film capacitors each with a maximum thickness of between 1 mm and 40 mm, a capacitance under 250 g, and a breakdown voltage rating between 1300 and 2500 volts. Thereby, the capacitors 403 may be integrated into or attached to the garment 110 with a low profile and even weight distribution. This configuration prevents interfering with the mobility of the patient. It is appreciated that one or more batteries 210 may be similarly divided into a plurality of cells and integrated in an evenly spread weight distribution into the garment 110.

In implementations, the garment 110 includes a plurality of capacitor banks 402 each comprising a plurality of capacitors 403. For example, referring to FIG. 7A, the garment 110 includes a plurality of capacitor banks 402a-d each coupled to a charging battery 210a-210d. The capacitor banks 402a-d may be coupled to each other by one or more switches 1206 that control the connection between the capacitor banks 402a-d based on a control signal 1208 from, for example, the processor 218. Thereby, each of the capacitor banks 402a-d may be charged in parallel by a charging battery 210a-d (e.g., by opening the switch(es) 1206) and discharged in series with one another (e.g., by closing the switch(es) 1206). The number of capacitor banks 402 employed and/or the number of capacitors 403 in in each capacitor bank 402 may be altered based on the particular implementations. Further, a single charging battery 210 may be employed to charge multiple capacitor banks 402. For example, the four charging batteries 210a-d illustrated in FIG. 7A may be replaced by a single charging battery connected to all four of the capacitor banks 402a-d.

Figure 7B:
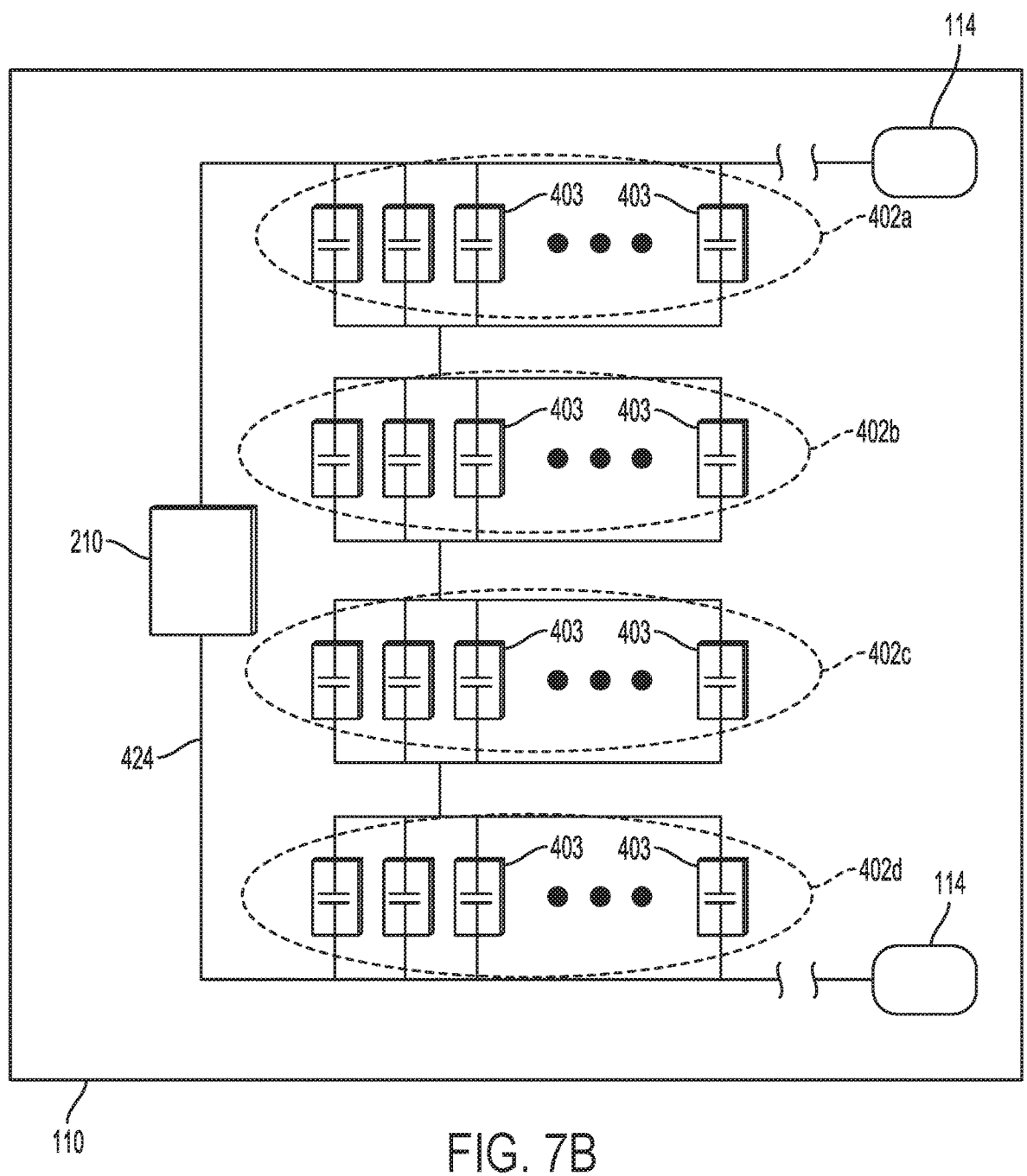

In some implementations, each capacitor bank 402a-402d may have a total capacitance rating that is divided up among the plurality of capacitors 403 connected in parallel. The total capacitance of a capacitor bank 402 may be equal to the sum of the capacitance of each of the plurality of capacitors 403 in the bank. Thereby, a target total capacitance rating for a capacitor bank 402 may be achieved by matching the sum total of the capacitances of the plurality of capacitors 403 in the bank 402 to the target. For example, the capacitor bank 402 may be designed to have a capacitance of 650 µF and the capacitor bank 402 may be constructed from 100 capacitors each with a capacitance of 6.5 µF (6.5 µF*100=650 µF). It is appreciated that other capacitor configurations may be employed including, for example, 130 capacitors each with a capacitance of 5 µF (5 µF*130=650 µF). Although FIGS. 7A and 7B illustrate four capacitor banks 402a-d each including a plurality of capacitors 403 where each capacitor bank may have a total capacitance of about 204 g, it is to be appreciated that some examples may include capacitor banks having different capacitances or capacitor banks having only a single capacitor each. For example, in one implementation a wearable arrhythmia monitoring and treatment device 100 may include four capacitors 403a-d each with a capacitance of about 500 µF.

Referring to FIG. 7B, the capacitors may be organized in a plurality of banks 402a-402d that are coupled in series without a switch 1206. In these implementations, the capacitor banks 402a-d are charged in series by a charging battery 210. Both charging and discharging the capacitor banks 402a-d in a series configuration may omit one or more components (e.g., the switch(es) 1206), but may require a higher charging voltage to store the same amount of energy relative to the parallel charging configuration illustrated in FIG. 7A.

Figure 8A:
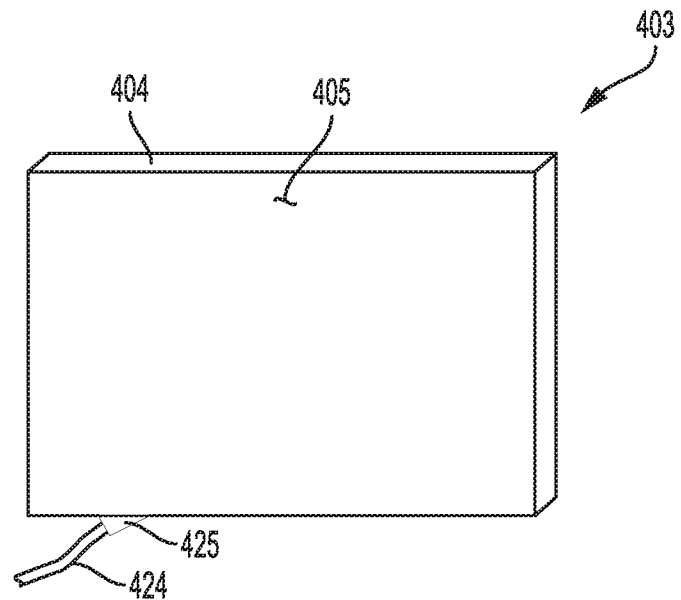
FIGS. 8A and 8B depict embodiments of a housing of one or more components of a patient-worn medical device.
Figure 8B:
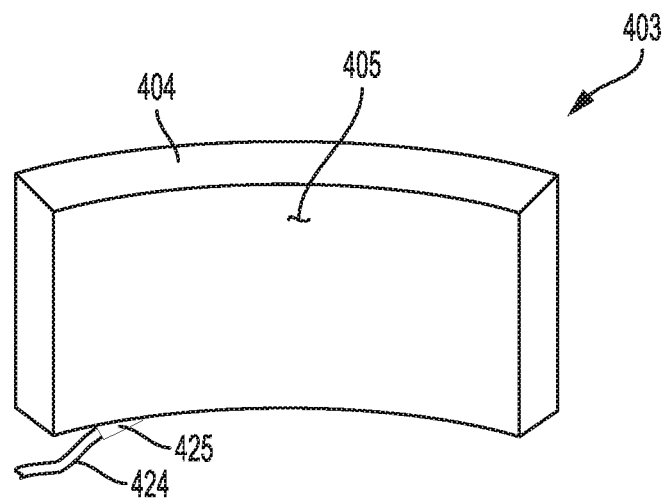

It is appreciated that the each capacitor of the plurality of capacitors 403 may be constructed in a variety of form factors. For example, each capacitor of the plurality of capacitors 403 may be include an encapsulating rigid enclosure 404 that is integrated into the garment 110. In implementations, the rigid enclosure 404 is contoured to conform to the curvature of the torso of the patient thereby resulting in a comfortable, mated fit when worn. For example, as shown in FIG. 8B, the enclosure 404 may be constructed from a rigid plastic including, for example, acrylonitrile butadiene styrene (ABS) plastic with a contoured surface 405 that conforms to the silhouette of a patient. For example, the contoured surface 904 can be configured to conform with a curvature of a portion of the patient's torso, such as lower portion of the torso, an upper anterior portion of the torso, upper posterior portion of the torso, one or more lateral portions of the torso. The particular shape of the contoured surface 405 may be pre-configured or uniquely designed for the patient. For example, various body size measurements may be obtained from the patient and a uniquely tailored enclosure 404 may be 3D printed from, for example, any suitable thermoplastic (e.g., ABS plastic).

Each capacitor of the plurality of capacitors 403 may also be custom-made capacitors created by packing a dielectric between two conductive plates and attaching conductive thread or wiring to the conducting plates. In some implementations, each capacitor of the plurality of capacitors 403 may be compact film pack capacitors that are directly integrated into the garment 110 and coupled by conductive thread or wiring. In some examples, the plurality of capacitors 403 may be integrated into other components of the wearable medical device 100. For example, the wearable medical device 100 may include one or more flat or contoured surfaces including, for example, a back-side of a gel deployment pack and/or a back-side of a therapy electrode 114. In these examples, a capacitor 403 may be integrated into these flat or contoured surfaces by placing a dielectric between two conductors.

In implementations, each capacitor of the plurality of capacitors 403 may be a small film capacitor with a maximum thickness of between 1 mm and 40 mm, a capacitance under 700 μF, and a breakdown voltage rating between 500 and 2500 volts. Thereby, the plurality of capacitors 403 may be integrated into a low profile garment 110 without interfering with the mobility of the patient. In some examples, at least one capacitor of the plurality of capacitors 403 is a film capacitor manufactured of tightly wound dielectric layers that are compressed and molded to match the silhouette of a patient. For example, the plurality of capacitors 403 can be configured to conform with a curvature of a portion of the patient's torso, such as lower portion of the torso, an upper anterior portion of the torso, upper posterior portion of the torso, one or more lateral portions of the torso. By shaping one or more of the plurality of capacitors 403 to accommodate on or more contoured regions of a patient's body 102, the capacitors 403 may be integrated into separate regions of the garment 110 to distribute weight evenly and/or to areas of least discomfort, and to minimize bulkiness associated with cylindrical or stacked capacitors.

In implementations, the contoured plurality of capacitors 403 are permanently affixed to the garment 110 and sandwiched between two pieces of fabric. In some examples, the contoured plurality of capacitors 403 water-resistant and/or coated with a water-resistant coating (e.g., an epoxy coating). Thereby, the garment 110 may be washed or worn in shower without damaging the electrical components that are permanently disposed into the garment 110. In implementations at least one of the plurality of sensing electrodes 112, the plurality of therapy electrodes 114, and one or more components of the controller 120 (e.g. capacitors 403, therapy delivery circuit 202, processor 218) are housed in one or more water resistant housings, or enclosures.

Example implementations of water-resistant housings protect against liquid ingress in one or more scenarios as set forth in Table 1 below.

TABLE 1

| Protection Against | Effective Against (e.g. shall not impact normal operation of the medical device as described herein) |
|---|---|
| Dripping water | Falling drops of dripping water on the medical device housing, e.g., water dripping on the housing at a rate 1 mm per minute for a period of around 10 minutes. |
| Spraying water | Spray of water falling on the medical device housing at any angle up to 60 degrees from vertical. |

TABLE 1-continued

| Protection Against | Effective Against (e.g. shall not impact normal operation of the medical device as described herein) |
|---|---|
| Splashing of water | Water splashing against the housing from any direction. |
| Water jets | Water projected by a nozzle (e.g., a nozzle of 6.3 mm diameter) against the housing from any direction |
| Powerful water jets | Water projected in powerful jets (e.g., a nozzle of 12.5 mm diameter spraying water at a pressure of 100 kPa at a distance of 3 m) against the housing from any direction |
| Immersion, up to 1 m depth | The housing is immersed in water at a depth of up to 1 meter. |
| Immersion, 1 m or more depth | The housing is immersed in water at a depth of 1 meter or more. |
| Powerful high temperature water jets | The housing is sprayed with a high pressure (e.g. 8-10 MPa), high temperature (e.g. 80 degrees Celsius) spray at close range. |

In some implementations, the housings of one or more components (e.g., the plurality of sensing electrodes 112, the plurality of therapy electrodes 114, and one or more components of the controller 120 (e.g. capacitors 403, therapy delivery circuit 202, processor 218)) of the device 100 are water-resistant housings having a predetermined ingress protection rating complying with one or more of the rating levels set forth in IEC standard 60529. The one or more water-resistant housings and the one or more components therein can be referred to as modules in some examples of the garment 110 having receiving compartments or receiving tracks.

The liquid Ingress Protection rating can be one or more of any level (e.g., levels 3 to 9) in which rating compliance tests are specified in the standard. For example, to have a liquid ingress protection rating level of six, a housing of an electrical component of the medical device 100 shall protect against ingress of water provided by a powerful water jet. The powerful water jet test requires that the housing is sprayed from all practicable directions with a stream of water from a test nozzle having a 12.5 mm diameter. Water sprays for 1 minute per square meter for a minimum of three minutes at a volume of 100 liters per minute (+/−5 percent) so that a core of the stream of water is a circle of approximately 120 mmm in diameter at a distance of 2.5 meters from the nozzle. For example, to have a rating level of 7, ingress of water shall not be possible when the housing is completely immersed in water at a depth between 0.15 m and 1 m so that the lowest point of a housing with a height less than 850 mm is located 1000 mm below the surface of the water and the highest point of a housing with a height less than 850 mm is located 150 mm below the surface of the water. The housing is immersed for a duration 30 minutes and the water temperature does not differ from that of the housing by more than 5K. Table 2 provides the rating levels and tests for liquid Ingress Protection in accordance with IEC standard 60529:

TABLE 2

| Rating Level | Degree of Protection | | Test conditions, see |
|---|---|---|---|
| | Brief Description | Definition | IEC 60529 section |
| 0 | Non-protected | — | |
| 1 | Protected against vertically falling water drops | Vertically falling drops shall have no harmful effects | 14.2.1 |
| 2 | Protected against vertically falling water drops when housing tilted up to 15 degrees | Vertically falling drops shall have no harmful effects when the housing is tilted at any angle up to 15 degrees on either side of the vertical | 14.2.2 |

TABLE 2-continued

| Rating Level | Degree of Protection | | Test conditions, see IEC 60529 section |
|---|---|---|---|
| | Brief Description | Definition | |
| 3 | Protected against spraying water | Water sprayed at an angle up to 60 degrees on either side of the vertical shall have no harmful effects | 14.2.3, including, for example, spraying water on the housing at 60 degrees from vertical at a water flow rate of 10 liters/min for at least 5 minutes |
| 4 | Protected against splashing water | Water splashed against the housing from any direction shall have no harmful effects | 14.2.4, including, for example, spraying water on the housing at 180 degrees from vertical at a water flow rate of 10 liters/min for at least 5 minutes |
| 5 | Protected against water jets | Water projected in jets against the housing from any direction shall have no harmful effects | 14.2.5, including, for example, spraying water from a 6.3 mm diameter nozzle at a distance of 2.5-3 m from the housing at a water flow rate of 12.5 liters/min for at least 3 minutes |
| 6 | Protected against powerful water jets | Water projected in powerful jets against the housing from any direction shall have no harmful effects | 14.2.6, including, for example, spraying water from a 12.5 mm diameter nozzle at a distance of 2.5-3 m from the housing at a water flow rate of 100 liters/min for at least 3 minutes |
| 7 | Protected against the effects of temporary immersion in water | Ingress of water in quantities causing harmful effects shall not be possible when the housing is temporarily immersed in water under standardized conditions of pressure and time | 14.2.7, including, for example, immersion for 30 min in a water tank such that the bottom of the housing is 1 m below the surface of the water and the top of the housing is 0.15 m below the surface of the water |
| 8 | Protected against the effects of continuous immersion in water | Ingress of water in quantities causing harmful effects shall not be possible when the housing is continuously immersed in water under conditions which shall be agreed between manufacturer and user but which are more severe than for numeral 7 | 14.2.8, including, for example, immersion in a water tank such that the bottom of the housing is greater than 1 m below the surface of the water and the top of the housing is greater than 0.15 m below the surface of the water |
| 9 | Protected against high pressure and temperature water jets | Water projected at high pressure and high temperature against the housing from any direction shall not have harmful effects | 14.2.9, including, for example, spraying water on the housing from all practical directions from a fan jet nozzle at a distance of 175 +/− 25 mm from the housing and spraying water at a flow rate of 15 liters/min for at least 3 min |

For example, a housing can be constructed to be water-resistant and tested for such in accordance with the IEC 60529 standard for Ingress Protection. For instance, the one or more housings of the device may be configured to have a rating of level 7, protecting against immersion in water, up to one meter for thirty minutes. This enables a patient to wear the device 100 in the bathtub or shower for uninterrupted, continuous use. For example, in implementations, such as the capacitors 403 of FIGS. 8A-B, the housing is a rigid enclosure 404 that includes a water tight grommet 425 where the link 424 (e.g., a wire) enters the rigid enclosure 404. This maintains the liquid Ingress Protection rating of level 7 of the rigid enclosure 404. In implementations, the one or more housings of the device 100 may be multiple coded, including two or more levels. For example, the a housing of the device 100 can maintain a liquid Ingress Protection level of 7, protecting against temporary immersion, and a liquid Ingress Protection level of 5, protecting against water jets.

In implementations, the patient-worn arrhythmia monitoring and treatment device 100 further includes a patient notification output. In response to detecting one or more treatable arrhythmia conditions, the controller 120 is configured to prompt the patient for a response by issuing the patient notification output, which may be an audible output, tactile output, visual output, or some combination of any and all of these types of notification outputs. In the absence of a response to the notification output from the patient, the controller 120 is configured to cause the therapy delivery circuit 202 to deliver the one or more therapeutic pulses to the patient.

Figure 9:
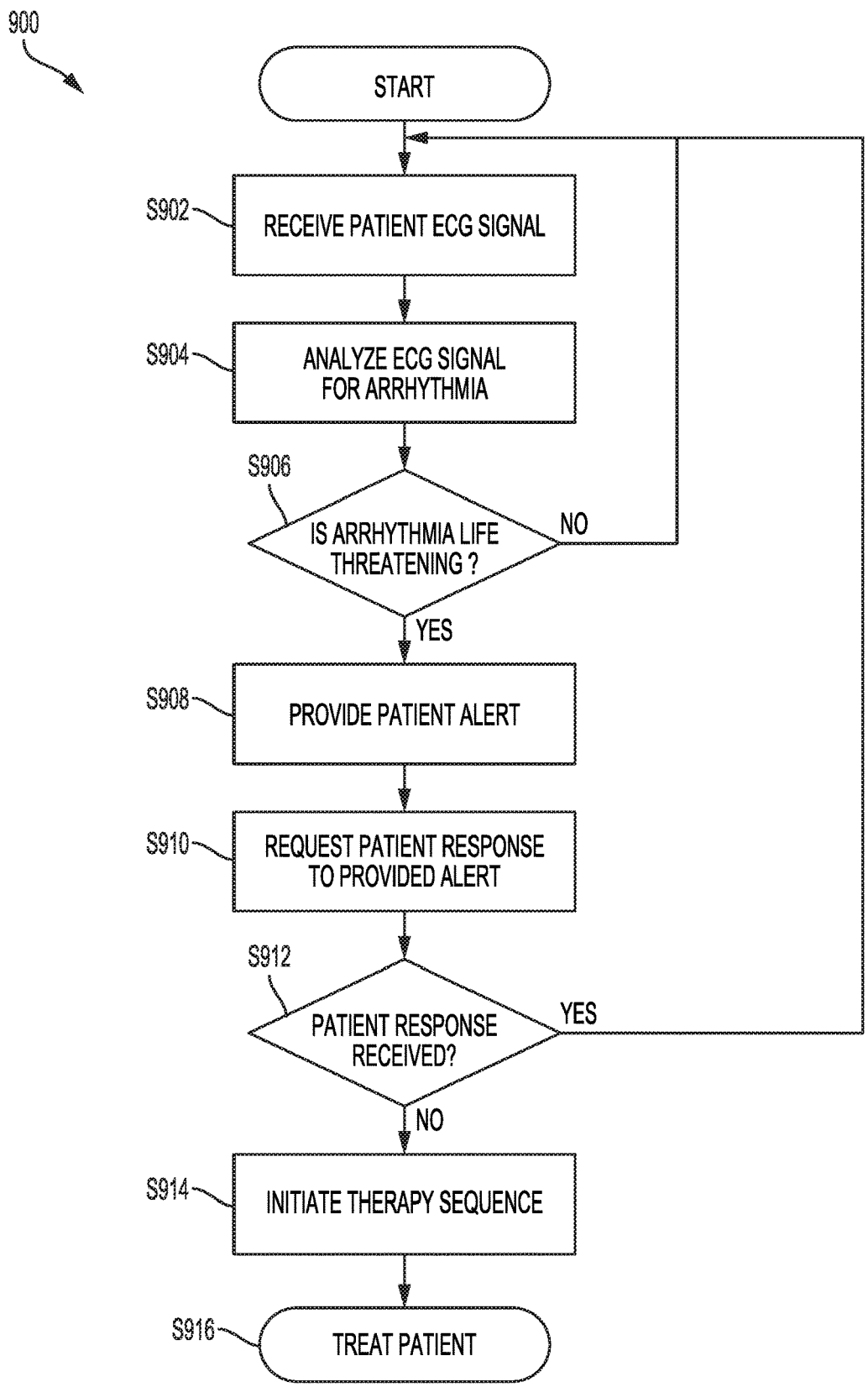
FIG. 9 is a flow diagram illustrating an embodiment of a medical device control process.

FIG. 9 depicts an example of a process 900 for determining whether to initiate a therapy sequence and apply a therapeutic pulse to the body of a patient. In implementations, the controller (e.g., controller 120), receives S902 a patient ECG signal from the pair or therapy electrodes and analyzes S904 the ECG signal for an arrhythmia condition. The controller determines S906 whether the arrhythmia is life threatening condition and requires treatment. If the arrhythmia is not life threatening, the controller can cause a portion of the ECG signal to be stored in memory for later analysis and continue to monitor the patient ECG signal. If the arrhythmia is life threatening, the controller provides S908 a patient notification output and requests S910 a patient response to the provided notification output. In implementations, the patient responds to an alert by interacting with a user interface (e.g., the user interface 208 of FIG. 2), which includes, for example, one or more buttons or touch screen interface buttons with haptic feedback. The response may be, for example, pressing one or more buttons in a particular sequence or for a particular duration. The controller determines S912 whether the patient response was received. If the patient responds to the notification output, the controller is notified that the patient is conscious and returns to a monitoring mode. If the patient is unconscious and unable to respond to the provided alert, the controller initiates S914 the therapy sequence and treats S916 the patient.

Figure 10:
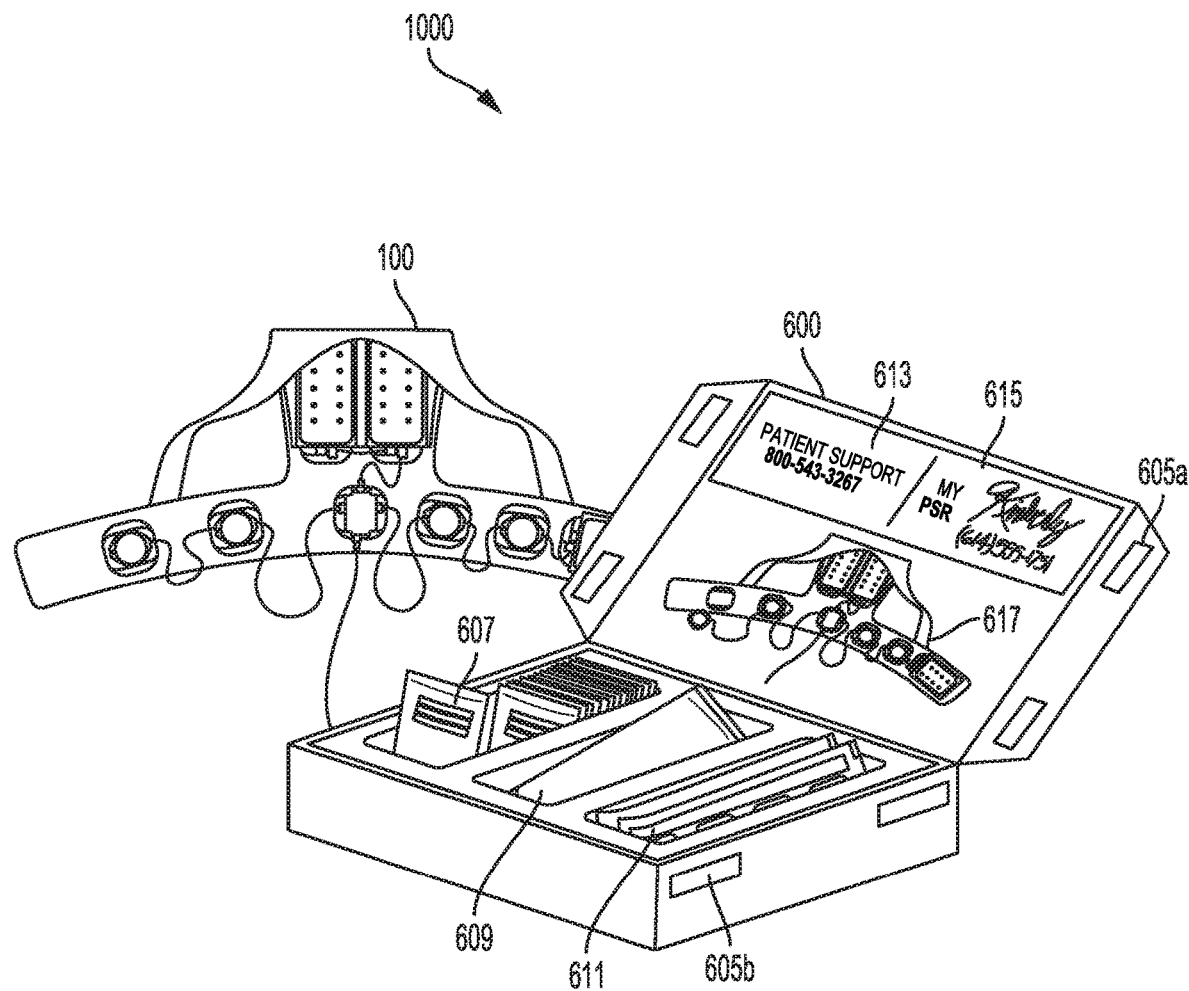
FIG. 10 depicts an embodiment of a kit including a patient-worn medical device.

Turning now to FIG. 10, the device 100 is prescribed by a physician for a duration of wear depending on the needs of the patient in the physician's medical judgment. In some embodiments, the device 100 is part of a kit 1000 provided to the patient in a hospital or doctor's office. In implementations, the kit 1000 includes a nondescript box 600 with an easily opened and closed lid. The fasteners 605 for opening and closing the lid are weak magnets, hook and loop strips, or other connectors disengaged without having to pinch, grasp, or apply significant force. The box 600 thus accommodates the needs and limitations of arthritic patients, for example. The box 600 can be used for storing and returning the device 100 after the prescribed duration. In implementations, the box 600 includes commonly-used supplies, including, for example, disposable cleaning pads 607 for cleaning the sensing electrodes 112 and the therapy electrodes 114, hypoallergenic skin care cream 609, defibrillation replacement gel packets 611, and hypoallergenic laundry detergent (not shown). In embodiments, the kit 1000 includes a second device 100 pre-assembled by the patient in the hospital or doctor's office. The box 600 further includes, in some examples, detailed information under the lid including a technical support number 613, an area 615 for a patient service representative (PSR) to record useful information, and an illustration 617 depicting assembly of the device 100 and providing at-home guidance during the prescribed duration.

Figure 11A:
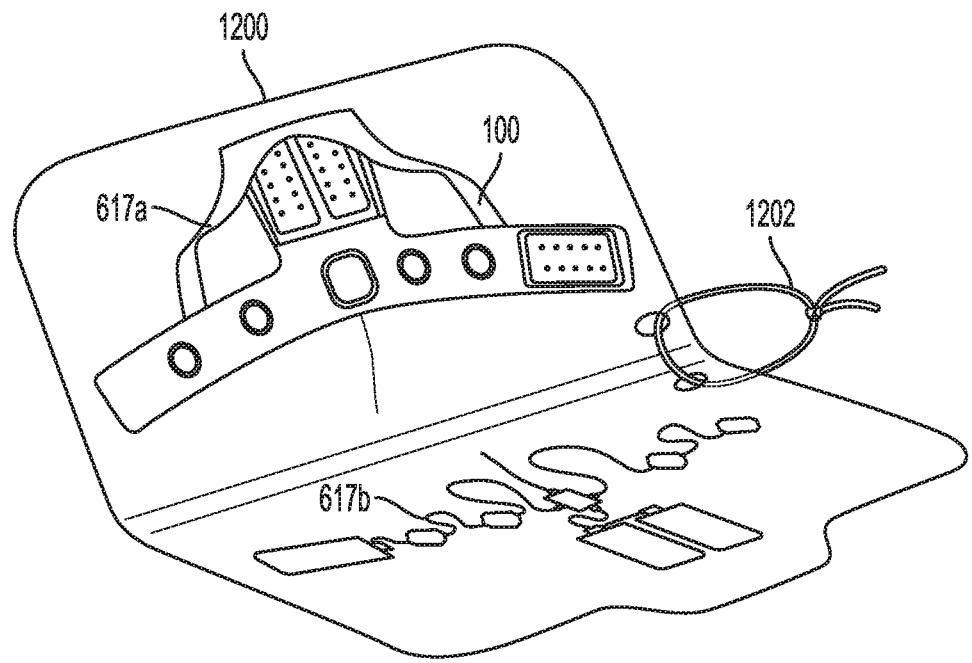
FIGS. 11A and 11B depict embodiments of assembly instructions for embodiments of a patient-worn medical device.
Figure 11B:
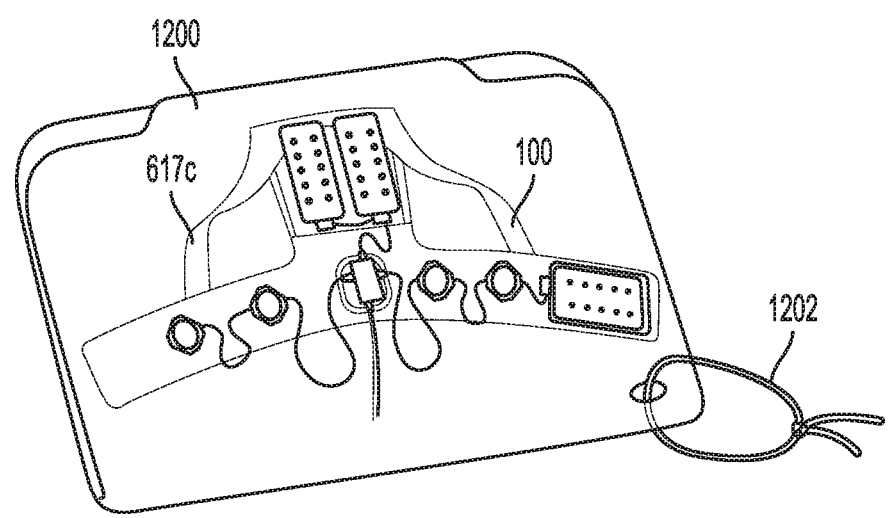

In some implementations, shown in FIGS. 11A and 11B, the patient returns home with a portable quick-start guide 1200 including assembly illustrations 617a, 617b, 617c, primary monitor functions and usage instructions, and common troubleshooting tips. In implementations, the quick start guide 1200 is small, thin, lightweight, discreet and easily grasped by arthritic patients. In some examples, the quick start guide 1200 includes a lanyard 1202. The quick start guide 1200 is configured to be hung by the lanyard 1202 or secured by a magnet in conspicuous locations, such as a medicine cabinet, a bedside table, or refrigerator.

Assembly and disassembly is improved with the assistance of the kit 1000 and the quick start guide 1200. Some implementations of the device 100 include additional features for assisting a patient with assembling the device. For example, the embodiment of the device 100 of FIG. 12A includes a plurality of soft-molded mounting pods 113a-h (collectively 113) configured to receive the plurality of sensing electrodes 112 and therapy electrodes 114 and any other components such as a connection pod 130, previously described with reference to FIGS. 1 and 5B. The soft-molded mounting pods 113 may be manufactured of a flexible thermoform material for holding an inserted element securely in tension on or within the garment 110. The mounting pods 113 may be sewn, glued, or welded to the garment 110 of the device 100. The mounting pods 113 include, in implementations, upper and lower lips 115a-d (collectively 115), under which portions of a component of the device 100, such as the sensing electrodes 112, are inserted. The upper and lower lips 115 securely retain a sensing electrode 112 until a patient applies a normal force to pull the electrode 112 free of the mounting pod 113. In certain embodiments, the sensing electrode 112 mounts to the soft-molded mounting pod 113 with a rotating motion (e.g., with a quarter-turn rotation) that fastens the sensing electrode 112 in place under the upper and lower lip 115. In implementations, the device 100 includes relational numbering for pairing electronic components (e.g., sensing electrodes 112, therapy electrodes 114, and connection pod 130, among others) with associated soft-molded mounting pods 113. The patient assembles the device 100 from left to right in numbered order. In some embodiments, hook and loop fasteners or magnets may be used to affix some or all of the electronic components to the device 100.

Figure 12A:
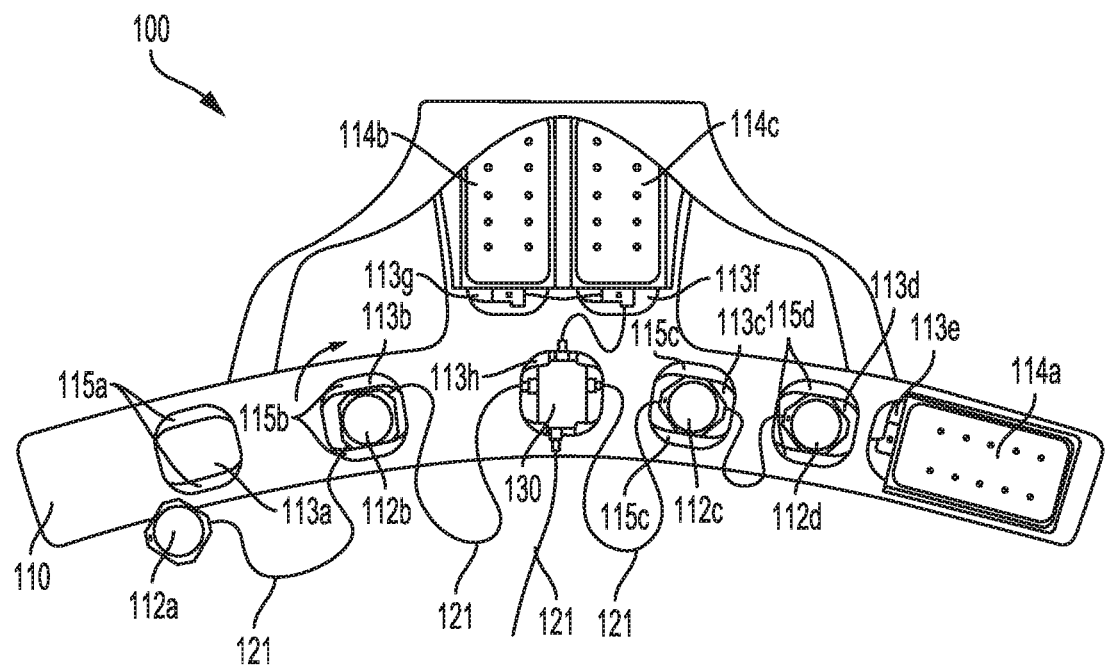
FIG. 12A depicts an embodiment of a patient-worn medical device having wires configured to contact the patient.

In some implementations, such as that of FIG. 12A, the wire 121 of the device 100 routes along the interior surface of the garment 110. In some implementations, such as that of FIG. 12B, the wire 121 routes along an exterior surface of the garment 110 or between layers of the garment 110 such that the wire 121 does not contact the skin of the patient. The sensing electrodes 112 and therapy electrodes 114 contact the skin of the patient through holes in the garment 110. This configuration of the wire 121 reduces friction against the skin of the patient and improves comfort, especially during prescribed durations of long-time wear.

Figure 13A:
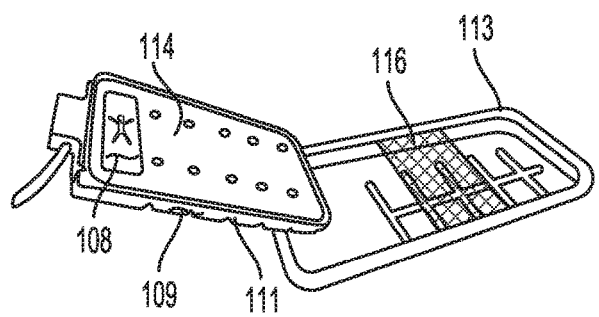
FIGS. 13A through 13D depict embodiments of a gel dispersal element of a patient-worn medical device.
Figure 13B:
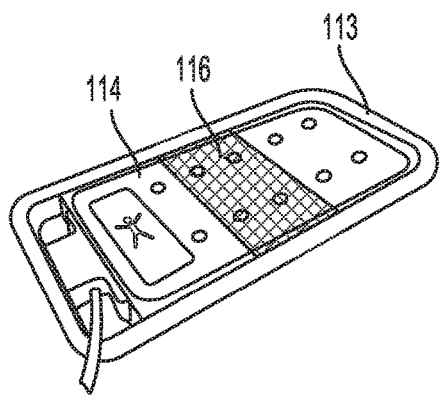
Figure 13C:
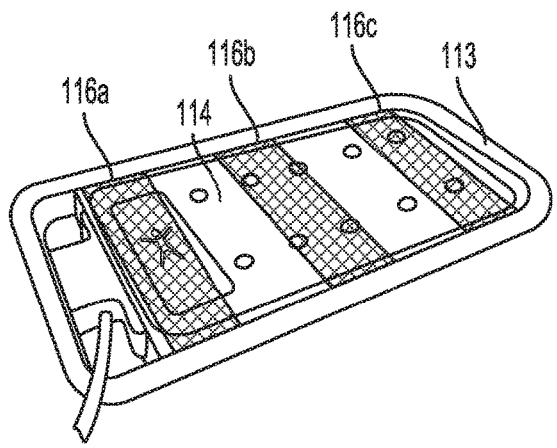
Figure 13D:
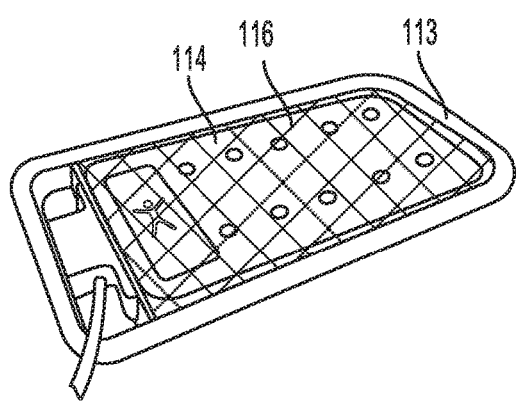

As indicated in the embodiments of FIGS. 13A-13D skin irritation is further reduced in embodiments by the inclusion of a gel dispersal element 116 having reduced surface area relative to the surface area of the therapy electrode 114. The therapy electrode 114 includes a conductive surface 108 and a foam backing 109. For example, the conductive surface 108 may be stainless steel, silver, or other metallic surface. The gel dispersal element 116 is a conductive element, and, in implementations, a wire mesh, that contacts the skin of the patient as a conduit for the therapy pulse being delivered via the conductive surface 108 of the therapy electrode 114. As shown in FIGS. 13A and 13B, the gel dispersal element 116 is, in some examples, a single strip under which the therapy electrode 114 is inserted when assembled into a mounting pod 113. The gel dispersal element 116 is a single strip covering approximately one third of the surface area of the therapy electrode 114. In examples, the strip may have other sizes, including, one half, one fourth, one fifth, one sixth, or two-thirds of the surface area of the therapy electrode 114. In some implementations, such as that of FIG. 13C, the gel dispersal element 116 includes a plurality of gel dispersal elements 116a-c, formed as narrow strips under which the therapy electrode 114 is inserted when assembled into a mounting pod. In implementations, the plurality of gel dispersal elements cover between one half and three fifths of the surface area of the therapy electrode 114. In some examples, such as that of FIG. 13D, the gel dispersal element 116 is an open weave layer formed from metallic wires or threads and spans the entire surface area of the therapy electrode but with about 50 to 75 percent of the surface area of the therapy electrode remaining exposed or uncovered by the gel dispersal element.

As described previously with regard to FIG. 1, in some implementations, gel deployment modules may be implemented as gel deployment packs and include at least a portion of the gel deployment circuitry along with one or more gel reservoirs within the gel deployment pack. In such implementations, the gel deployment pack, including the one or more gel reservoirs and associated gel deployment circuitry may be removable and/or replaceable. In some examples, such as those shown in FIGS. 13A through 13D, the gel deployment pack, including the one or more gel reservoirs 111 and associated gel deployment circuitry, and the therapy electrode 114 can be integrated into a therapy electrode assembly that can be removed and replaced as a single unit either after use, or if damaged or broken.

Figure 14A:
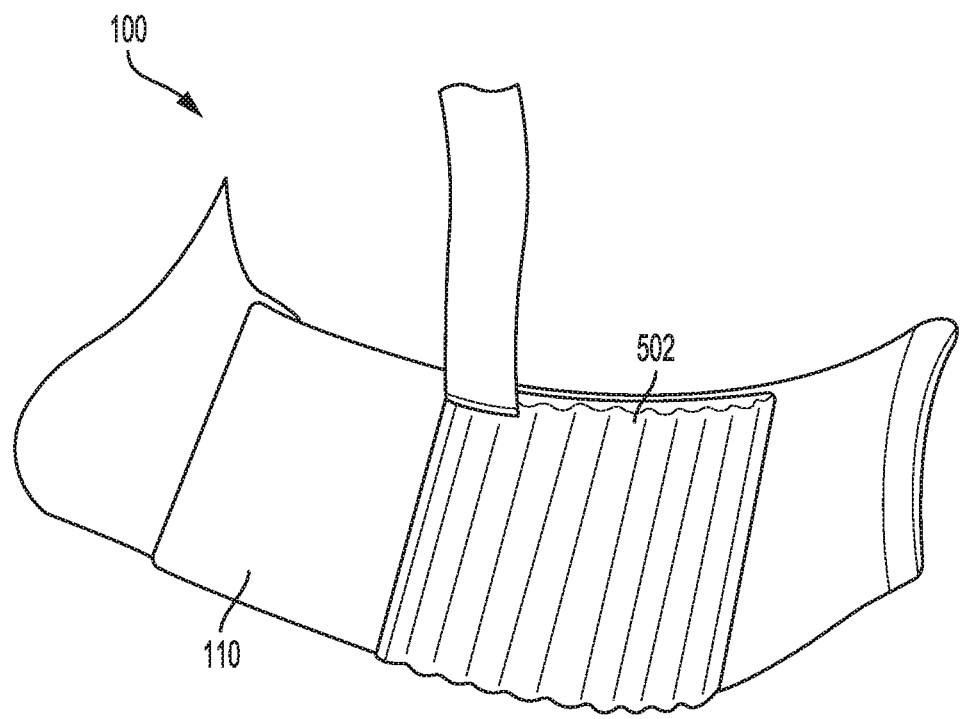
FIGS. 14A and 14B depict an embodiment of a structurally reinforced portion of a patient-worn medical device.
Figure 14B:
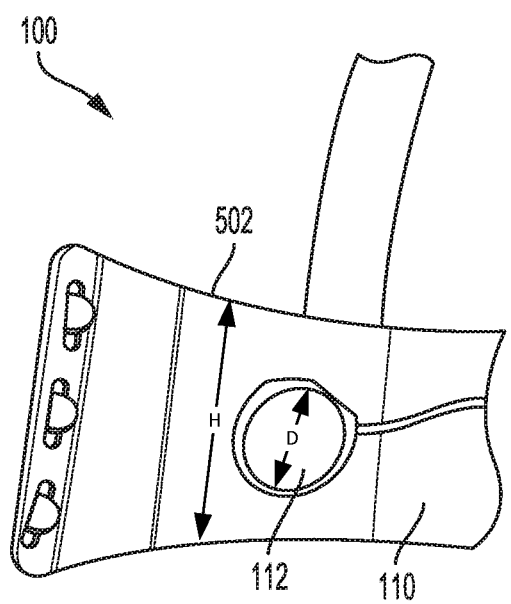

Patient comfort is addressed by additional features of embodiments that prevent sensing electrodes 112 from flipping during the prescribed duration of wear. FIGS. 14A and 14B show a portion of a garment 110 including at least one integrated vertically corrugated support zone, e.g., a corrugated stiffener panel 502, at the location of one of the sensing electrodes 112. In embodiments, the vertically corrugated stiffener panel 502 forms an entire section of the garment 110, and in other embodiments, as shown in FIGS. 14A and 14B, the vertically corrugated stiffener panel 502 forms a layer of a portion of the garment 110. In the embodiment of FIGS. 14A and 14B, the corrugated stiffener panel is attached to the outer surface of the garment 110 and the sensing electrode 112 is mounted to an opposing, smooth inner surface of the garment 110. In implementations, the device 100 includes one or more support zones including, for example, a corrugated stiffener panel 502, in proximity to one or more of the plurality of sensing electrodes 112. In implementations, the corrugated stiffener panel 502 is held in compression against the body 102 of the patient to resist rotation or pulling away from the torso. In implementations, a ratio of the height H of the stiffener panel 502 relative to the widest dimension (e.g., the diameter D of a round electrode) of the sensing electrode 112 is in a range of about 2:1 to 7:1 (e.g., 4:1.5, 4.5:2, 4.7:2, 5:1.75, 5:2, 5:2.25, 6:1, 6:2, 7:1). For example, the height H of the stiffener panel can be 3 to 5 inches tall and the sensing electrode 112 can be a round electrode having a diameter D of 1.5 inches. In some implementations, the stiffener panel 502 is corrugated, and the corrugation flute has a Young's modulus of 600-700 MPa under a load of greater than 250N. In implementations, the corrugated stiffener panel 502 is flexible without deforming and flexes to accommodate anatomical compliance. Although the implementation of FIGS. 14A and 14B shows a sensing electrode 112 mounted to an interior surface of the garment 110, the corrugated stiffener panel 502 additionally or alternatively applies to embodiments in which the plurality of sensing electrodes 112 and the wire 121 are mounted to an outer surface of the garment 110. For example, in implementations, the corrugated stiffener panel 502 is included between inner and outer layers of the garment 110 to provide stability and a smooth surface for externally mounting a sensing electrode 112. Although the stiffener panel 502 is described with regard to a corrugated embodiment, other embodiments are contemplated. For example, the stiffener panel 502 could be knitted compression panel or a thermally bonded compression panel having no corrugation, but resisting stretching and twisting while having a ratio the height H of the stiffener panel 502 relative to the widest dimension (e.g., the diameter D of a round electrode) of the sensing electrode 112 in a range of about 2:1 to 7:1 (e.g., 4:1.5, 4.5:2, 4.7:2, 5:1.75, 5:2, 5:2.25, 6:1, 6:2, 7:1).

Figure 12B:
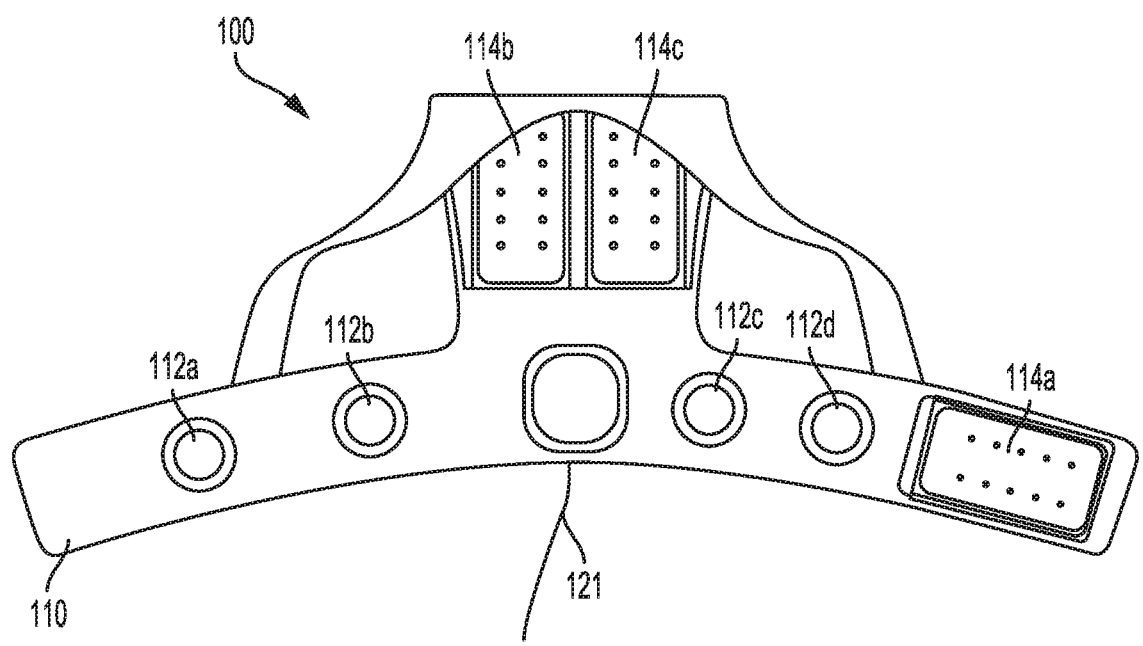
FIG. 12B depicts an embodiment of a patient-worn medical device having no wires configured to contact the patient.

As mentioned with regard to FIG. 12B, the wire 121, or wires, connecting the plurality of sensing electrodes 112, the plurality of therapy electrodes 114, the optional connection pod 130, and the controller 120, may be mounted to an exterior surface of a garment 110 or between layers of a garment 110 of embodiments of the device 100. Concealing the wire 121 and/or routing the wire 121 elsewhere other than against the skin of the patient improves comfort during the prescribed duration of wear. In implementations, the garment 110 includes one or more wire compartments and/or retention loops for routing one or more wire or wires 121 against the outer surface of the garment, and the one or more wires 121 are configured to couple to at least two of the controller 120, the plurality of ECG sensing electrodes 112, the plurality of therapy electrodes 114, the therapy delivery circuit 202, and a disengagement sensor 260.

As shown in the embodiment of FIGS. 15A through 15C, the device 100 includes externally mounted electrical components (e.g., the plurality of sensing electrodes 112 and plurality of therapy electrodes 114) connected by a wire 121, or wires, routed on an outer surface of the garment 110, away from the skin of the patient. The electrical components (e.g., the plurality of sensing electrodes 112 and plurality of therapy electrodes 114) supported by the garment 110 and the wire 121 are therefore not held in compression against the skin of the patient, and this configuration enhances patient comfort. In implementations, the garment includes apertures in at least a portion of the plurality of resealable compartments for providing direct contact between the skin of the patient and a plurality of ECG sensing electrodes configured for insertion into the plurality of resealable compartments. For example, in the implementation of FIGS. 15A through 15C, the sensing electrode 112, for example an ECG sensing electrode, is configured to be held in a resealable compartment 152 and pressed through an aperture 105, or opening, in the garment 110 to contact the skin of the patient. The wire 121 is routed within the resealable compartment 152, and the compartment 152 seals the wire and the sensing electrodes 112 in place with a plurality of closures 104 such as snaps, hook and loop fasteners, magnets, buttons, zippers, etc. In implementations, such as that shown in FIG. 15C, the sensing electrode 112 includes a square back housing 1108 that provides grasp points at the corners for inserting and anchoring the sensing electrode 112 in the compartment 152.

Similarly, as shown FIGS. 15A and 15B, the therapy electrodes are inserted into a resealable compartment 153. The device 100 may be assembled by laying the garment 110 flat on a surface with the resealable compartments 152, 153 fully opened. The patient may then assemble the therapy electrodes 114 and sensing electrodes 112 into the garment 110 and then reseal the resealable compartments 152, 153 with the plurality of closures 104.

The embodiments, such as those of FIGS. 16A through 16K, show examples of attaching the sensing electrodes 112 to the garment 110. Each of figures of FIGS. 16A through 16K shows a portion of a devices 100 that includes a plurality of button holes in the garment 110 configured to receive and retain a plurality of button-style sensing electrodes 112.

Figure 16A:
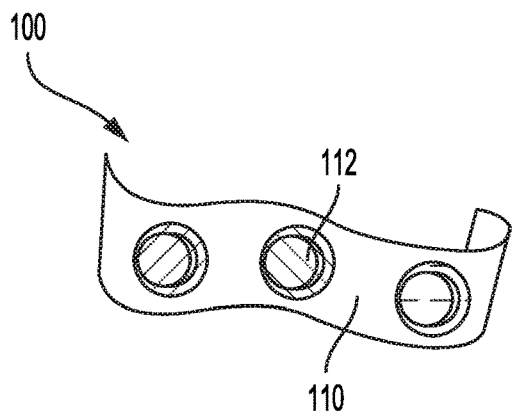
FIG. 16A depicts an embodiment of a patient-worn medical device.
Figure 16B:
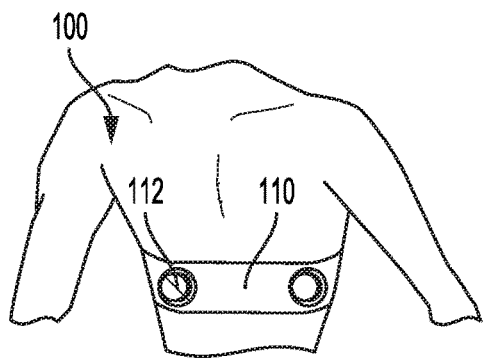
FIG. 16B depicts an example of a patient wearing the device of FIG. 16A.

FIG. 16A shows an example device 100 having a belt-style garment 110 and button-style sensing electrodes 112 retained therein. FIG. 16B shows the device of FIG. 16A retained on the torso of a patient. In some implementations, the garment 110 is an adhesive-assist garment that helps bear the load of an adhesive applied to the sensing electrodes 112. The adhesive-assist garment 110 may be held in tension by a fastener and/or an elastic material comprising the garment 110. This prolongs adhesion of the sensing electrodes 112 and reduces tension-induced irritation across the adhesive-skin interface.

Figure 16C:
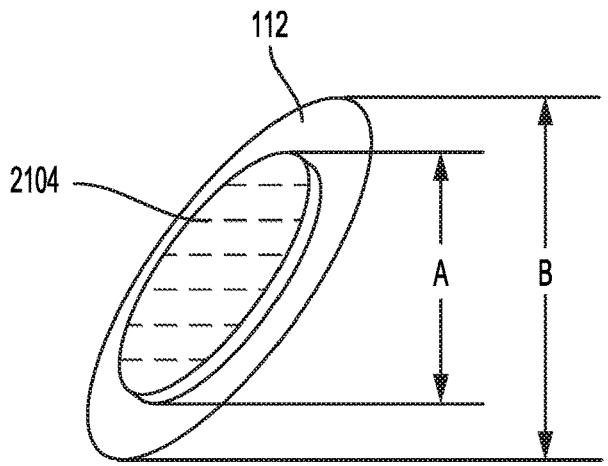
FIG. 16C depicts a perspective view of an embodiment of a sensor for use with the embodiment of the patient-worn medical device of FIGS. 16A and 16B.

FIG. 16C shows a perspective view of a wire interface 2104 of the electrode 112. The wire interface 2104 is directed away from the skin of the patient and is permanently or selectively coupled with a wire for electrical communication with other components of the device 100. The wire interface 2104 of the electrode 112 may be color coded to assist with identifying a similarly color coded button hole on the garment 110. This is particularly helpful when a plurality of sensing electrodes 112 are attached to wire prior to engaging the garment 110 such that the order of assembly is critical to prevent wire bunching or tangling or flipping of the sensing electrodes 112

Figure 16D:
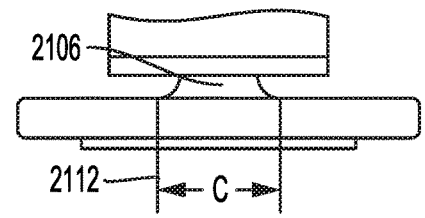
FIG. 16D depicts a side view the embodiment of the sensor of FIG. 16C.

FIG. 16D shows a side view of the electrode of FIG. 16C. In some examples, the button holes (e.g., button holes 2105 of FIG. 16F) are elasticized to retain a neck portion 2106, of the sensing electrode 112 therein.

Figure 16E:
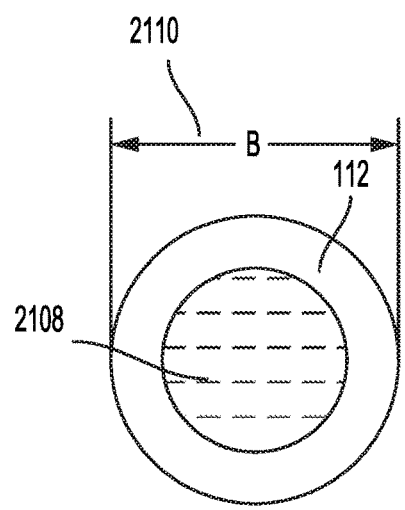
FIG. 16E depicts a front view the embodiment of the sensor of FIGS. 16D and 16C.

FIG. 16E shows a front view of the skin interface 2108 of the sensing electrode 112 of FIG. 16C. In implementations, the sensing electrode 112 has an diameter 2110 that is larger than the diameter 2112 of the button hole (e.g., button hole 2105 of FIG. 16F) so that the sensing electrode 112 resists flipping and remains in contact with a patient's skin.

Figure 16F:
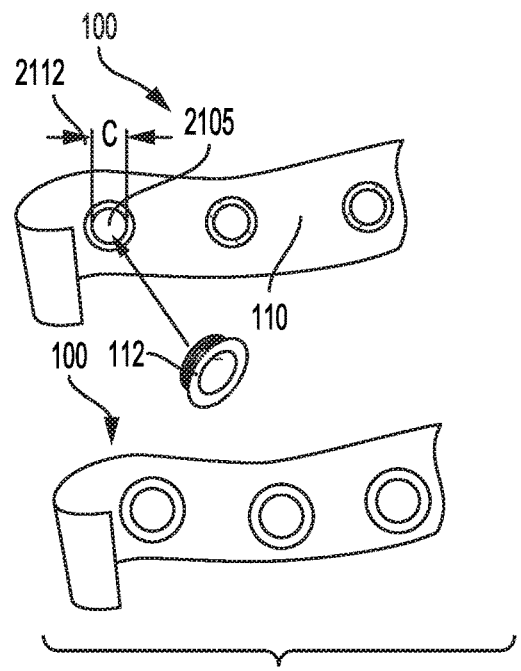
FIG. 16F depicts an exploded view of the assembled embodiment of the device of FIG. 16A.

FIG. 16F shows an exploded view and assembled view of the inside of the garment 110 with received electrodes 112 thereon. In some implementations, the sensing electrodes 112 and button holes 2105 are color coded for aiding assembly in a guided order.

Figure 16G:
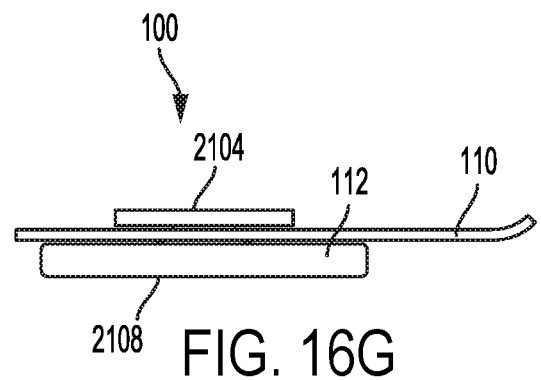
FIG. 16G depicts an embodiment of a side view of a portion of the embodiment of the device of FIG. 16A.
Figure 16H:
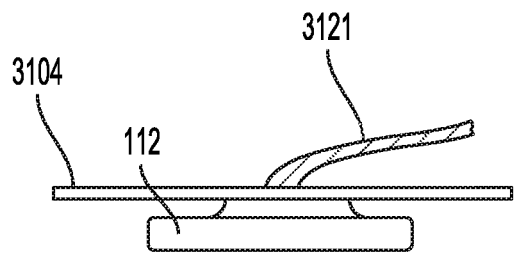
FIG. 16H depicts an embodiment of a portion of the device of FIG. 16A.

FIG. 16G shows a side view of the sensing electrode 112 of FIGS. 16C through 16E retained in button hole 2105 of the garment 110. One or more wires 3121 are connected to the plurality of sensing electrodes 112 along an outside surface of the garment 110. In the embodiment of FIG. 16H, the sensing electrode 112 has a wire 3121 permanently integrated with a wire interface 3104 (e.g., a non-patient contact surface). In some embodiments, the wire interface 3104 of the sensing electrode of FIG. 16H includes is a plastic ring integrated therewith and configured to rest against the outside of the garment 110 in an assembled configuration of the device 100. The diameter of the plastic ring wire interface 3104 is greater than the diameter of the button hole 2105 of the garment 110 so that the electrode 112 cannot be pulled through the button hole 2105 in the direction of insertion.

Figure 16I:
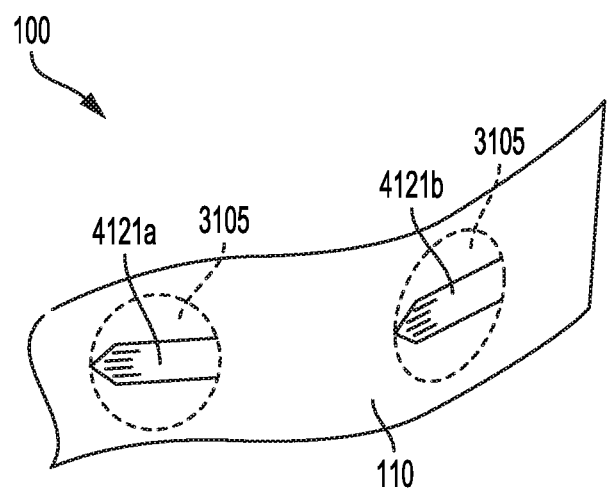
FIG. 16I depicts an embodiment of a front view of a portion of an embodiment of a patient-worn medical device.
Figure 16J:
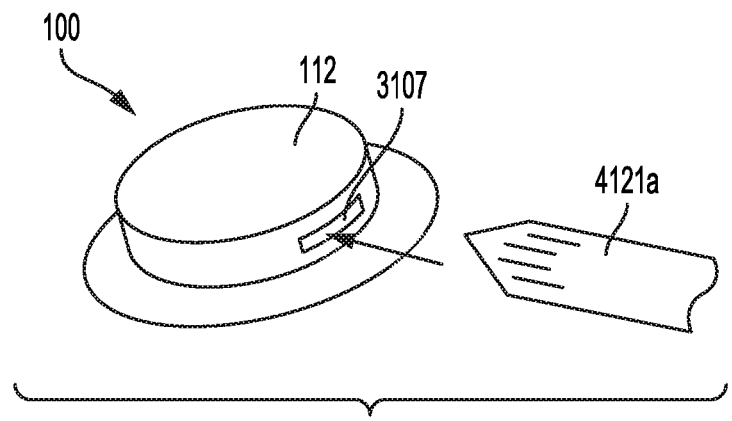
FIG. 16J depicts an exploded view of the embodiment of the device of FIG. 16I.
Figure 16K:
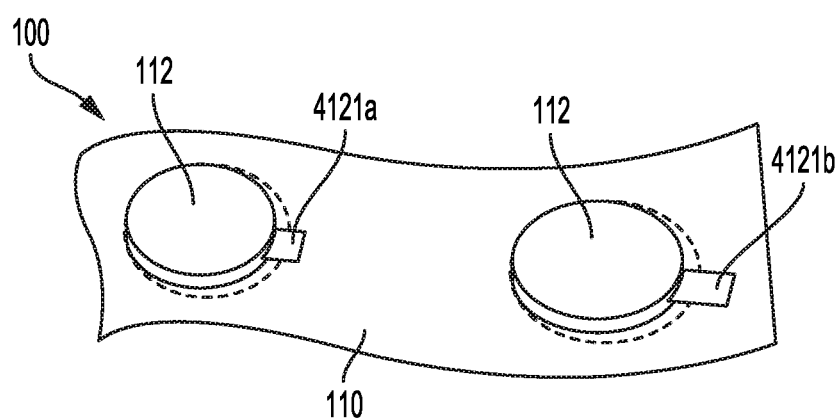
FIG. 16K depicts a perspective front view of the embodiment of the device of FIG. 16I.

In the embodiment of FIGS. 16I through 16K, the sensing electrode 112 includes a slot 3107 configured to receive a conductive fabric based tab connector 4121a, 4121b attached to or formed of the warp and weft of the garment 110. Assembly includes pushing a sensing electrode 112 through a button hole 3105 in the garment and inserting a tab connector 4121 into the slot 3107 to form an electrical connection. FIG. 16I shows the garment 110 without sensing electrodes 112 inserted therein. A plurality of button holes 3105 for receiving sensing electrodes 112 have extending thereinto tab connectors 4121a. 4121b for mating with sensing electrodes 112. FIG. 16J depicts the insertion of a tab connector 4121a into a receiving slot 3107 in the sensing electrode for forming an electrical connection. FIG. 16K shows sensing electrodes 112 securely mated to the garment 110 with tab connectors 4121a, 4121b securely mated to each of the sensing electrodes 112.

Figure 17A:
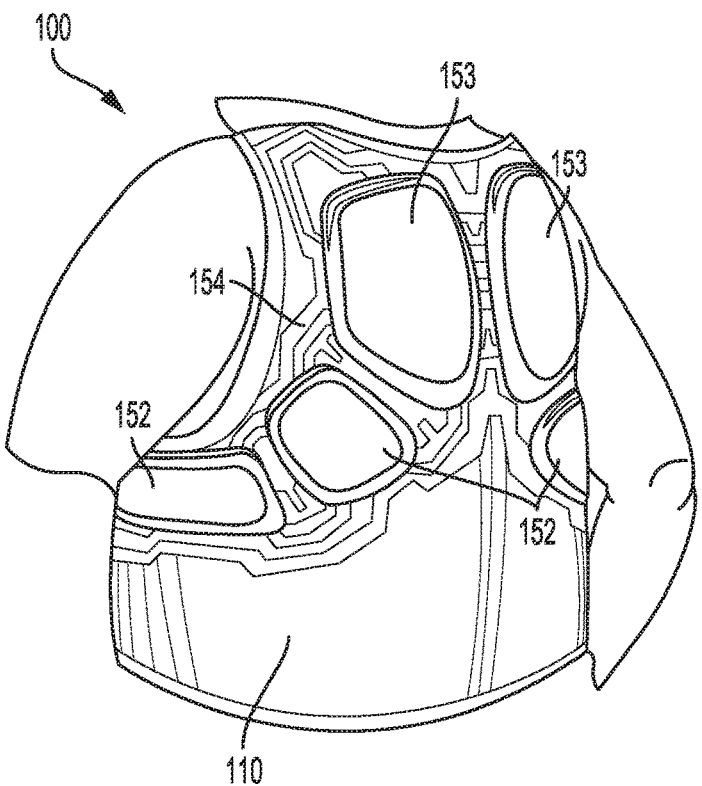
FIG. 17A depicts a rear perspective view of an embodiment of a patient-worn medical device.
Figure 17B:
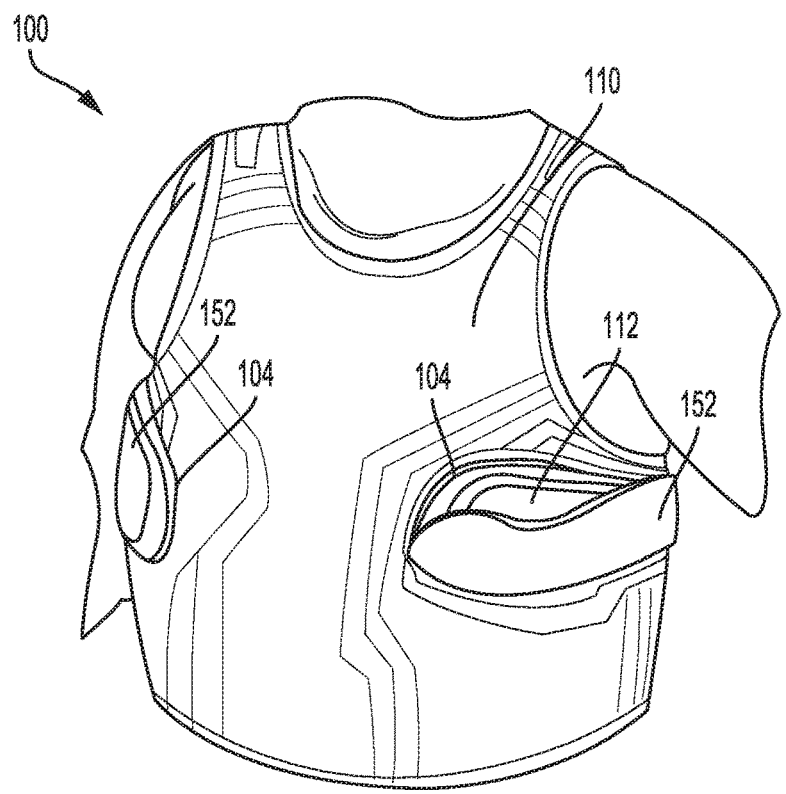
FIG. 17B depicts a front perspective view of the device of FIG. 17A.

In some embodiments of the device 100, such as that of FIGS. 17A-B, a garment 110 includes a conductive textile having compartments 152, 153 to receive one or more components, such as the sensing electrodes 112, the therapy electrodes 114, and one or more electronic components of the medical device 100, such as the capacitors, batteries, sensor interfaces, network interfaces, and the therapy delivery circuits. Some or all of the compartments 152, 153 include resealable closures 104, such as a zipper or water tight pressfit seal. The compartments 152, 153 include a connector (not shown) configured to mate with the inserted component (e.g., the sensing electrodes 112, the therapy electrodes 114, and one or more electronic components of the medical device 100, such as the capacitors 403, batteries 210, sensor interfaces 212, network interfaces 206, and the therapy delivery circuits 202), and the connector is electrically coupled to the conductive textile. Traces 154, printed on the garment 110 or woven as conductive fibers into the warp and weft of the garment 110, connect the compartments 152, 153 and the components received therein.

Figure 18A:
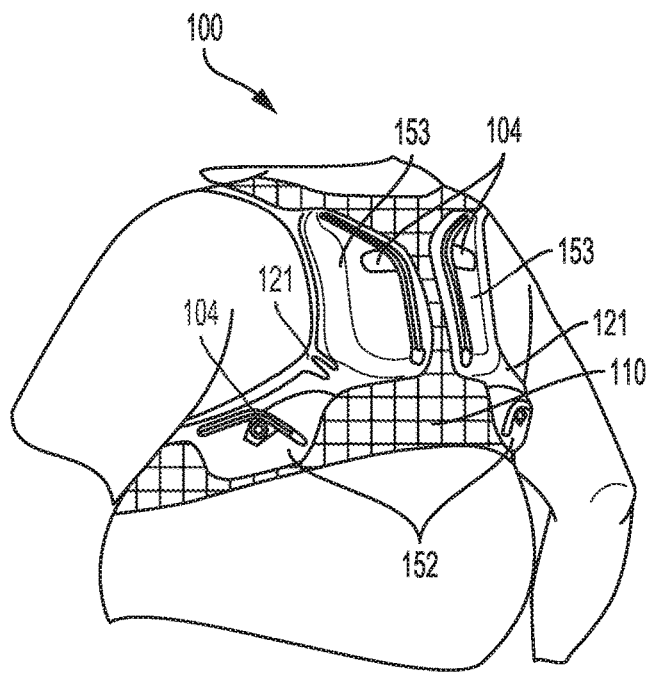
FIG. 18A depicts a rear perspective view of an embodiment of a patient-worn medical device.
Figure 18B:
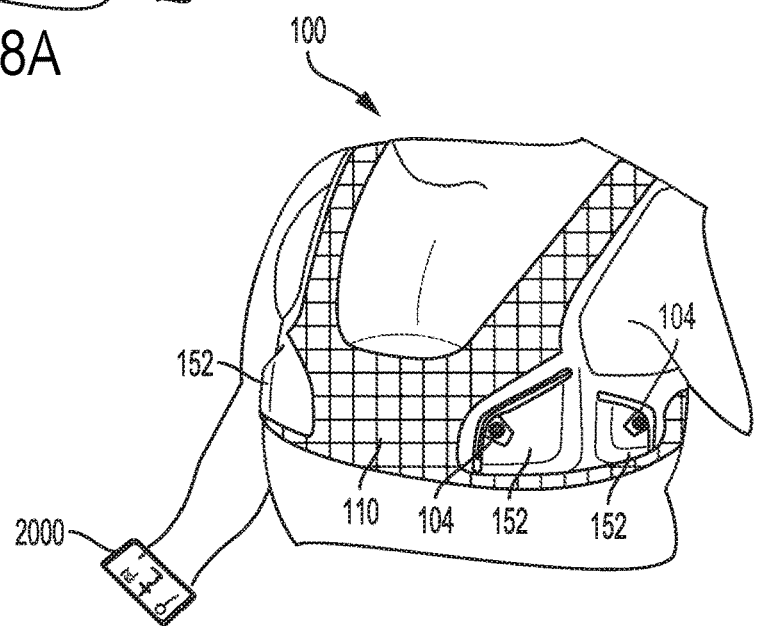
FIG. 18B depicts a front perspective view of the device of FIG. 18A.
Figure 18C:
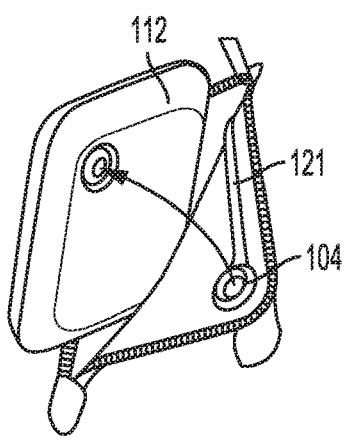
FIG. 18C depicts a magnified exploded view of a portion of the device of FIGS. 18A and 18B.

In some embodiments, such as that of FIG. 18, the device 100 includes a garment 110 comprised of or including compartments 152, 153 configured to receive one or more components, such as the sensing electrodes 112, the therapy electrodes 114, and one or more electronic components of the medical device 100, such as such as the capacitors 403, batteries 210, sensor interfaces 212, network interfaces 206, and the therapy delivery circuits 202. Some or all of the compartments 152, 153 include one or more conductive resealable closures 104, such as a snap. The one or more resealable closures 104 mate with the component, such as the sensing electrode 112 of FIG. 18C, received in the compartment 152, 153. The one or more resealable closures 104 simultaneously fasten the sensing electrode 112 to the garment 110 and completes an electrical circuit. The electrical circuit includes a wire 121 integrated into the garment 110 and electrically coupled with the one or more resealable closures 104 and with one or more electronic components of the medical device 100, such as the capacitors, batteries, sensor interfaces, network interfaces, and the therapy delivery circuits. In implementations, the device 100 communicates wirelessly with an external device, such as an app-enabled smartphone 2000.

Figure 19A:
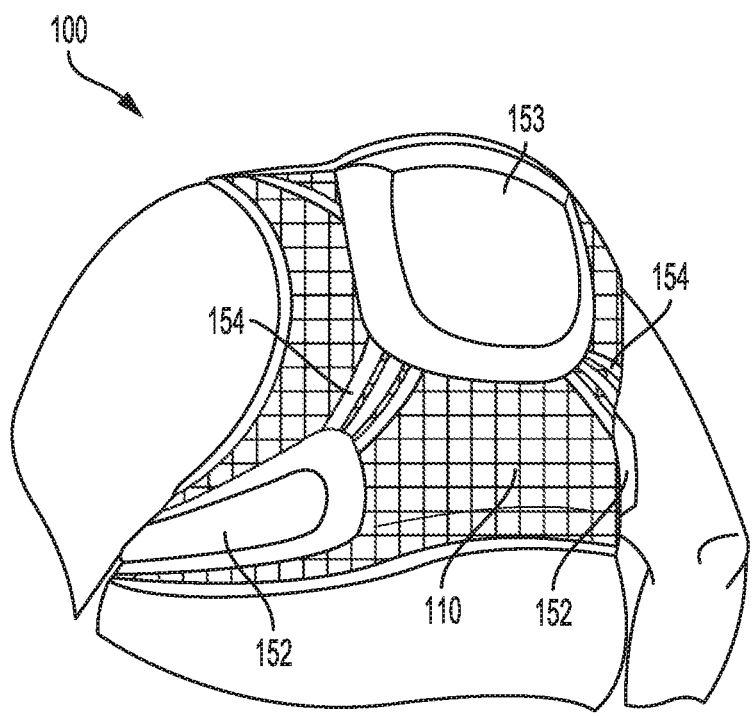
FIG. 19A depicts a rear perspective view of an embodiment of a patient-worn medical device.
Figure 19B:
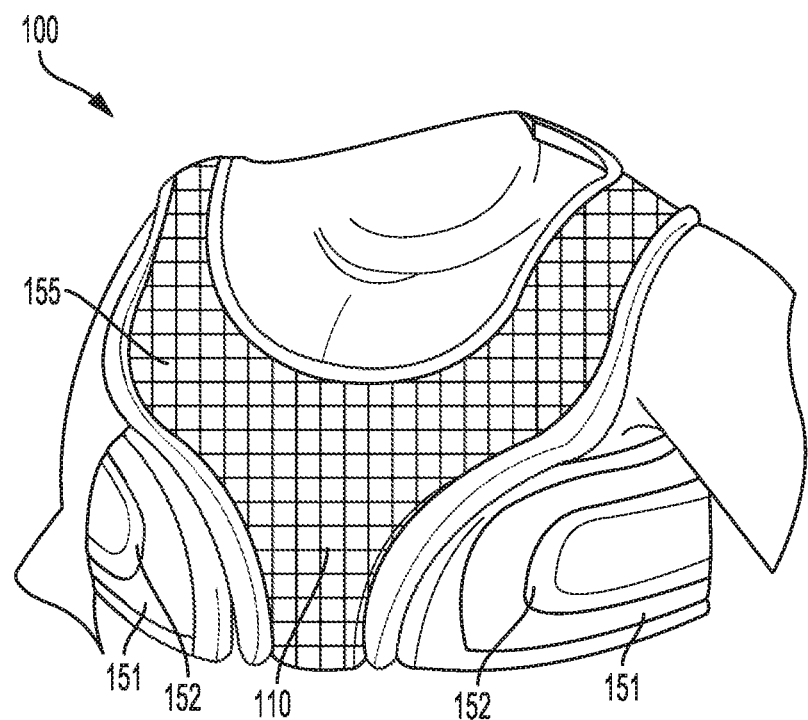
FIG. 19B depicts a front perspective view of the device of FIG. 19A.

In another embodiment of the device 100 shown in FIGS. 19A and 19B, one or more of a plurality of compartments 152, 153 are molded and mounted to the garment. The garment 110 includes a conductive textile with electrically connected compartments 152, 153 for receiving and electrically connecting components such as the plurality of sensing electrodes, the plurality of therapy electrodes and one or more electronic components of the medical device 100, such as the capacitors, batteries, sensor interfaces, network interfaces, and the therapy delivery circuits (for example, electronics components described with regard to the schematic of FIG. 2). In the embodiment of FIGS. 19A and 19B, the plurality of compartments 152, 153 are sealed in a watertight configuration and the patient may bathe or shower while wearing the device 100. The device 100 includes additional comfort features for improving the patient's comfort during the prescribed duration of wear. The device 100 includes two soft-molded sided straps 151 attached to a central chest flap 155 for off-center fastening. Because the side straps 151 are off to the sides of the garment 110, they are easily reached by the patient's hands and adjusted during periods of wear in accordance with the patient's comfort preferences. The side straps 151 may be secured, for example, by a fastener adjustable to any girth setting that is comfortable to the patient, such as strips of opposed hook and loop fastener or magnetic strips.

In each of the embodiments of 17A through 19B, the compartments for receiving the electronic components may be sized and shaped complimentary to the size and shape of each inserted component, as described above with regard to FIGS. 5A, 41A and 41B. In some examples, the garment 110 further includes at least one thermoform shell integrated into at least one of the plurality of compartments for receiving at least one of the plurality of therapy electrodes 114 and/or sensing electrodes 112.

Other types of fasteners 270 are contemplated by the present disclosure. In implementations of the device 100 includes one or more fasteners 270 that facilitate securing and removing the device 100, particularly when dexterity and range of motion are limited. As described above with regard to FIGS. 5A and 5B, embodiments also include additional features, such as a disengagement sensor 260 that indicates disengagement of the one or more fasteners 270 prior to the expiration of a prescribed duration of wear. In implementations, the disengagement sensor 260 is electrically coupled to the controller 120 and is configured to provide the indication of disengagement by generating an electrical signal in response to mechanical disengagement of the one or more fastener 270. Alternatively or additionally, the disengagement sensor can include a physical structure that provides physical evidence of disengagement. For example, such a structure can include a breakaway element that is permanently unsealed, broken, separated, ruptured, or otherwise compromised upon disengagement. The breakaway element can include, for example, a frangible wrapper that permanently separates into two or more portions. In some implementations, the breakaway element can include a color changing element that permanently changes color in response to being stretched beyond a predetermined limit. In implementations, the disengagement sensor is a security ring, a tamper evident band, a breakaway band, a perforated thermoplastic shrink seal, or a security band. In implementations, the disengagement sensor is a security tape including one or more of intentionally weak or frangible tear lines or layers that delaminate and leave behind printed indicia indicating opening. In implementations including a physical structure providing physical evidence of disengagement, the structure may be removed or broken with a tear force or separation force accommodating patients with limited dexterity or strength. For example, the physical structure may be a frangible seal or security ring requiring a breakaway force in the range of about 0.1 lbf to 10 lbf (e.g., 0.1 lbf-0.3 lbf, 0.25 lbf-1.0 lbf, 0.5 lbf-2 lbf, 0.1 lbf-5.0 lbf, 5.0 lbf-10.0 lbf, 9.0 lbf-10 lbf, 1.0 lb-8.0 lbf, 0.1 lbf-10 lbf).

Figure 38A:
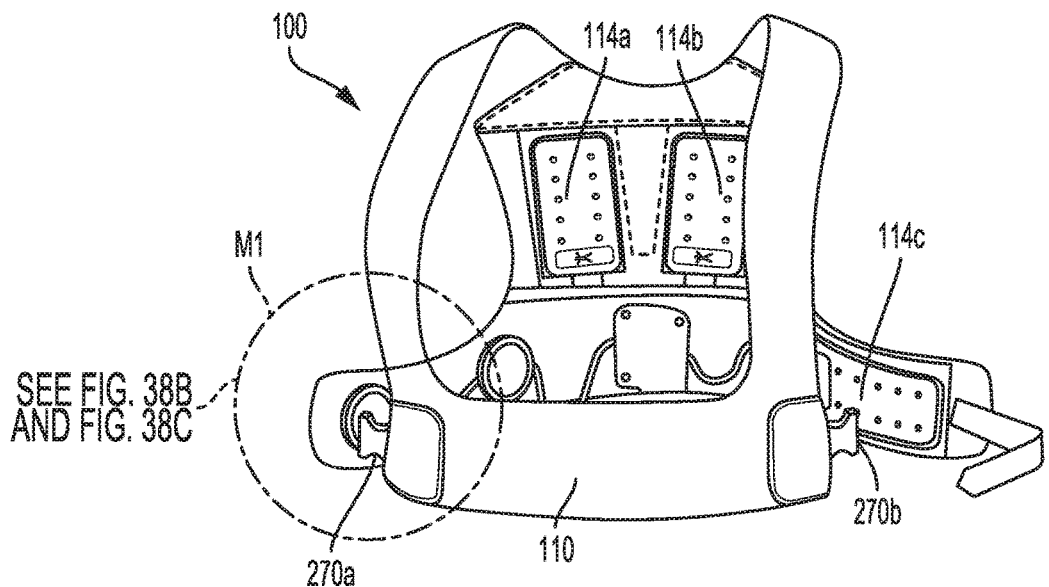
FIG. 38A depicts a front view of an embodiment of a patient-worn medical device.
Figure 38B:
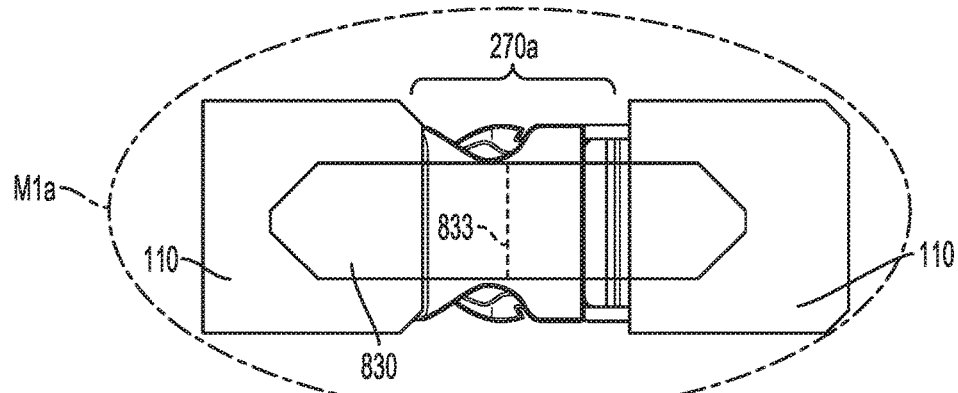
FIG. 38B depicts a magnified portion of a fastener of a patient-worn medical device in an fastened state.
Figure 38C:
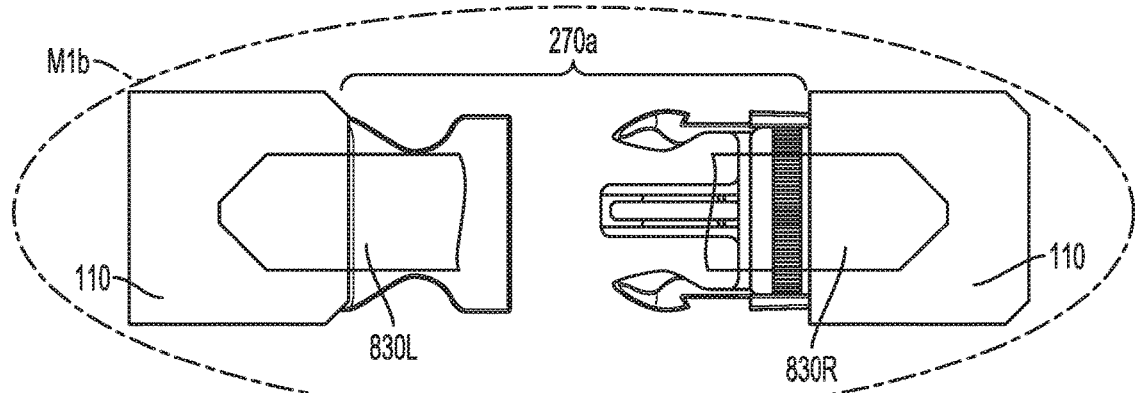
FIG. 38C depicts a magnified portion of an embodiment of a fastener of a patient-worn medical device in an unfastened state.

FIGS. 38A through 38C depict an example of one or more fasteners 270a, 270b that are side release buckles for use with medical device 100. Circled portion M1 is magnified in the section views of FIGS. 38B and 38C. FIG. 38B depicts a magnified view M1a of a side release buckle fastener 270a in a fastened state. A strip of security tape 830 is applied across the buckled fastener 270a and includes a frangible break away perforation 833 that separates when the side release buckle fastener 270a is unfastened. The force of the buckle fastener 270a pulling apart tears the security tape 830 along the frangible break away perforation 833. FIG. 38C depicts a magnified view M1b the side release buckle fastener 270a in an unfastened state such that the security tape 830 is broken into separate left and right pieces 830L, 830R attached to either half of the unfastened buckle fastener 270a. When the buckle fastener 270a is rejoined, the security tape 830 remains broken and the separate pieces 830L, 830R cannot be rejoined. The device 100 therefore provides a physical indication that the side release buckle fastener 270 has been unfastened.

Figure 39A:
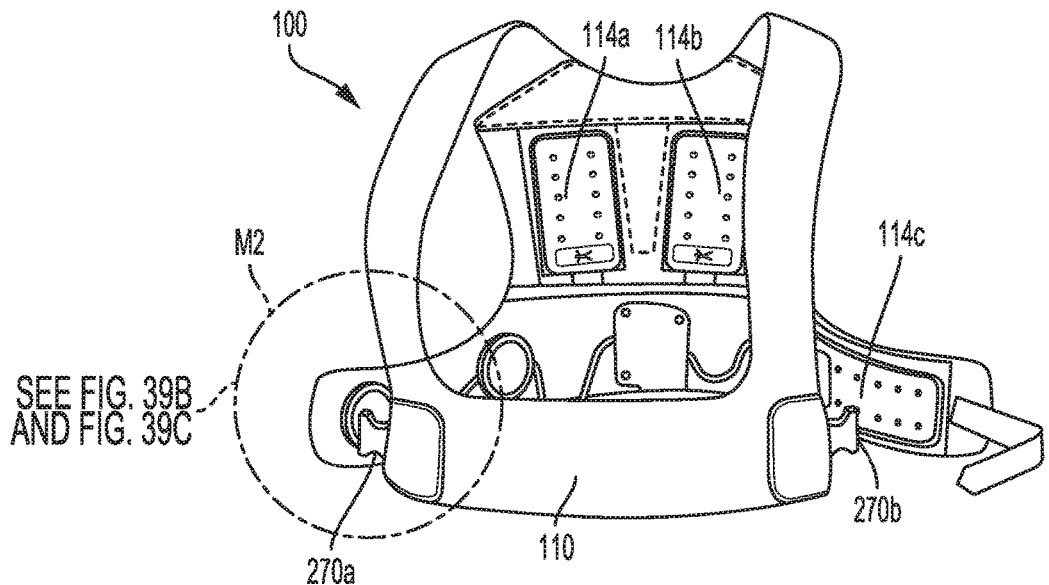
FIG. 39A depicts a front view of an embodiment of a patient-worn medical device.
Figure 39B:
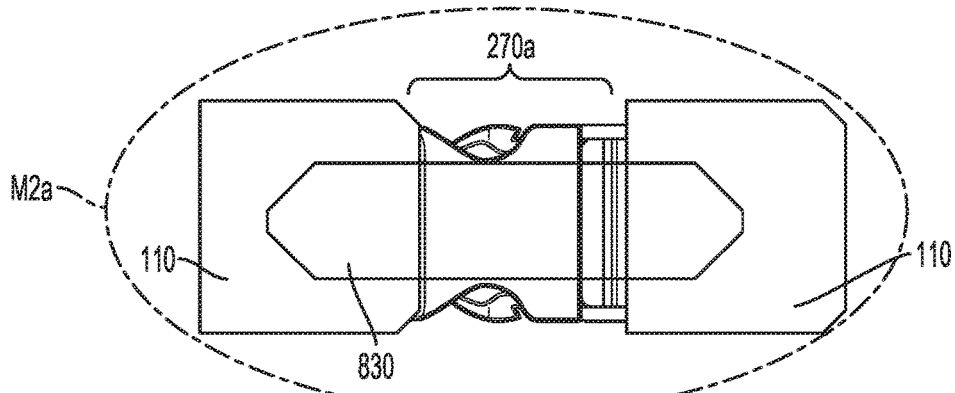
FIG. 39B depicts a magnified portion of an embodiment of a fastener of a patient-worn medical device in an fastened state.
Figure 39C:
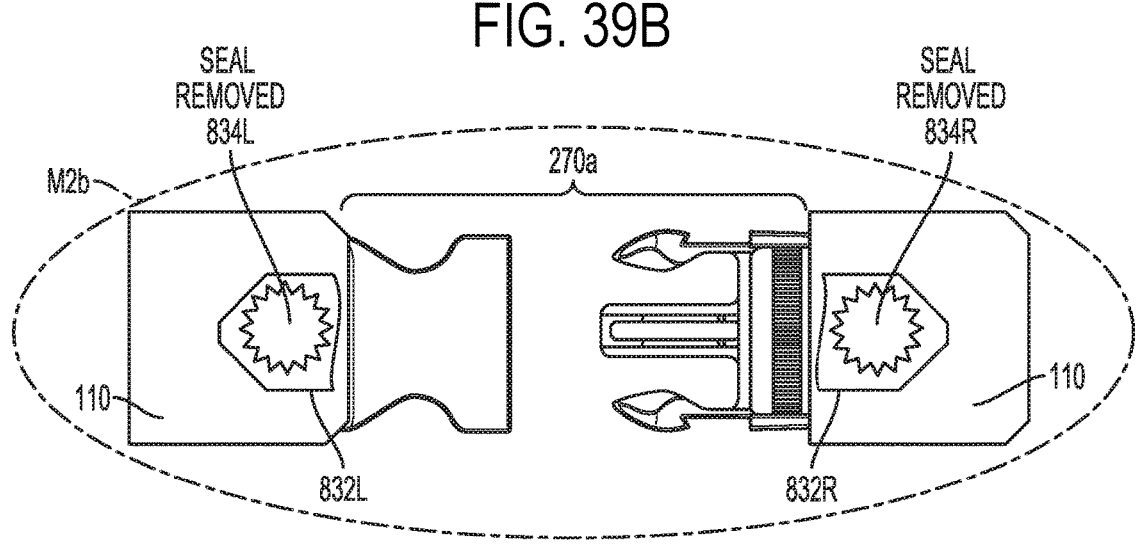
FIG. 39C depicts a magnified portion of an embodiment of a fastener of a patient-worn medical device in an unfastened state.

Similarly, FIGS. 39A through 39C depict an embodiment of the device 100 having a pair of fasteners 270a, 270b that are side release buckles. Circled portion M2 is magnified in the section views of FIGS. 39B and 39C. FIG. 39B depicts a magnified view M2a of a side release buckle fastener 270a in a fastened state. A strip of security tape 830 is applied across the buckle fastener 270a, and the security tape delaminates and leaves behind written indicia 834L, 834R of removal when the side release buckle fastener 270a is unfastened. The force of the buckle fastener 270a pulling apart dislodges an outer layer of the security tape 830. FIG. 38C depicts a magnified view M2b of the side release buckle fastener 270a in an unfastened state such that the security tape 830 is delaminated, leaving behind separate pieces 832L, 832R attached to the garment 110. The device 100 therefore provides a physical indication that the side release buckle fastener 270a has been unfastened.

Figure 40A:
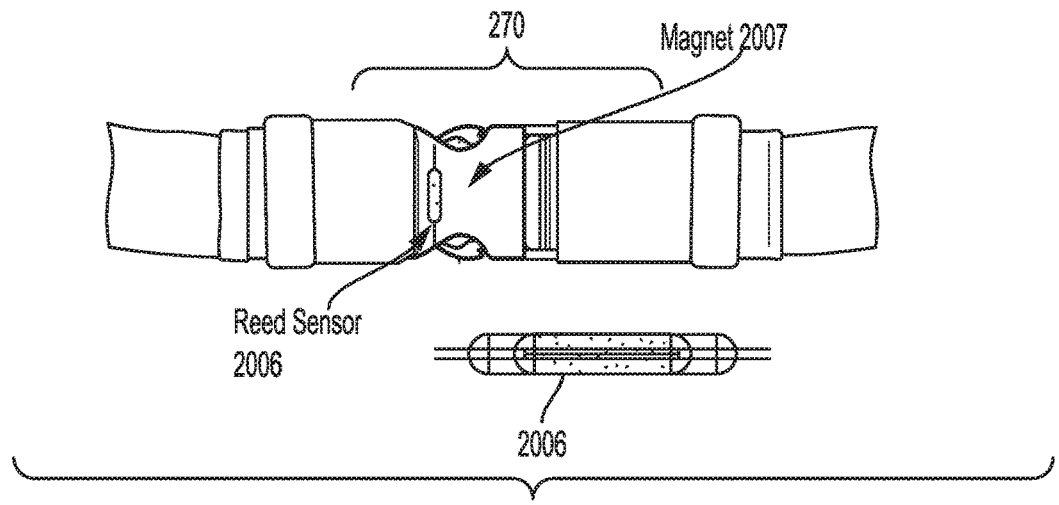
FIG. 40A depicts an embodiment of a fastener of a patient-worn medical device in an fastened state.
Figure 40B:
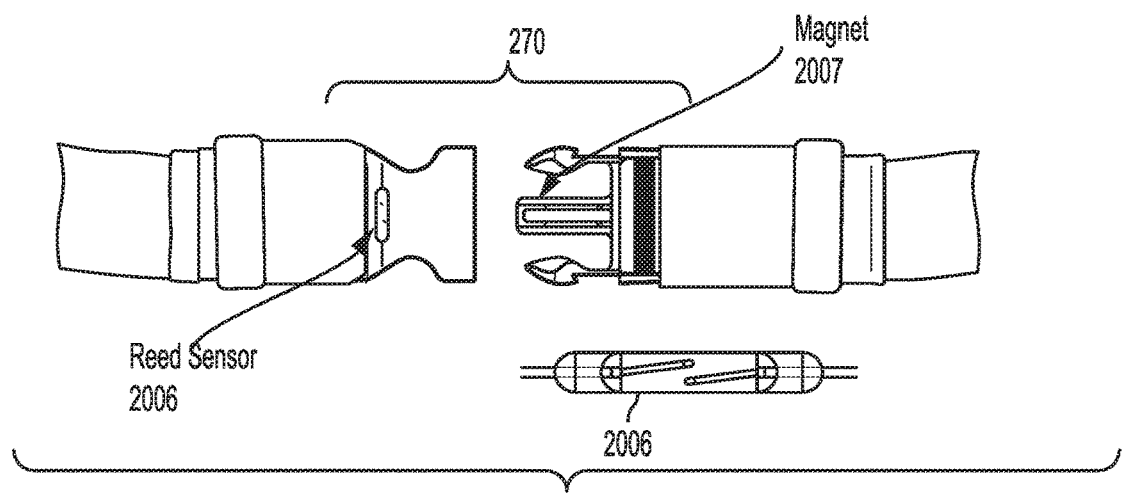
FIG. 40B depicts an embodiment of a fastener of a patient-worn medical device in an unfastened state.
Figure 40C:
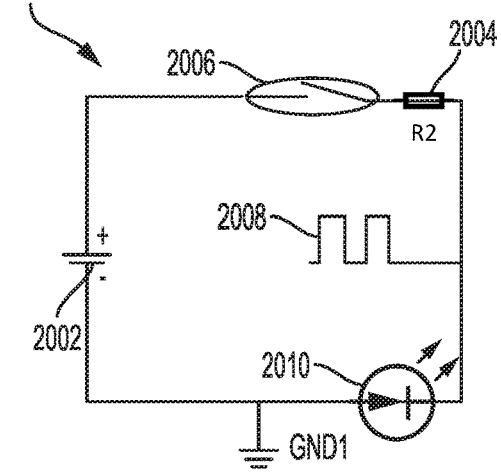
FIG. 40C depicts an example schematic for a disengagement sensor of a patient-worn medical device.

In configurations, the controller 120 is configured to receive an electrical signal generated in response to mechanical disengagement of the one or more fasteners 270 and provide an alert. In implementations, such as that shown in FIGS. 40A through 40C, the fastener 270 includes a magnet 2007 and a switch 2006 activated by the magnet 2007. For example, as shown in FIG. 40C, the fastener includes a resistor 2004 in series with a magnet activated switch 2006, such as a reed switch or a hall sensor, that completes a circuit when the magnet 2007 is in proximity (e.g., the fastener 270 is engaged), thereby signaling to a controller 2008, such as processor 218 of FIG. 2, that the one or more fasteners 270 are engaged or disengaged.

In embodiments, the electrical signal is an alert such as a flag stored in memory for later retrieval. In embodiments, the alert is a notification sent to a remote server. For example, the remote server can be configured to further notify one or more designated persons (e.g., the patient, caregivers, technicians, and/or other designated individuals) that the garment 110 of the patient has been disengaged. For instance, one or more of the designated persons may receive the notifications via a text alert, an e-mail communication, or other mode of communication on a hand-held device or other electronic device. In other embodiments, the alert is a notification displayed or transmitted at a user interface of the medical device, such an LED 2010 display. In some implementations, the alert may be one or more of an audible signal, a visual signal, or a change in physical structure providing physical evidence of disengagement, such as a breakaway element that is rejoined or an element that changes color permanently upon separation.

In some examples, the device 100 includes elements that enable adjusting the locations of one or more of the sensing electrodes 112, therapy electrodes 114, and heavy controller components, such as the capacitors 403 and battery 210. Embodiments also include features, such as one or more disengagement sensors 260, that indicate disengagement of a one or more of the sensing electrodes 112, therapy electrodes 114, and controller components (e.g. the one or more capacitors 403, the therapy delivery circuit 202, the processor 218, and the network interface 206) prior to the expiration of a prescribed duration of wear. The disengagement sensors 260 are coupled to the controller 120, and the controller 120 is configured to provide an alert during the period of disengagement of one or more of the sensing electrodes, therapy electrodes, and controller components so that the patient is reminded to reattach the disengaged configurable components.

As described previously, examples of the garment 110 vary from wrap-around belts, to over the head pull-on shirt-style garments, to side-fastening vest-style garments. The following examples of fasteners, physical and/or electrical disengagement sensors, and/or tensioners are contemplated for alternative or additional implementation with any of the disclosed styles of garment 110 of the device 100.

Additionally or alternatively, the controller 120 can be configured to detect removal (e.g., disrobing) of the device 100 from the body 102 of the patient prior to the expiration of a prescribed duration of wear based on a failure to detect a physiological signal (e.g., an ECG signal, bioimpedance, plethysmographic, or a cardiac vibrational signal) of the patient. Such a failure to detect the physiological signal of the patient indicates that one or more sensing electrodes 112 may be no longer in contact with the body 102 of the patient. In this regard, the controller 120 is configured to detect when one or more sensors fail to detect a physiological signal from the patient for a threshold period of time. For example, the controller 120 may monitor a predetermined number of sensors for the failure to detect the physiological signal. For example, the controller 120 is configured to indicate removal of the device 100 when at least two sensors fail to detect the physiological signal. A lack of detection of a physiological signal indicating removal of the device 100 may be preceded by continuous monitoring of the physiological signal without detection of a change in health condition (e.g., a sudden cardiac event). For example, if the controller 120 detects that two or more sensing electrodes 112 fail to detect an otherwise continuously monitored cardiac signal for a duration lasting between about 1 to 5 minutes, the controller 120 is configured to provide at least one of an audible, visible, and haptic alert to at least one of the patient and a remote caregiver. The alert provides a notification of removal of the device 100 prior to the expiration of the prescribed duration of wear. In other examples, the controller 120 can be configured to provide an alert immediately upon detecting that two or more sensing electrodes 112 failed to detect an otherwise continuously monitored physiological signal from the patient. In some examples, the patient could control the duration under the direction of a physician or caregiver and configure the threshold period of time to a duration lasting minutes, hours, and/or days. In examples, the threshold period of time could be 1-5 minutes, 1-10 minutes, 1-30 minutes, 1 hour, 2 hours, 5 hours, 1 day, or 2 days. In examples, the threshold period of time includes a duration ranging from 1-30 seconds, such that the controller is configured to immediately provide the notification upon detecting the loss of signal. In examples, the notification includes at least one of an audible, visible, and haptic alert provided to at least one of the patient and a remote caregiver.

Although sensing electrodes 112 are used by way of example, other sensors configured to continuously monitor a patient parameter can provide an indication of removal of the device. For example, the controller can monitor continuous receipt of one or more signals from one or more sensors for detecting physiological information other than an ECG signal. For example, such as sensors include those for measuring blood oxygen, the patient's temperature, galvanic skin response (GSR), bioimpedance, pethysmographic, near infrared spectroscopy (NIRS), glucose levels, tissue fluid levels, pulmonary vibrations, and/or movement (e.g., an accelerometer). If two or more of these sensors or a combination of one of these sensors and a sensing electrode 112 fail to communicate a detected signal to the controller 120 for a threshold duration of time, e.g., 1 minute to 5 minutes, the controller 120 can provide an alert that the continuously monitored signals are no longer detected. In other examples, the controller 120 can provide an alert immediately upon detecting a failure to communicate a detected signal by two or more of the sensors for detecting physiological information other than an ECG signal, or a combination of one of these sensors and at least one sensing electrode 112.

Turning now to FIGS. 20A through 20D, embodiments of the device 100 include fasteners 270 and closure assistance features for enabling patients with limited dexterity to engage with a closure mechanism and secure the device 100 about their torso. A closure mechanism 700 is an integral or adjoined portion of the garment 110 that includes thereon one or more fasteners 270. For example, as in FIGS. 20A through 22B, a closure mechanism 700 includes two ends of a belt or strap, and the fastener 270 includes mating elements apportioned on either end of the belt or strap. In other embodiments, the closure mechanism is a layered flap (e.g., the side flap fastener 270 of FIGS. 33A and 33B) for securing to another portion of the garment 110 or two panels of a garment joined by a fastener (e.g., the full length fastener 270 of FIGS. 35A and 25B).

Figure 20A:
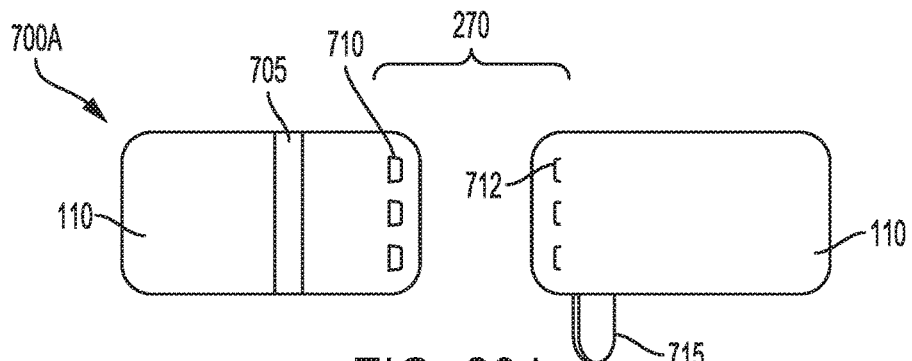
FIG. 20A depicts a front view of an embodiment of a closure assembly for an embodiment of a patient worn medical device.

As the example of FIG. 20A shows, on one side of the closure mechanism 700A, a thumb loop 715 is configured to receive a patient's thumb of a first hand. The opposing side of the closure mechanism 700A a large loop 705 for receiving the second hand of the patient. In embodiments, the large loop 705 is elastic and stretches to accommodate the patient's hand size. With a thumb inserted in the thumb loop 715 and an opposing hand inserted under the large loop 705, a patient need only push hands together to engage two sides of a mating fastener 270, such as hooks 710 and eyelets 712.

Figure 20B:
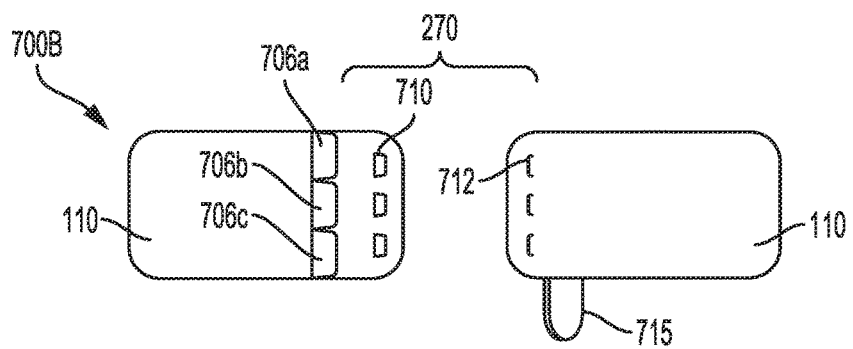
FIG. 20B depicts a front view of an embodiment of a closure assembly for an embodiment of a patient worn medical device.

As the example of FIG. 20B shows, on one side of the closure mechanism 700B, a thumb loop 715 is configured to receive a patient's thumb of a first hand. The opposing side of the closure mechanism 700B includes a plurality of finger pockets 706a, 706b, 706c, for receiving a plurality of fingers of the second hand of the patient. With a thumb inserted in the thumb loop and fingers of an opposing hand inserted into a plurality of finger pockets 706a-c, a patient need only push hands together to engage two sides of a fastener 270, such as hooks 710 and eyelets 712.

Figure 20C:
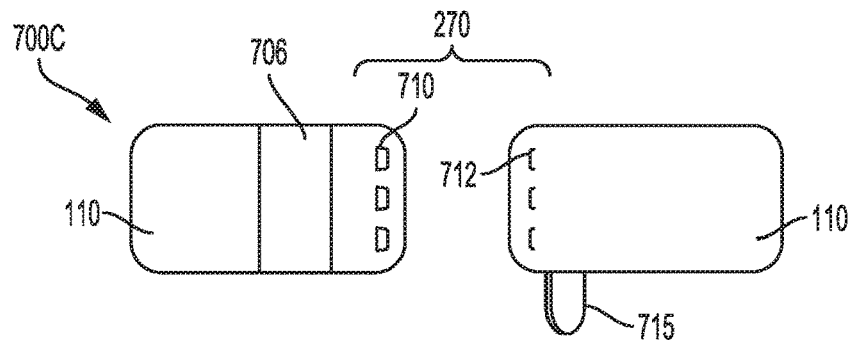
FIG. 20C depicts a front view of an embodiment of a closure assembly for an embodiment of a patient worn medical device.

As the example of FIG. 20C shows, on one side of the closure mechanism 700C, a thumb loop 715 is configured to receive a patient's thumb of a first hand. The opposing side of the closure mechanism 700C includes a pockets 706, for receiving a second hand of the patient. With a thumb inserted in the thumb loop 715 and the opposing hand inserted into the pockets 706, a patient need only push hands together to engage two sides of a fastener 270, such as hooks 710 and eyelets 712.

Figure 20D:
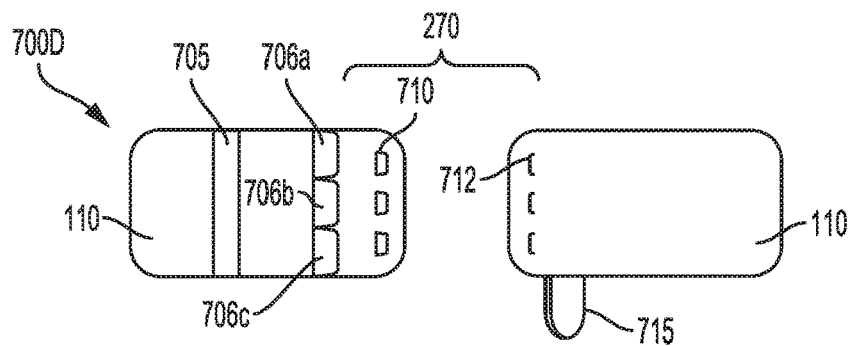
FIG. 20D depicts a front view of an embodiment of a closure assembly for an embodiment of a patient worn medical device.

As the example of FIG. 20D shows, on one side of the closure mechanism 700D, a thumb loop 715 is configured to receive a patient's thumb of a first hand. The opposing side of the closure mechanism 700D includes a large loop 705 for receiving the second hand of the patient and a plurality of finger pockets 706a, 706b, 706c, for receiving a plurality of fingers of the second hand of the patient. In embodiments, the large loop 705 is elastic and stretches to accommodate the patient's hand size. With a thumb inserted in the thumb loop and an opposing hand inserted under the large loop 705 and fingers inserted into the plurality of finger pockets 706a-c, a patient need only push hands together to engage two sides of a fastener 270, such as hooks 710 and eyelets 712.

In each of these embodiments of FIGS. 20A through 20D, a patient avoids having to pinch the garment 110 with their fingers and pull the opposing sides of the closure mechanism 700 together to dexterously connect each side of a fastener 270. The embodiments require only gross motions and avoid requiring any fine motor skills, such as pinching or threading.

Figure 21A:
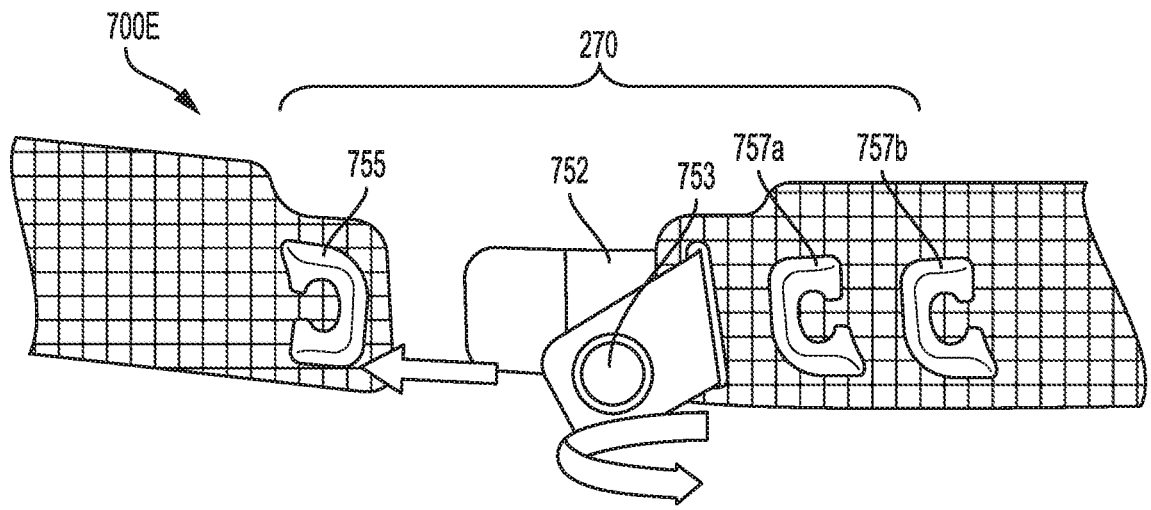
FIG. 21A depicts an embodiment of an adjustable fastener of a patient-worn medical device.
Figure 21B:
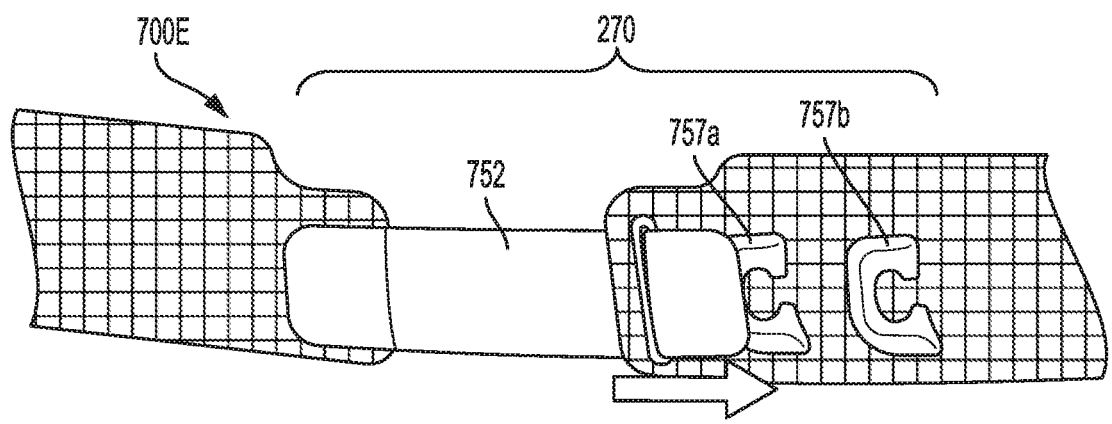
FIG. 21B depicts an embodiment of the adjustable fastener of FIG. 21A.
Figure 21C:
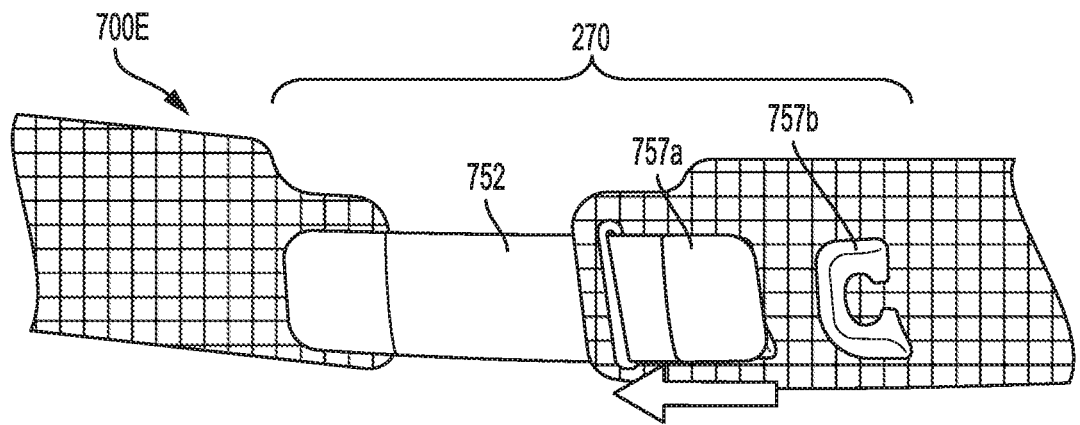
FIG. 21C depicts an embodiment of the adjustable fastener of FIGS. 21A and 21B.

In some embodiments, the fastener 270 can include an integrated tensioning mechanism or tensioner as described in further detail below. For example, in some implementations, such as those of FIGS. 21A through 21C, the closure mechanism 700E is configured to be secured, and subsequently adjusted for further tightening as necessary (e.g., in accordance with the patient's comfort preferences and/or to facilitate arrhythmia detection and delivery of therapy) while the patient is wearing the garment 110. For example, over a prescribed duration of wear, a user may tighten the garment 110 as the device 100 stretches so that the sensing electrodes 112 and therapy electrodes 114 remain compressed against the torso for effective treatment and arrhythmia detection. Additionally or alternatively, tightening the garment 110 maintains the sensing electrodes 112 and therapy electrode 114 positioned in optimal locations on the torso of the patient to provide effective ECG detection leads and therapeutic pulse vectors. In the example of FIGS. 21A through 21C, the closure mechanism 700E includes a fastener 270 having non-stretch strap 752 with a retention element 753, such as a snap, a protrusion, or a button, integrated on each end. One side of the closure mechanism 700E includes a receiving element 755 of the fastener 270 for securely holding a retention element 753 of one end of the strap 752. The other side of the closure mechanism 700E includes a plurality of receiving elements 757a, 757b for receiving a retention element 753 of the other end of the strap 752. In this manner, the fastener 270 secures free ends of the closure mechanism 700E and also functions as a tensioner for the garment 110. For instance, if the device 100 loosens during the duration of wear, the patient may disengage the retention element 753 from the closest one of the plurality of receiving elements 757a, pull the strap 752 to tighten the closure mechanism 700E, and reinsert the retention element 753 into a more distant receiving element 757b. This tightens the garment 110 around the torso of the patient. In embodiments, the retention elements 753 and receiving elements 755, 757a, 757b are configured to be electrically coupled. Inserting the retention elements 753 of the strap 752 into the receiving elements 755, 757a, 757b completes an electrical circuit and establishes an electrical communication with a disengagement sensor 260, as depicted in FIGS. 5A and 5B.

Figure 22A:
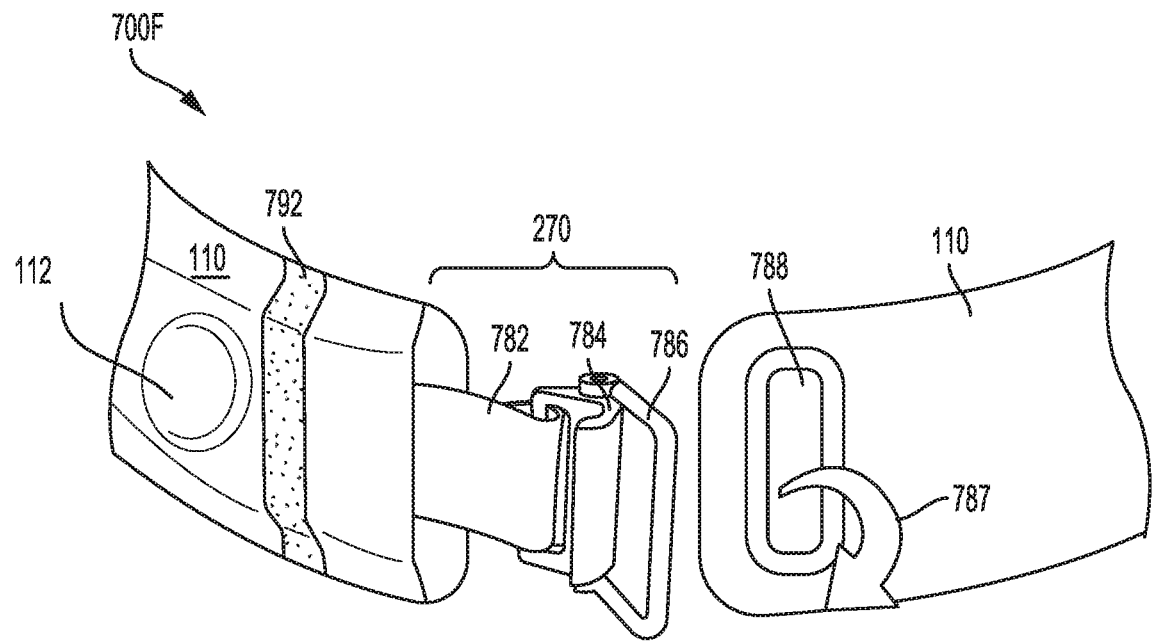
FIG. 22A depicts an embodiment of a fastener of a patient-worn medical device.
Figure 22B:
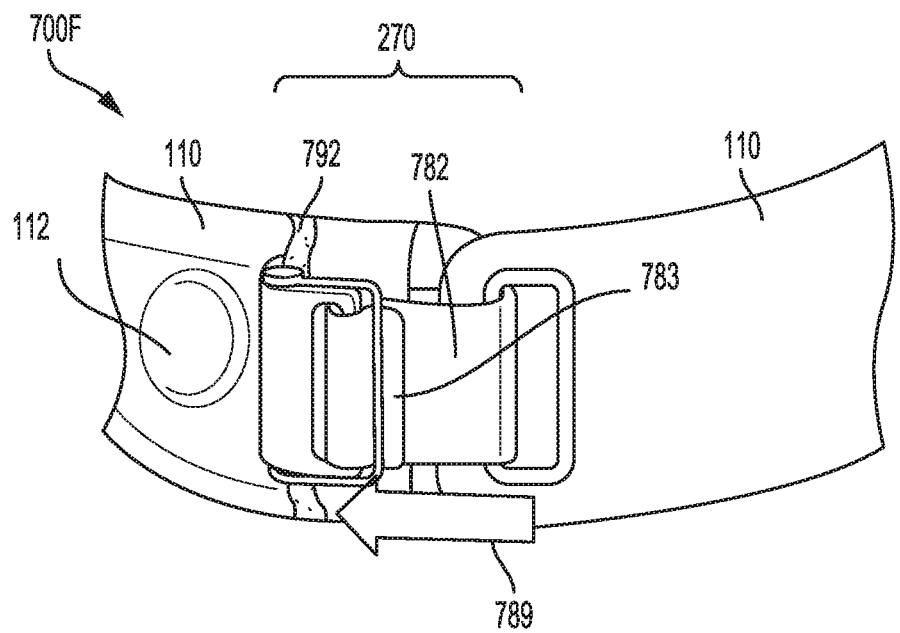
FIG. 22B depicts an embodiment of the fastener of FIG. 22A.

FIGS. 22A and 22B show another example of an adjustable fastener 270 with tensioner for securing the device 100 about the torso of the patient, and optionally subsequently tightening the garment 110 during the prescribed duration of wear. The adjustable fastener 270 includes a cinch strap 782 extending from one side of a closure mechanism 700F of the garment 110. An affixed hook closure 784 and optional grab loop 786 facilitate manipulation. A patient threads the grab loop 786 through a receiving slot 788 in the opposing side of the closure mechanism 700F in the direction of the curved arrow 787. The patient pulls the cinch strap 782 back toward the side of the closure mechanism 780 from which it extends, as indicated by the straight arrow 789 in FIG. 22B. The hook closure 784 latches onto a retaining clip 792 affixed to the closure mechanism 780 to secure the garment 110 in place about a torso of a patient. In embodiments where the cinch strap 782 functions as a tensioner, the cinch strap 782 is adjustable to accommodate multiple tightening settings without having to disengage the fastener 270. For example, a free end 783 of the cinch strap 782 can be pulled by the patient to tighten the fastener 270 thereby further tensioning the garment 110 about the patient's torso. In this manner, the cinch strap 782 can be used to cause the garment 110 to secure the plurality of ECG sensing electrodes 112 on the torso of the patient to facilitate detection of the arrhythmia condition. In implementations, connecting the hook closure 784 to the retaining clip 792 completes an electrical circuit and establishes an electrical communication with a disengagement sensor 260, as depicted in FIGS. 5A and 5B. In some examples, the fastener 270 includes a physical indication of separation. For example, as discussed with regard to FIGS. 38A-39C, the fastener 270 includes a security tape adhered thereacross with a frangible break away line or delaminating layers that leave an irreversible indication of disengagement of the fastener 270.

Some embodiments of the device 100, include an adjustable tensioner 790 separate from the fastener 270 such that the tensioner 790 enables a patient to selectively tension the device 100 without having to disengage a fastener 270 and loosen or remove the garment 110. The tensioner 790 for tightening the garment 110 about the torso of the patient while the garment 110 is being worn causes the garment 110 to secure the plurality of ECG sensing electrodes 112 and the plurality of therapy electrodes 114 on the torso of the patient to facilitate the detection of the arrhythmia condition of the patient and facilitate delivery of the one or more therapeutic pulses to the patient. If, for example, an ECG sensing electrode 112 is held loosely against the skin of the patient's torso, the signal quality might be poor because of noise artifacts in the signal. Not holding a sensing electrode 112 securely against the torso of the patient might not be optimal for detecting an arrhythmia condition. Tensioning the garment to hold the plurality of sensing electrodes 112 securely against the torso of the patient enables detection of a reliable signal for detecting an arrhythmia. Similarly, if the plurality of therapy electrodes 114 separate from the torso of the patient, energy being delivered during a therapeutic treatment pulse might dissipate because of increased impedance at the skin interface, which may include a disadvantageous air gap. By enabling tensioning of the garment 110 about the torso of the patient during a period of wear, the device 100 enables the patient to maintain contact with the therapy electrodes 114 for full efficacy of treatment upon delivery of a therapeutic pulse of energy. Additionally or alternatively, the tensioner 790 allows the patient to adjust the fit of the garment 110 in accordance with the patient's comfort preferences. For example, the patient may cause the tensioner 790 to loosen or tighten the garment about the torso before or after a meal, before or after engaging in physical activities (e.g., a brisk walk, running, jogging), before or after a change in body position (e.g., standing up, sitting down, or lying down), in the event of edema or swelling of the body, before or after environmental changes such as when the temperature and/or humidity shifts, or otherwise as desired by the patient.

Figure 23A:
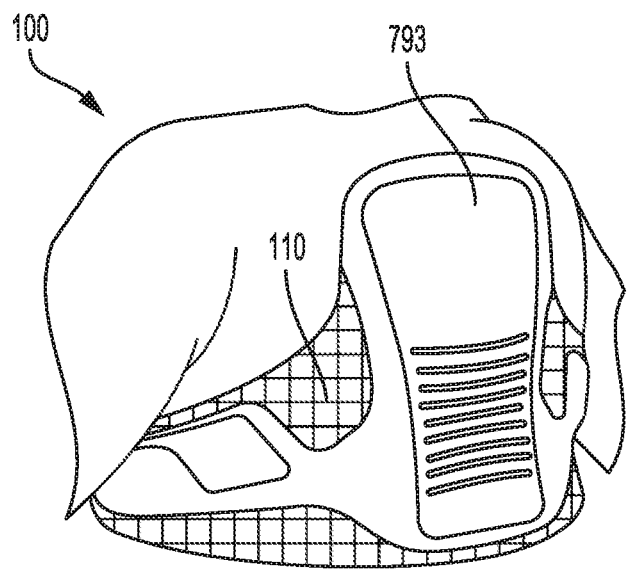
FIG. 23A depicts a rear perspective view of an embodiment of a patient-worn medical device.
Figure 23B:
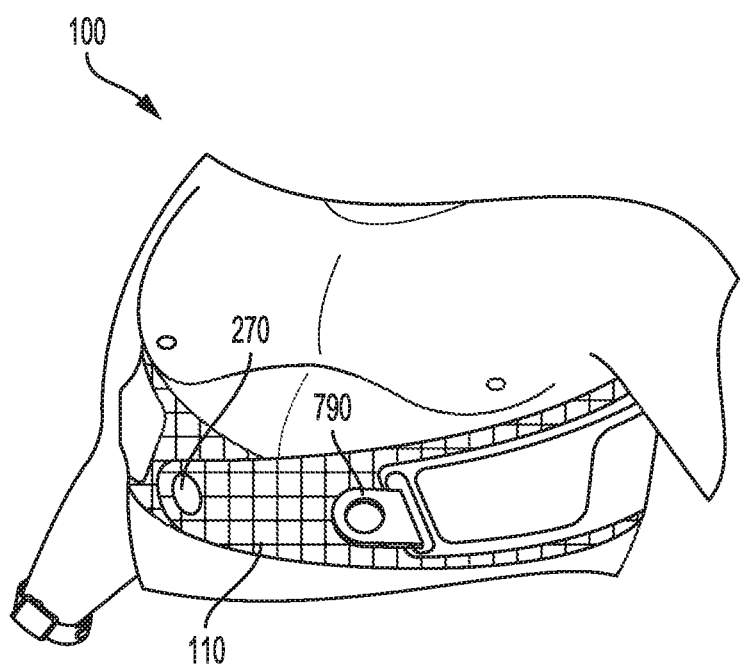
FIG. 23B depicts a front perspective view of the device of FIG. 23A.

For example, the belt-style garment 110 of FIGS. 23A and 23B includes a pre-tensioned back pad 793 that complies to the anatomy of the patient and that requires no shoulder straps for additional support. With the pre-tensioned back pad 793 placed against the patient's back, the free ends of the belt-style garment 110 are overlaid across the front of the patient's torso and secured by a fastener 270 in a first tension position. The fastener 270 could be, for example, a snap, a button, a magnet, a side release buckle, opposed hook and loop faster strips, or a buckle like any of those described with regard to FIGS. 20A to 22B. Additionally, the example garment 110 of FIGS. 23A and 23B includes a separate tensioner 790 for cinching the belt-style garment 110 more tightly than the first tension position. For example, the tensioner 790 may be a pull strap extending from one end of the belt-style garment 110 and fed through an opening in the other end of the belt style garment 110. The tensioner 790 secures to an outer surface of the garment 110 to maintain a comfortable and effective tension setting with therapy electrodes 114 and sensing electrodes 112 compressed against the torso for effective treatment and arrhythmia detection and positioned at optimal locations on the torso. In embodiments, securing the fastener 270 completes an electrical circuit and establishes an electrical communication with a disengagement sensor 260, as depicted in FIGS. 5A and 5B. In examples, the fastener 270 includes a physical indication of separation. For example, as discussed with regard to FIGS. 38A-39C, the fastener 270 may include a security tape adhered across the fastener 270 and adjacent fastened portion of the garment 110. The security tape includes a frangible break away line or delaminating layers that leave an irreversible indication of disengagement of the fastener 270.

Some implementations of tensioning elements for use with the garment 110 include compressed air tensioners. For example, FIGS. 24A through 24C show an embodiment of the garment 110 that includes a pneumatic pathway 797 welded into the garment 110 that flexes with weight changes and patient body sizes. Compressed air applies localized pressure over sensing electrodes and therapy electrodes integrated into the garment 110. The device 100 includes one or more push buttons 795 to pump air and increase localized compression. In this embodiment, as with that of FIGS. 23A and 23B, the patient adjusts the fit tightness of the garment 110 during the duration of wear without having to unfasten or remove the garment 110.

Figure 25A:
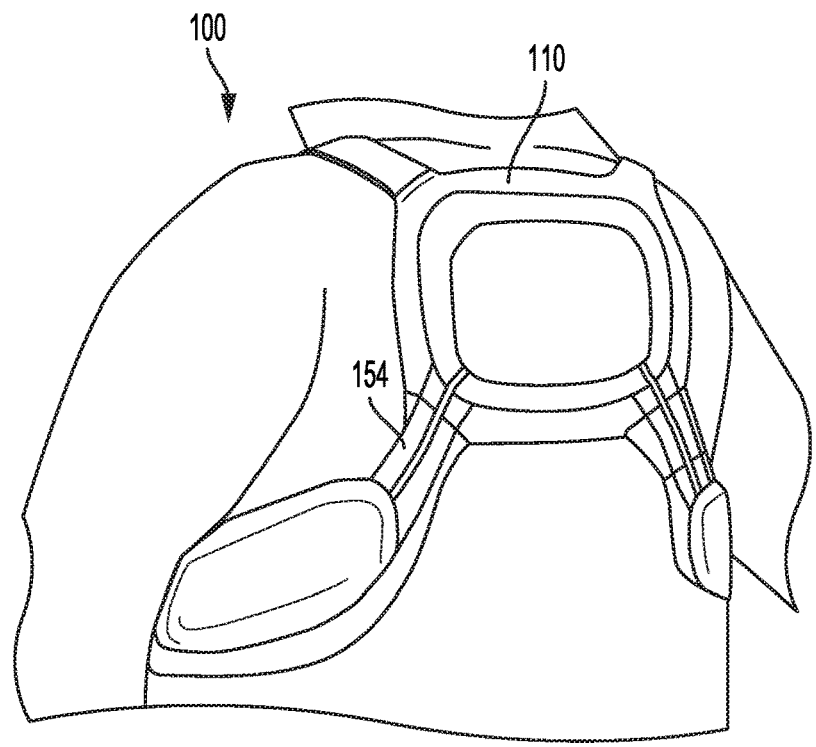
FIG. 25A depicts a rear perspective view of an embodiment of a patient-worn medical device.
Figure 25B:
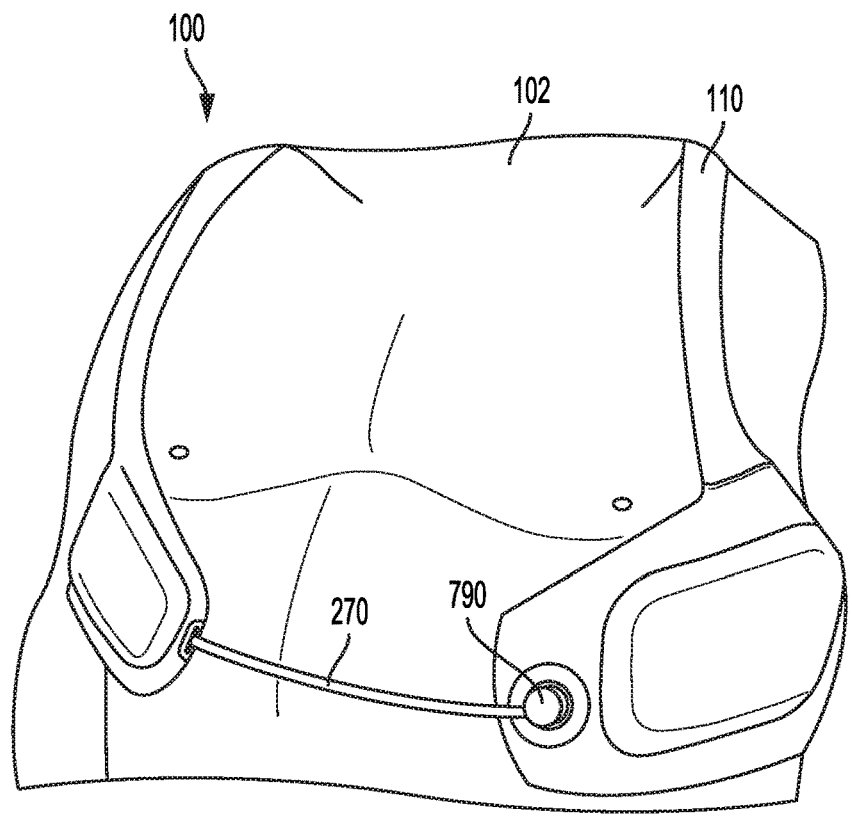
FIG. 25B depicts a front perspective view of the device of FIG. 25A.

In another example, shown in FIGS. 25A and 25B, the device 100 includes a pliable, thermoformed, breathable garment 110 with minimal surface area contact to skin. A single strap fastener 270 simplifies fastening the garment 110 and minimizes material contacting a patient's torso. A dial tensioner 790 allows the patient to tighten the strap fastener 270 without having to remove the garment 110 during the prescribed duration of wear. The dial tensioner 790 allows the strap fastener 270 to be tightened to multiple sizes to improve anatomical compliance. Tightening the strap fastener 270 positions the sensing electrodes 112 and therapy electrodes 114 in optimal locations for monitoring ECG signals and delivering effective therapeutic pulses of energy to the body 102 of the patient. In embodiments, the strap fastener 270 comprises conductive thread or wiring and connecting both ends of the strap fastener 270 to the garment 110 completes an electrical circuit and establishes an electrical communication with a disengagement sensor 260, as depicted in FIGS. 5A and 5B.

Figure 26A:
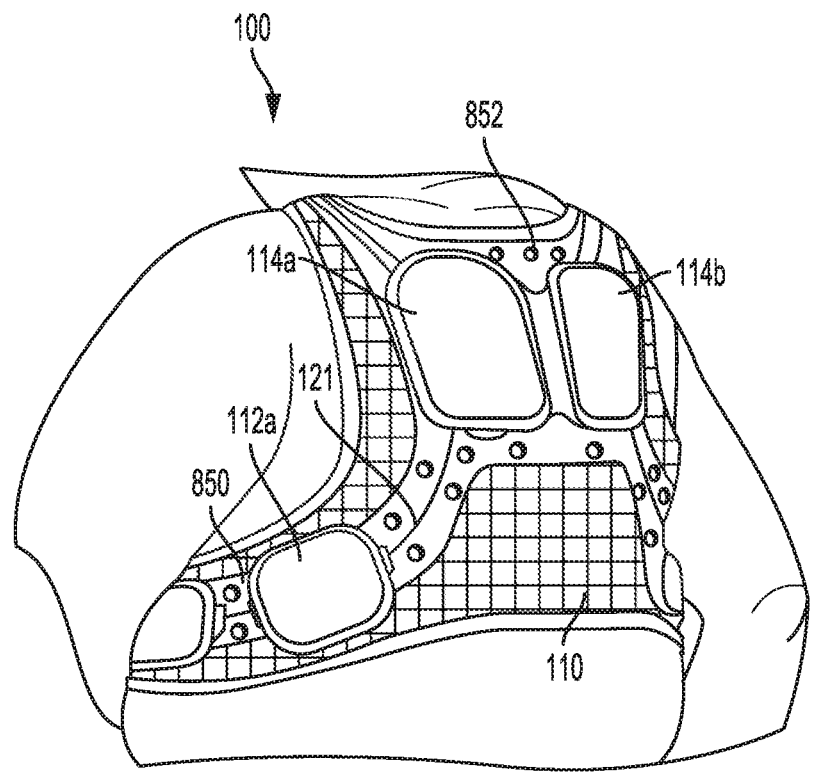
FIG. 26A depicts a rear perspective view of an embodiment of a patient-worn medical device.
Figure 26B:
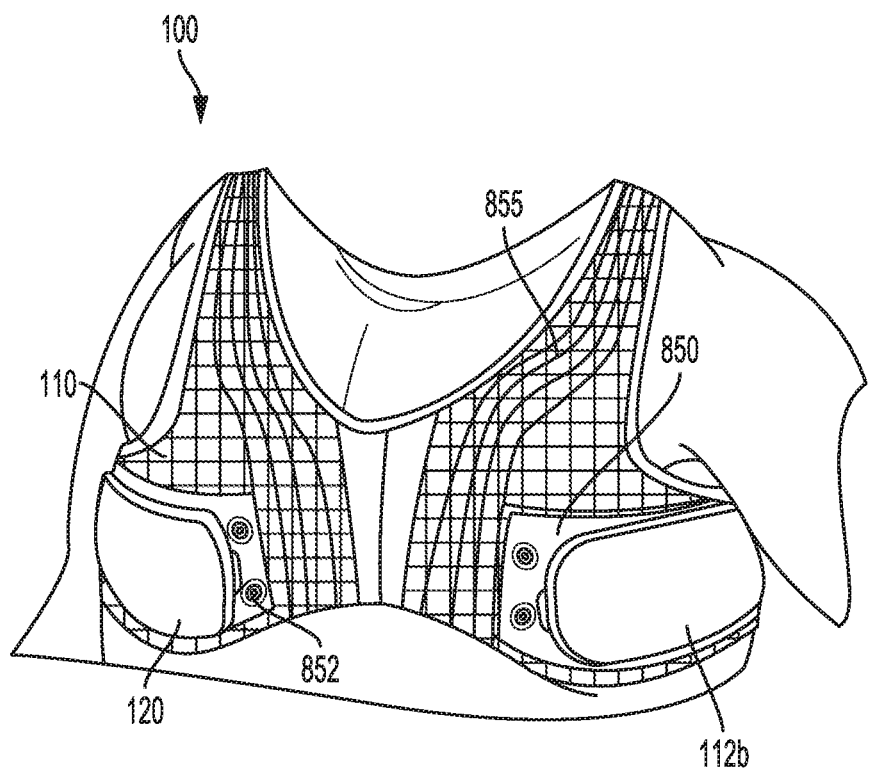
FIG. 26B depicts a front perspective view of the device of FIG. 26A.

In some embodiments, the garment 110 of the device 100 is secured about the torso of the patient and the positions of various treatment and monitoring components are adjustable apart from movement by a garment tensioner. In these examples components of the device, such as the sensing electrodes 112 and therapy electrodes 114, are removably disposed on the garment 110 at selective positions of engagement. For example, in the embodiment of FIGS. 26A and 26B, the garment 110 includes flexible tracks 850 adhered to or integrated with the garment 110 to allow custom placement of the sensing electrodes 112, therapy electrodes 114, and electronic components, such as those described with regard to the controller 120 of FIG. 2 (e.g., the one or more capacitors 403, the therapy delivery circuit 202, the processor 218, and the network interface 206). The flexible tracks 850 include a plurality of receivers 852 for receiving mating elements of the sensing electrodes 112, therapy electrodes 114, and controller 120 connected to and disposed on the flexible tracks 850. The receivers 852 electrically connect each of the sensing electrodes 112, therapy electrodes 114, and controller 120 to a wire 121 running through the flexible tracks 850. In implementations, the receivers 853 are one half of conductive snaps for mating to corresponding halves on the attached modular and moveable treatment and monitoring components.

The patient, medical provider, technician, and/or patient service representative (PSR), can adjust the location and placement of the various components along the flexible tracks 850 to maintain an optimal fit of the device 100 throughout the duration of wear. An optimal fit is one insuring customized best placement of sensing electrodes 112 for monitoring ECG signals and customized placement of therapy electrodes 114 for optimizing treatment vectors. Alternatively or additionally, an optimal fit is one providing a customized weight distribution of the device 100 that is tailored to a patient's preferences and individual anatomy. In embodiments, the device includes a flexible pleat 855 for accommodating patient anatomy and changes in size caused by weight loss, for example. In embodiments, connecting the sensing electrodes 112, therapy electrodes 114, and controller 120 to the flexible tracks 850 completes an electrical circuit and establishes an electrical communication with a disengagement sensor 260, as described with regard to the fastener of FIGS. 5A and 5B. In such examples, the disengagement sensor 260 provides an electrical signal to the processor 218 indicating the removal of one or more electronic components of the device 100 (e.g., the sensing electrodes 112, the therapy electrodes 114, the one or more capacitors 403, the therapy delivery circuit 202, the processor 218, and the network interface 206).

Figure 27A:
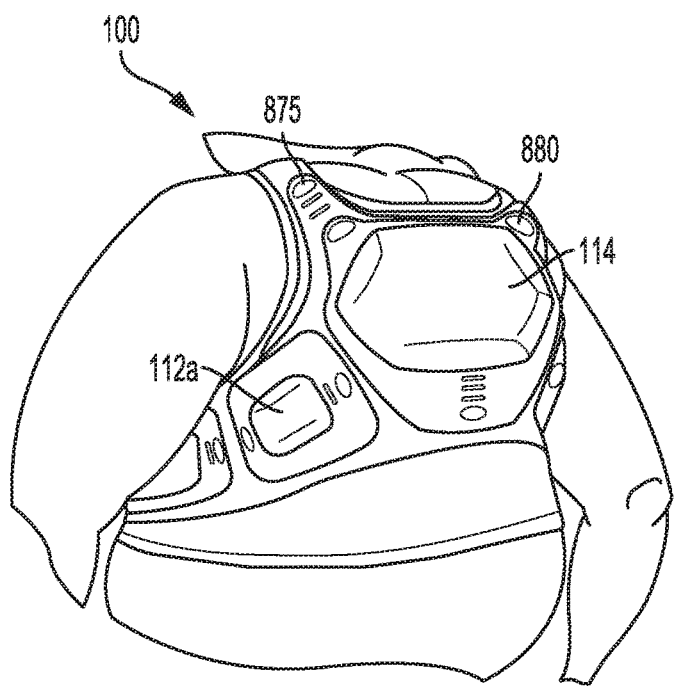
FIG. 27A depicts a rear perspective view of an embodiment of a patient-worn medical device.
Figure 27C:
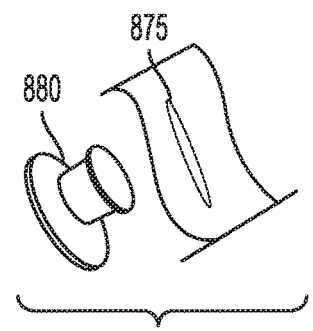
FIG. 27C depicts a magnified exploded view of a portion of the device of FIGS. 27A and 27B.
Figure 27B:
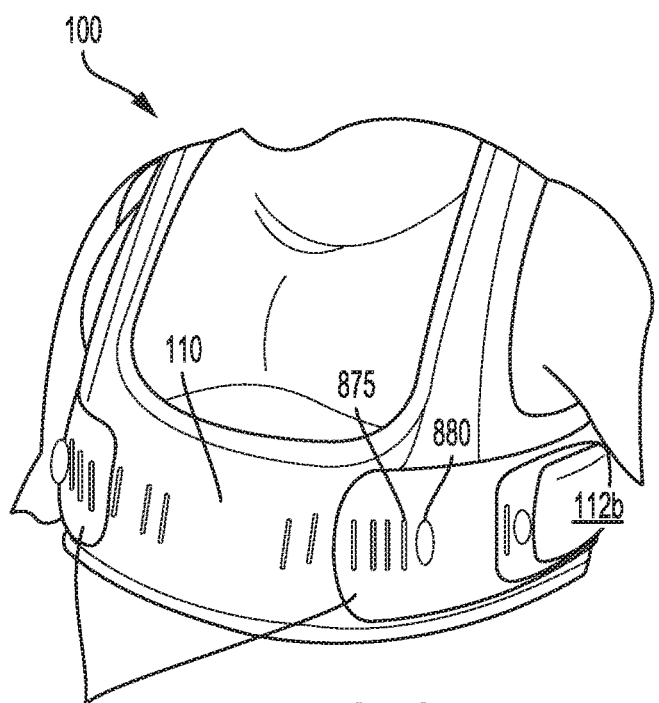
FIG. 27B depicts a front perspective view of the device of FIG. 27A.

Similarly, the embodiment of the device 100 of FIGS. 27A through 27C includes a shirt-style garment 110 donned by pulling over the patient's head. The device includes thereon one or more removably attached electronic treatment and monitoring components of the device 100 (e.g., the sensing electrodes 112, the therapy electrodes 114, the one or more capacitors 403, the therapy delivery circuit 202, the processor 218, and the network interface 206). Flexible snaps 880 on the moveable components are adhered to any of a plurality of receiving slots 875 in the garment 110 for custom placement of sensing electrodes 112, therapy electrodes 114, and heavier high voltage components, such as one or more capacitors 403. Additionally, the device 100 includes soft molded side straps 1151 that are configured to tighten the garment 110 about the torso of the patient for a customized comfortable and secure fit. The adjustable placement of the side straps 1151 allows the patient to tighten or loosen the garment 110 without having to remove the garment 110 during the prescribed duration of wear. For example, a patient prescribed a period of time of two months of continuous wear of the device 100 may lose weight in that time. Losing weight would result in a loser fit of the garment 110 and potential separation of the sensing electrodes 112 and/or therapy electrodes 114 from the patient's torso. Enabling the patient to tighten the device after three or four weeks would ensure that the sensing electrodes 112 and therapy electrodes 114 remain securely in contact with the patient's torso even in such a weight loss scenario.

The following embodiments depict additional comfort, wearability, and adjustability features that are applicable to all or any embodiments of the garment 110 of the device 100. In any of the previously presented or foregoing examples, the garment 110 includes a low skin-irritation material. In some embodiments, the garment 110 may be worn continuously by a subject for a long-term duration (e.g., duration of at least one week, at least 30 days, at least one month, at least two months, at least three months, at least six months, and at least one year) without the patient experiencing significant skin irritation. As used herein "significant skin irritation" is defined as corresponding to a skin irritation grading of one or more as set forth in Table C.1 of Annex C of American National Standard ANSI/AAMI/ISO 10993-10:2010. The skin irritation grading of one represents a weakly positive reaction usually characterized by mild erythema and/or dryness across most of the treatment site. In one implementation, significant skin irritation can be determined by testing on human subjects in accordance with the method set forth in American National Standard ANSI/AAMI/ISO 10993-10:2010, by applying sample patches of the garment material to treatment sites for up to four hours, and, in the absence of skin irritation, subsequently applying sample patches to treatment sites for up to 24 hours. The treatment sites are examined for signs of skin irritation and the responses are scored immediately after patch removal and at time intervals of (1±0.1) h to (2±1) h, (24±2) h, (48±2) h and (72±2) h after patch removal. In another implementation, a patient may wear the garment 110 as instructed for a duration of (24±2) hours, and if the patient's skin shows no reaction at the end of this duration, the garment 110 is rated as a skin irritation grading of zero.

In addition to examples of the garment 110 including low skin-irritation material, other features provide comfortable long-term wear and ease of use. For example, examples of the garment 110 includes at least one of adjustable straps, elastic straps, and disengageable straps that improve comfort during wear and the ease with which a patient dons and removes the garment 110 (e.g., reduced range of motion, easily grasped elements, low force requirements for closure).

Figure 28A:
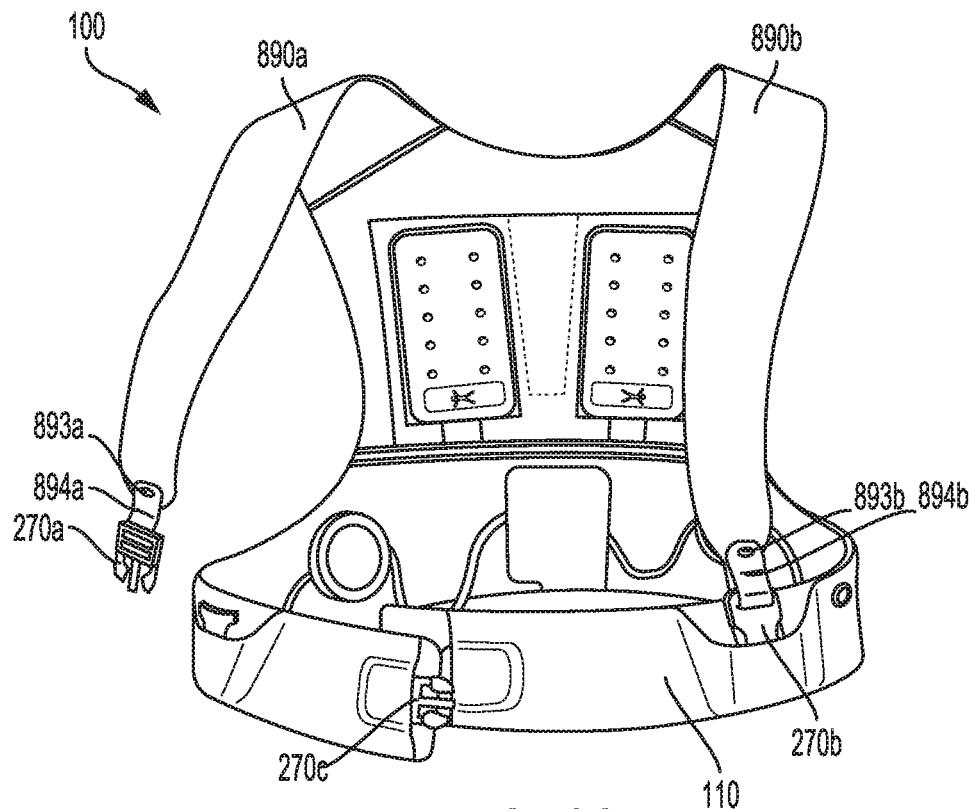
FIG. 28A depicts a front view of an embodiment of a patient-worn medical device in a partially unfastened state.
Figure 28B:
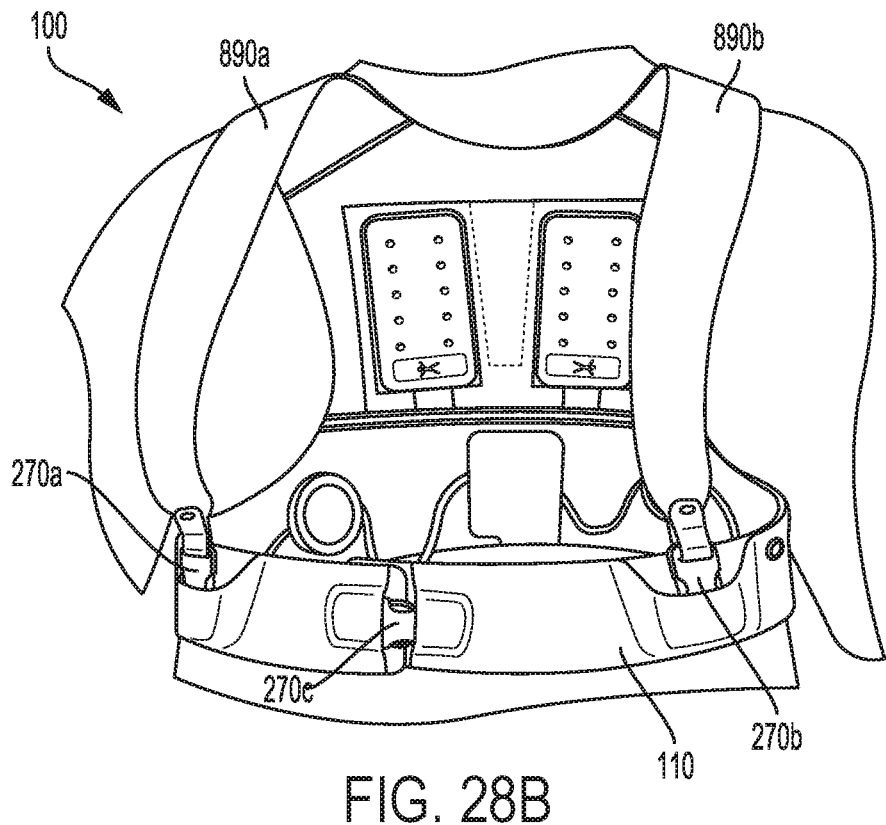
FIG. 28B depicts the device of FIG. 28A in a fastened state.
Figure 29A:
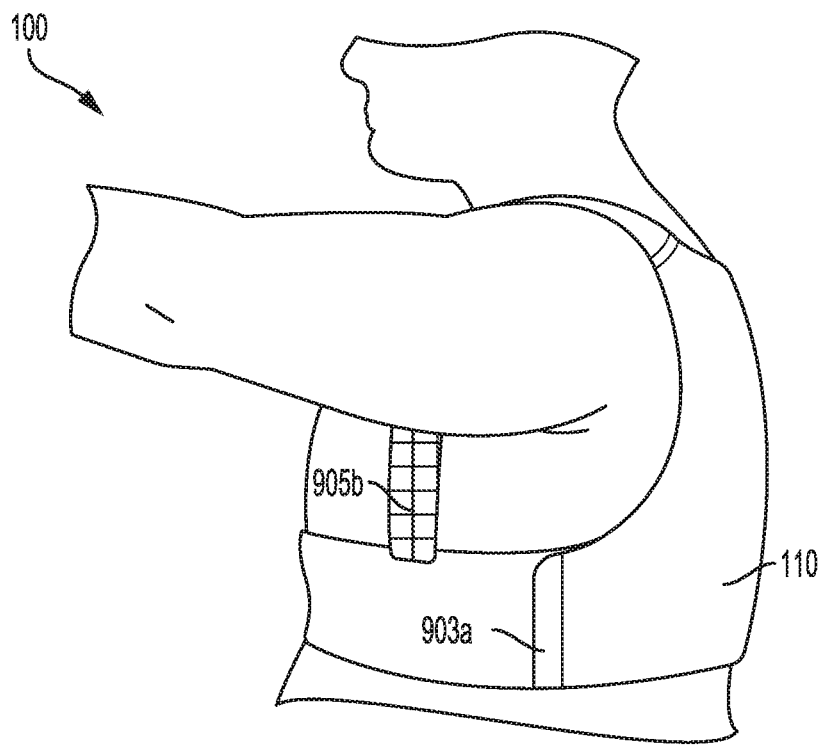
FIG. 29A depicts a side view of an embodiment of a patient-worn medical device.
Figure 29B:
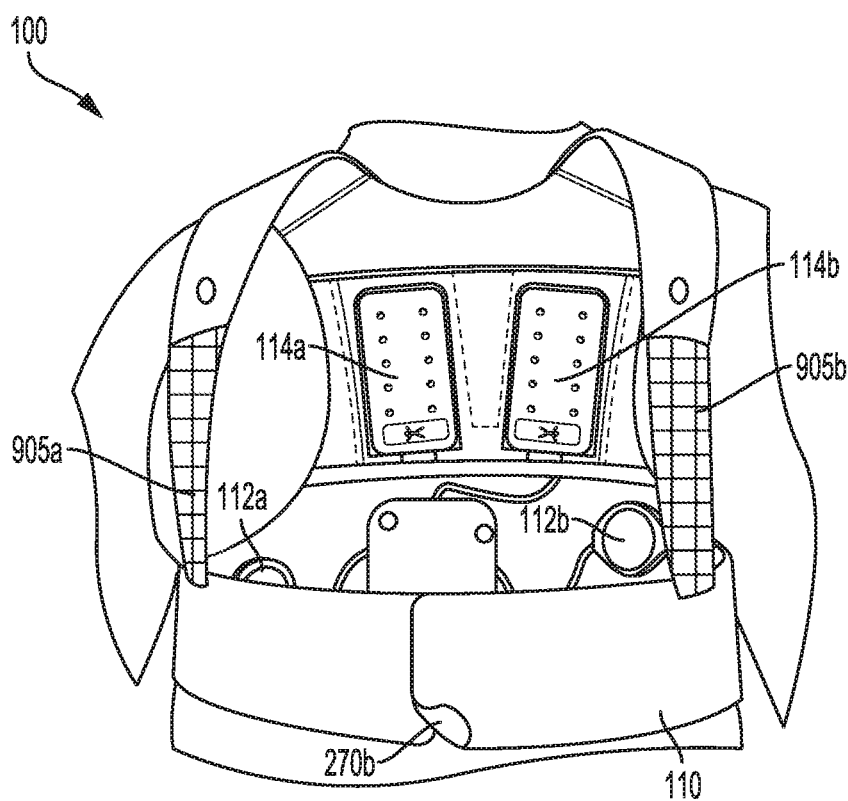
FIG. 29B depicts a front view of the device of FIG. 29A.

In the example of FIGS. 28A and 28B, the garment 110 includes a pair of detachable shoulder straps 890a, 890b that provide flexibility to a patient while attaching and removing the device 100. Studies have shown that patients with limited range of motion struggle with aligning arms through straps while dressing. The embodiment of FIGS. 28A and 28B enables a patient to lie flat on the garment 110 and connect a free-hanging, unbuckled strap 890a, 890b with a fastener 270a, 270b. The straps 890a, 890b may be adjustable in length, and, to facilitate dressing, the straps 890a, 890b may be adjusted to an extended, loose-fit position prior to bucking the fasteners 270a, 270b.

In this embodiment, one or more of the fasteners 270a, 270b on the device 100 is a side release buckle, engaged with a low force push and secured with an audible clicking noise. The end of each strap 890a, 890b is fed through an opening in a fastener 270a, 270b secured thereto. Additionally, in embodiments, the shoulder straps 890a, 890b include length adjusters for cinching the straps 890a, 890b in place on the shoulders of the patient. For example, the length adjusters may be ratchet straps, cinch straps, and pull cords and spring tensioned toggle fasteners. In the embodiment of FIGS. 28A and 28B, the free ends of the straps 890a, 890b loop through the fasteners 270a, 270b and secure to the tensioned straps 890a, 890b. The length adjusters include easily accessed buttons 893a, 893b disposed on the straps 890a, 890b and receiving slots 894a, 894b in the free ends of the straps 890a, 890b. The receiving slots 894a, 894b receive the buttons 893a, 893b and affix the length of each shoulder strap 890a, 890b to accommodate a patient's size and tension preference. Additionally, the garment 110 includes a fastener 270c located on the front of the patient's torso for securing the device 100 to the body of the patient. In embodiments, one or more of the fasteners 270a-c includes a visually detected and/or electrically connected disengagement sensor as described with regard to FIGS. 38A through 40C. For example, with the garment 110 fastened about the torso of the patient, a security tape 830 such as those of FIGS. 38A through 39C may be applied across one or more of the fasteners 270a-c to provide a visual indication of removal of some or all of the garment 110. Alternatively, one or more of the fasteners 270a-c may include a magnet for engaging a disengagement sensor 260, such as a reed switch, and completing an electrical circuit signaling engagement.

Figure 30A:
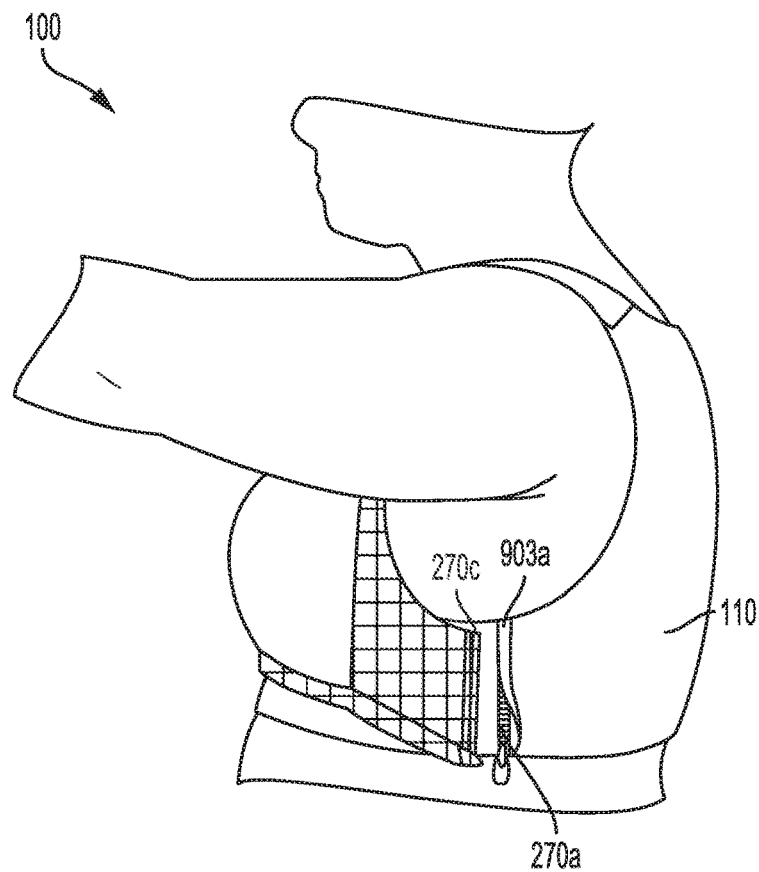
FIG. 30A depicts a side view of an embodiment of a patient-worn medical device.
Figure 30B:
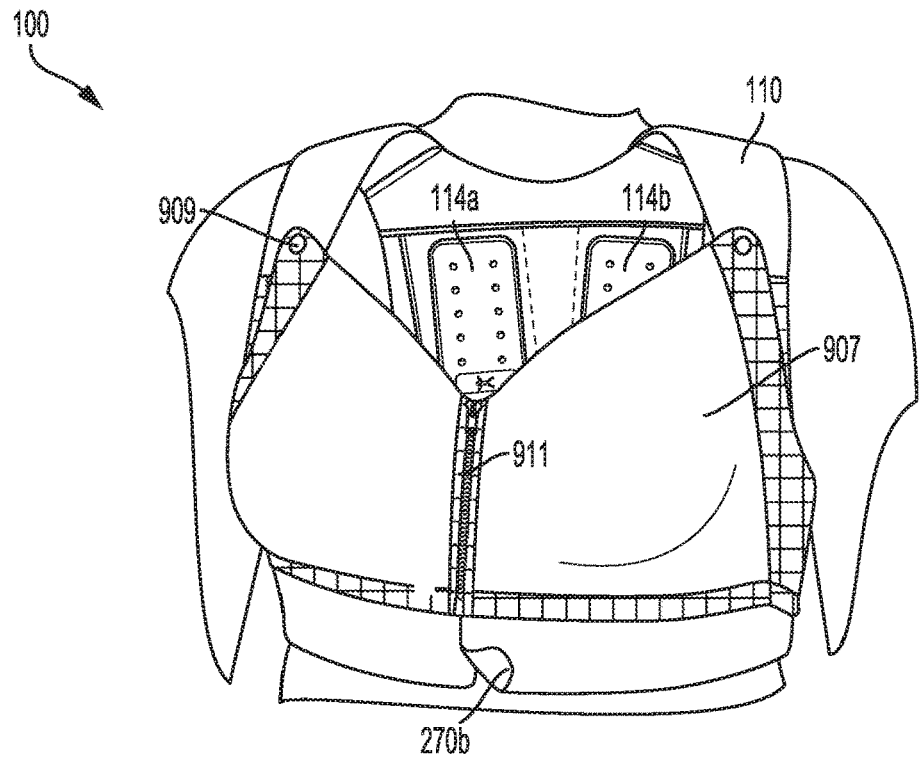
FIG. 30B depicts a front view of the device of FIG. 30A.

In another embodiment of the device 100 shown in FIGS. 29A through 30B, the garment 110 includes stretchable shoulder straps 905a, 905b for passive garment adjustment and a hidden side fastener 270a that is protected by a flap 903a to prevent snagging on clothing and scraping against skin. The garment 110 includes a front fastener 270b for adjusting and securing the device 100 about the torso of a patient. In examples, the garment 110 is configured to receive a plurality of interchangeable, anatomically conformed front torso panels. As FIGS. 30A and 30B show, in embodiments, the hidden side fastener 270a is configured for attaching an optional front panel 907, such as bra cups that reduce material stack up by eliminating the need for wearing an additional support garment. Such devices are described in U.S. application Ser. No. 15/443,856 entitled "SUPPORT GARMENT FOR A WEARABLE MEDICAL DEVICE," which was filed on Feb. 27, 2017 and is herein incorporated by reference in its entirety. In implementations, such as that shown in FIG. 30A, the front panel 907 of the garment 110 includes one half of a zipper fastener 270c that connects to the hidden side fastener 270a, which is a second half of a zipper fastener discreetly hidden under the flap 903a on the side of the garment 110. The base garment 110, therefore is configured to selectively engage with a one or more front panels 907 to provide a garment 110 tailored to the form of the patient. For example, the front panel 907 is selected from a plurality of panels having common bra cup sizes. In some examples, the straps 905a, 905b of the garment 110 include or more fasteners 909 for receiving mated fastener portions of the front panel 907. The front panel 907 may include an additional closure element 911, such as a zipper, that provides an additional option for securing or removing the garment 110 about the torso of the patient. The garment 110 thus is configurable so that a patient may optionally attach the front panel 907 either before or after securing the base garment 110 of FIGS. 28A and 28B about the torso. In embodiments, one or more of the fasteners 270a, 270b, 911, includes a visually detected and/or electrically connected disengagement sensor as described with regard to FIGS. 38A through 40C. For example, with the garment 110 fastened about the torso of the patient, a security tape 830 such as those of FIGS. 38A through 39C may be applied across the side flap 903a and/or the front fastener 270a to provide a visual indication of removal of some or all of the garment 110.

Figure 31A:
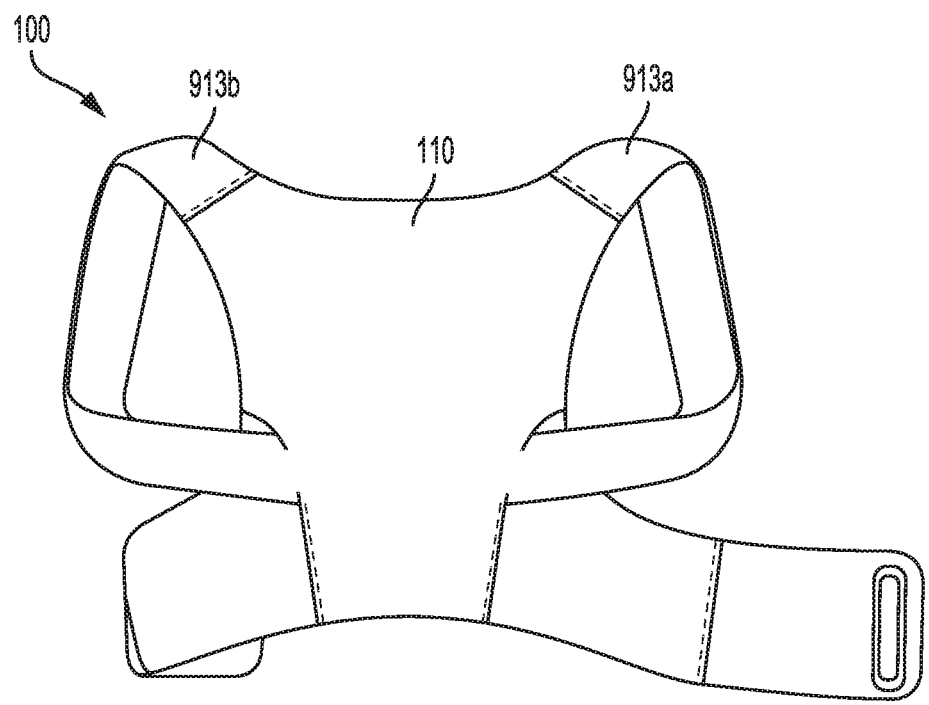
FIG. 31A depicts a rear view of an embodiment of a patient-worn medical device in an unfastened state.
Figure 31B:
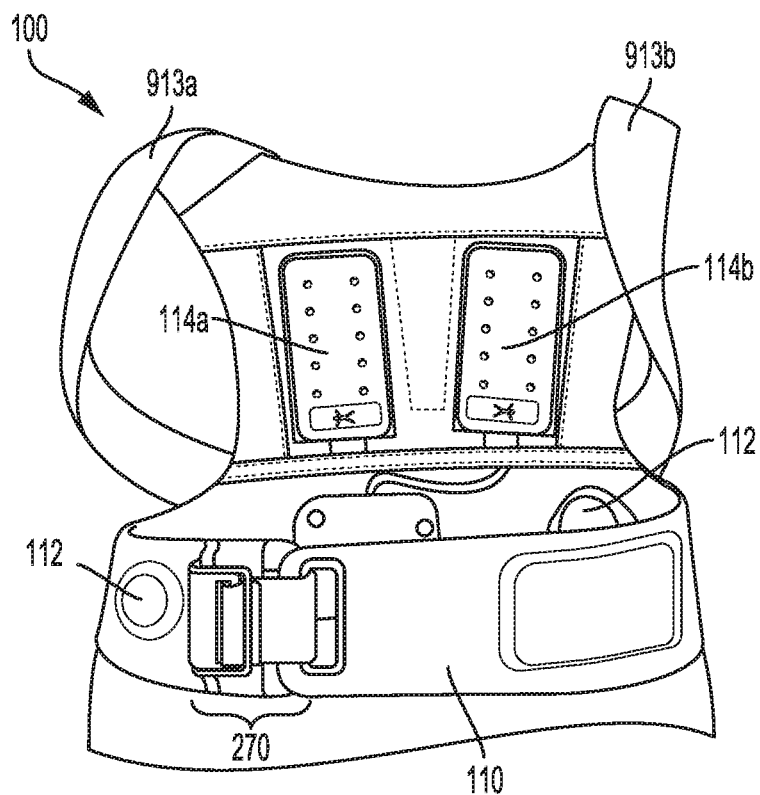
FIG. 31B depicts a front view the device of FIG. 31A in a fastened state.

In another embodiment of the device 100 shown in FIGS. 31A and 31B, the garment 110 includes a pair of shoulder straps 913a, 913b that cut under the armpits of the patient and avoid running down the front of the torso. These holster-style straps accommodate many body styles by avoiding various anatomical features particular to the patient's torso, such as a pannus or breasts. In some embodiments, the garment 110 also includes a large, off-center front fastener 270, such as the fastener described with regard to FIGS. 22A and 22B which includes a single hook closure 784 for fastening the cinch strap 782 with speed and ease as compared to closing fasteners with many smaller hooks. In embodiments, the fastener 270 provides a visible indicator and/or electrically sensed disengagement as described with regard to FIGS. 22A and 22B, and FIGS. 38A through 40C. For example, with the garment 110 fastened about the torso of the patient, a security tape 830 such as those of FIGS. 38A through 39C may be applied across the fastener 270 to provide a visual indication of disengagement of the fastener 270. Alternatively, in implementations, as described with regard to FIGS. 22A and 22B, latching the hook closure 784 of the fastener 270 to the retaining clip 792 completes an electrical circuit and establishes an electrical communication with a disengagement sensor 260, as depicted in FIGS. 5A and 5B.

Figure 32A:
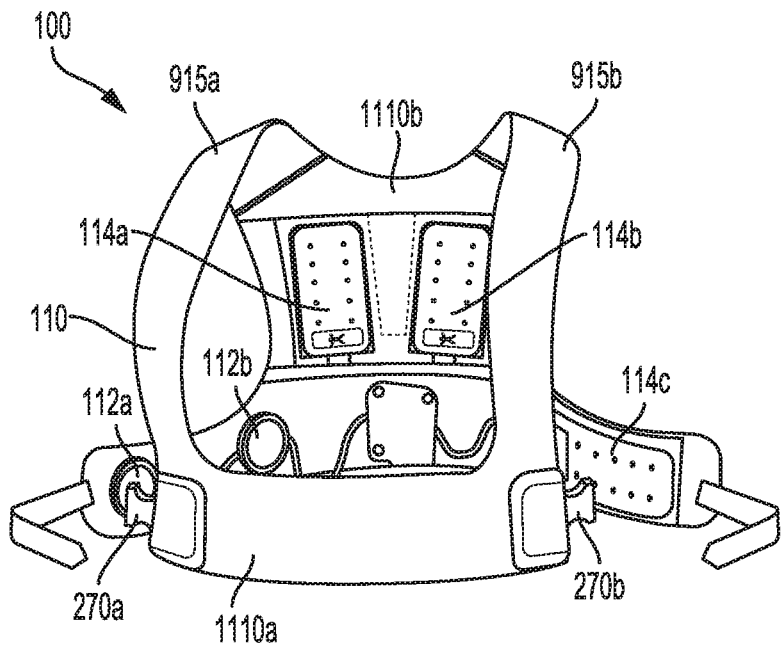
FIG. 32A depicts a front view of an embodiment of a patient-worn medical device in an unfastened state.
Figure 32B:
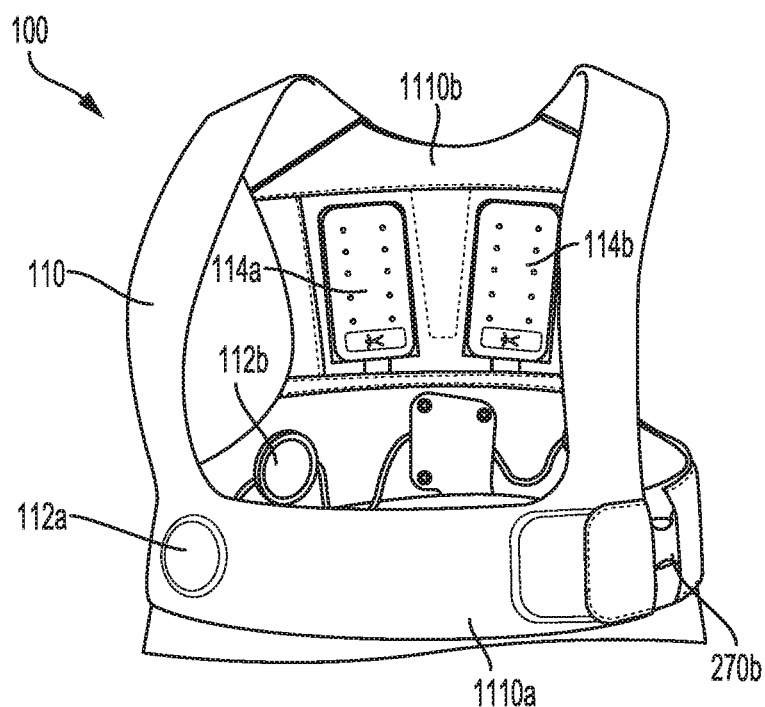
FIG. 32B depicts the device of FIG. 32A in a fastened state.

In another embodiment of the device 100 shown in FIGS. 32A and 32B, the garment 110 includes a pair of shoulder straps 915a, 915b permanently engaged and/or integrated with a front panel 1110a and a back panel 1110b of the garment 110. A patient pulls the garment 110 over the head to dress and undress the device 100. In embodiments, the front panel 1110a does not stretch and the back panel 1110b stretches to accommodate anatomical compliance. The garment 110 includes two side release buckle fasteners 270a, 270b on either side of the garment 110 to reduce irritation to the front of the patient's torso. In embodiments, the side release buckle fasteners 270a, 270b are adjustable and include one or more disengagement sensors. In embodiments, one or both of the buckle fasteners 270a, 270b includes a visually detected and/or electrically connected disengagement sensor as described with regard to FIGS. 38A through 40C. For example, with the garment 110 fastened about the torso of the patient, a security tape 830 such as those of FIGS. 38A through 39C may be applied across one or more of the fasteners 270a-c to provide a visual indication of removal of some or all of the garment 110. Alternatively, as described in FIGS. 40A through 40C, one or more of the fasteners 270a-c may include a magnet for engaging a disengagement sensor 260, such as a reed switch, and completing an electrical circuit signaling engagement.

Figure 33A:
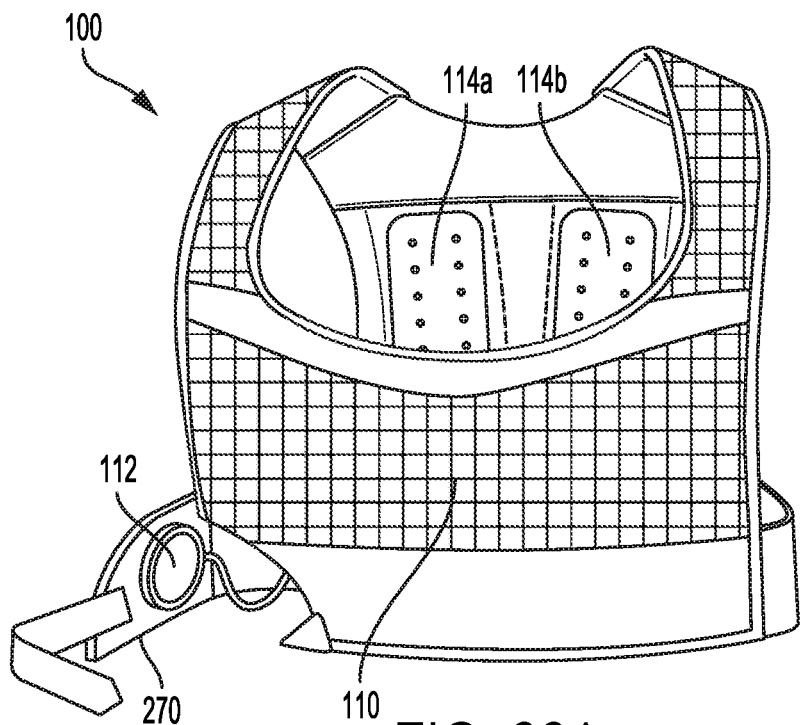
FIG. 33A depicts a front view of an embodiment of a patient-worn medical device in an unfastened state.
Figure 33B:
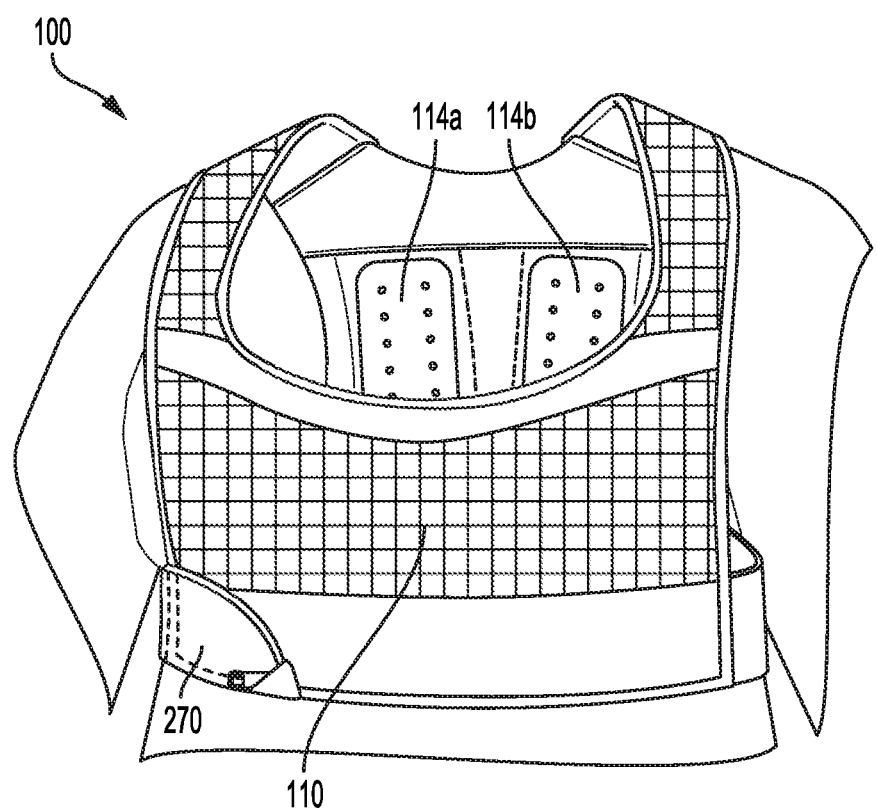
FIG. 33B depicts the device of FIG. 33A in a fastened state.

In another embodiment of the device 100 shown in FIGS. 33A and 33B, the garment 110 includes a highly-breathable chest panel and a single asymmetrically-placed fastener 270 mounted to one side to reduce irritation to the torso of the patient. In implementations, the garment 110 is configured to be permeable to transmission of moisture and water vapor from an inner layer towards an outer layer of the garment 110. In implementations of the garment 110 having a single layer, the garment is permeable to transmission of moisture and water vapor from an inner surface of the layer toward an outer surface of the layer. In implementations, the highly-breathable garment 110 has a moisture vapor transmission rate (MVTR) of between 100 g/m2/day to 250 g/m2/day. In implementations, the highly-breathable garment 110 has a moisture vapor transmission rate (MVTR) of between 250 g/m2/day to 20,000 g/m2/day. In implementations, the highly-breathable garment 110 has a moisture vapor transmission rate (MVTR) of between 20,000 g/m2/day to 50,000 g/m2/day. In implementations, the highly-breathable garment 110 is air permeable to promote ventilation through the garment 110.

The single side-mounted fastener 270 provides a monolithic, shirt-like garment such that a patient simply pulls the garment 110 over the head to dress and undress the garment 110. In embodiments, the garment 110 has no seams, further reducing irritation to the torso of the patient. In embodiments, the side-mounted fastener 270 is adjustable and enables the patient to close the fastener 270 at a comfortable tightness setting customized to personal preference. In embodiments the fastener 270 is a hook and loop strip system with one strip of hook or loop disposed on the garment and the opposing strip disposed on the fastener. In some examples, the fastener 270 may be a series of magnets, snaps, buttons for adjusting the girth of the garment 110 to a customized position.

In implementations, the single side-mounted fastener 270 includes one or more disengagement sensors. In embodiments, the fastener 270 provides a visible indicator and/or electrically sensed disengagement as described with regard to FIGS. 22A and 22B, and FIGS. 38A through 40C. For example, with the garment 110 fastened about the torso of the patient, a security tape 830 such as those of FIGS. 38A through 39C may be applied across the fastener 270 to provide a visual indication of disengagement of the fastener 270. Alternatively, in implementations, as described with regard to FIGS. 22A and 22B, mating a fastener 270, such as a conductive snap, to a receiving portion on the garment 110 completes an electrical circuit and establishes an electrical communication with a disengagement sensor 260, as depicted in FIGS. 5A and 5B.

Figure 34A:
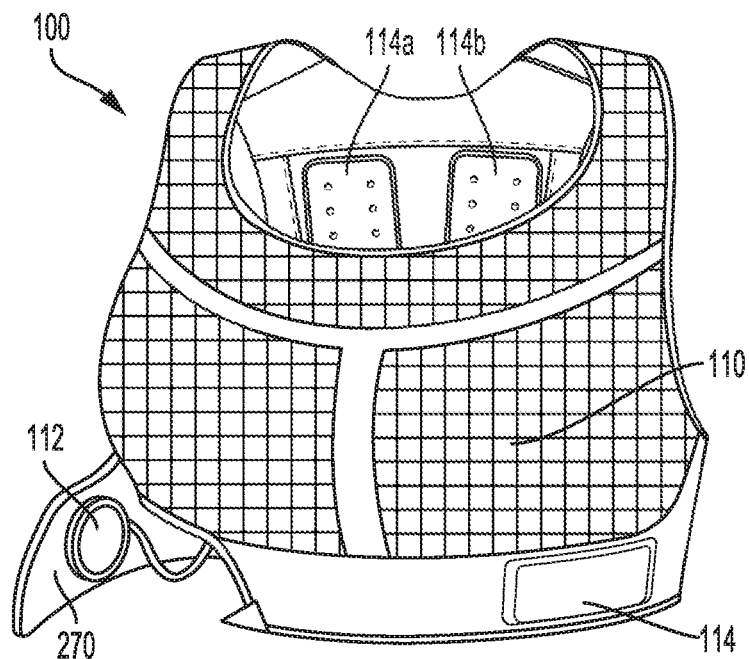
FIG. 34A depicts a front view of an embodiment of a patient-worn medical device in an unfastened state.
Figure 34B:
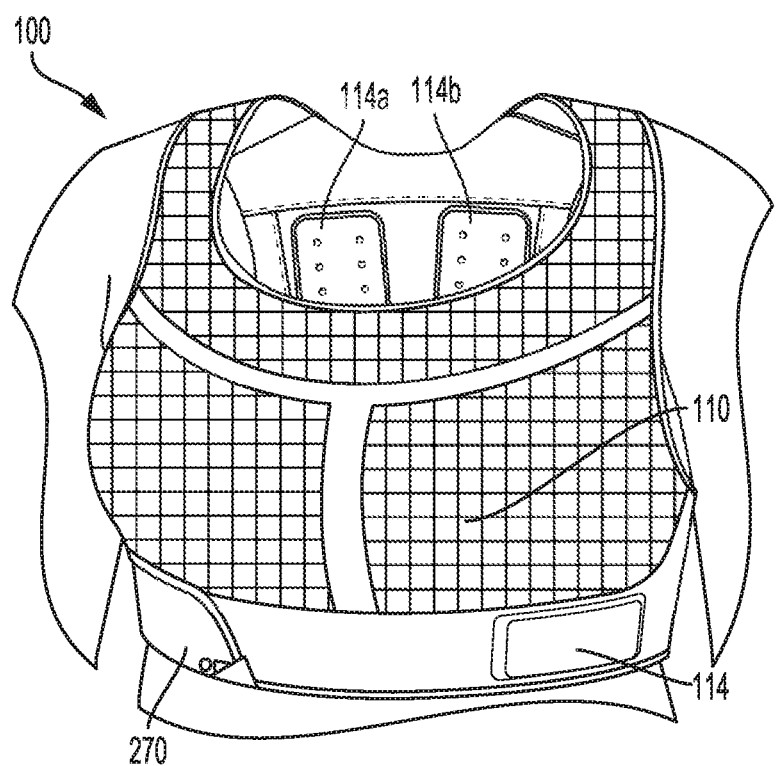
FIG. 34B depicts the device of FIG. 34A in a fastened state.

In another embodiment of the device 100 shown in FIGS. 34A and 34B, the garment 110 includes a female-specific, highly-breathable chest panel and a single asymmetrically-placed fastener 270 mounted to one side to reduce irritation to the torso of the patient. In implementations, the highly-breathable garment 110 has a moisture vapor transmission rate (MVTR) of between 100 g/m2/day to 250 g/m2/day. In implementations, the highly-breathable garment 110 has a moisture vapor transmission rate (MVTR) of between 250 g/m2/day to 20,000 g/m2/day. In implementations, the highly-breathable garment 110 has a moisture vapor transmission rate (MVTR) of between 20,000 g/m2/day to 50,000 g/m2/day. In implementations, the highly-breathable garment 110 is air permeable to promote ventilation through the garment 110. The single side mounted fastener provides a monolithic, shirt-like garment such that a patient simply pulls the garment 110 over the head to dress and undress the garment 110. In embodiments, the garment 110 has no seams, further reducing irritation to the torso of the patient. In embodiments, the side-mounted fastener 270 is adjustable and enables the patient to close the fastener 270 at a comfortable tightness setting customized to personal preference. In embodiments the fastener 270 is a hook and loop strip system with one strip of hook or loop disposed on the garment and the opposing strip disposed on the fastener. In some examples, the fastener 270 may be a series of magnets, snaps, and/or buttons for adjusting the girth of the garment 110 to a customized position. In implementations, the single side-mounted fastener 270 includes one or more disengagement sensors. In embodiments, the fastener 270 provides a visible indicator and/or electrically sensed disengagement as described with regard to FIGS. 22A and 22B, and FIGS. 38A through 40C. For example, with the garment 110 fastened about the torso of the patient, a security tape 830 such as those of FIGS. 38A through 39C may be applied across the fastener 270 to provide a visual indication of disengagement of the fastener 270. Alternatively, in implementations, as described with regard to FIGS. 22A and 22B, mating a fastener 270, such as a conductive snap, to a receiving portion on the garment 110 completes an electrical circuit and establishes an electrical communication with a disengagement sensor 260, as depicted in FIGS. 5A and 5B.

Figure 35A:
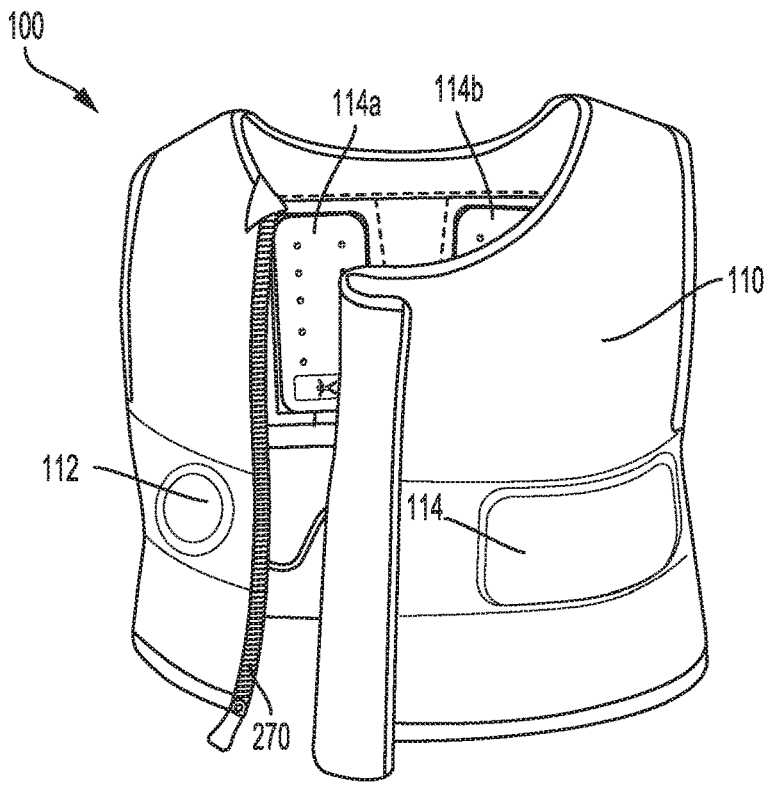
FIG. 35A depicts a front view of an embodiment of a patient-worn medical device in an unfastened state.
Figure 35B:
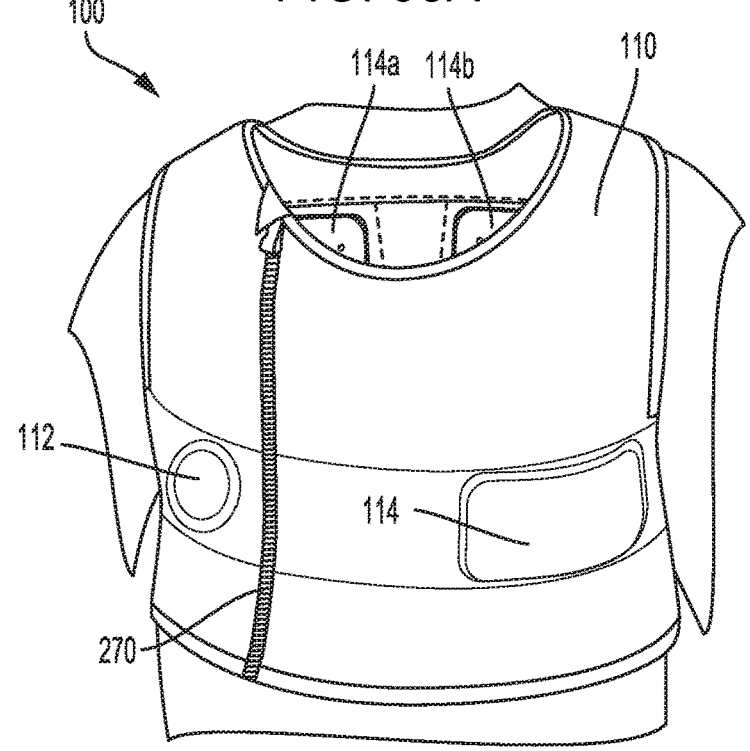
FIG. 35B depicts the device of FIG. 35A in a fastened state.

Similarly, the example of FIGS. 35A and 35B is a garment 110 having a familiar clothing style for reducing patient anxiety with engaging with the device 100. The garment 110 is jacket-like and includes an off-center full length fastener 270, such as a zipper or a plurality of buttons or snaps commonly employed with vests, shirts, and jackets. An interior mesh panel (not shown) manages and conceals components of the device 100, such as sensing electrodes 112, therapy electrodes 114 and wires 121. In implementations, the garment 110 is constructed from lightweight, breathable materials. In implementations, the breathable garment 110 has a moisture vapor transmission rate (MVTR) of between 100 g/m2/day to 250 g/m2/day. In implementations, the breathable garment 110 has a moisture vapor transmission rate (MVTR) of between 250 g/m2/day to 20,000 g/m2/day. In implementations, the breathable garment 110 has a moisture vapor transmission rate (MVTR) of between 20,000 g/m2/day to 50,000 g/m2/day. In implementations, the breathable garment 110 is air permeable to promote ventilation through the garment 110. In embodiments, the off-center full length fastener 270 provides a visible indicator and/or electrically sensed disengagement as described with regard to FIGS. 22A and 22B, and FIGS. 38A through 40C. For example, with the garment 110 fastened about the torso of the patient, one or more security tapes 830 such as those of FIGS. 38A through 39C may be applied at one or more positions across the fastener 270. For example, three security tapes 830 may be applied at the top, middle, and bottom positions of the fastener 270 to provide a visual indication of partial or complete disengagement of the fastener 270. Alternatively, in implementations, as described with regard to FIGS. 22A and 22B, mating a fastener 270, such as a conductive snap, to a receiving portion on the garment 110 completes an electrical circuit and establishes an electrical communication with a disengagement sensor 260, as depicted in FIGS. 5A and 5B.

Figure 36A:
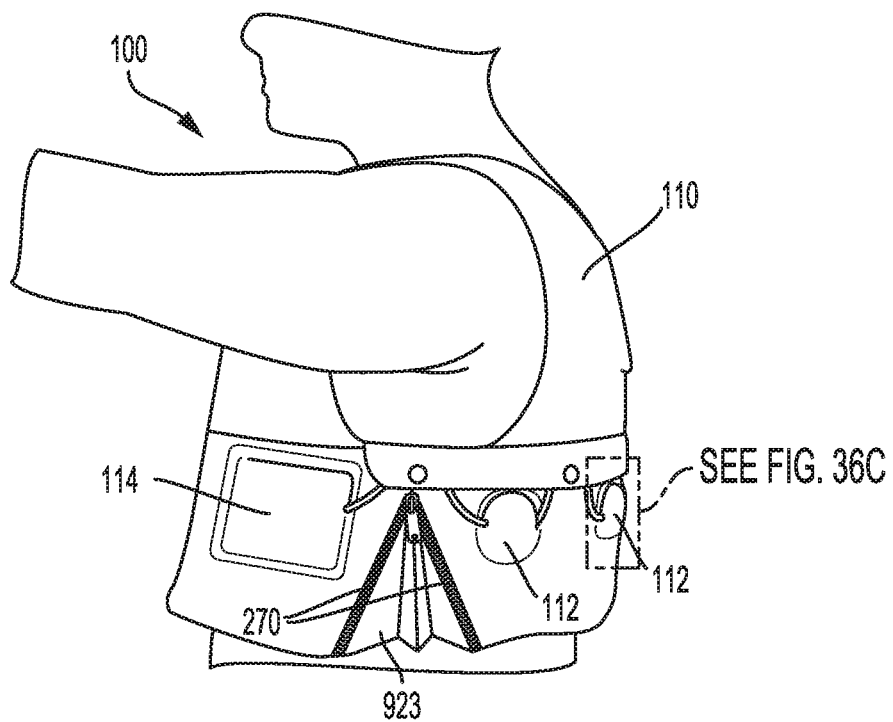
FIG. 36A depicts a side view of an embodiment of a patient-worn medical device.
Figure 36B:
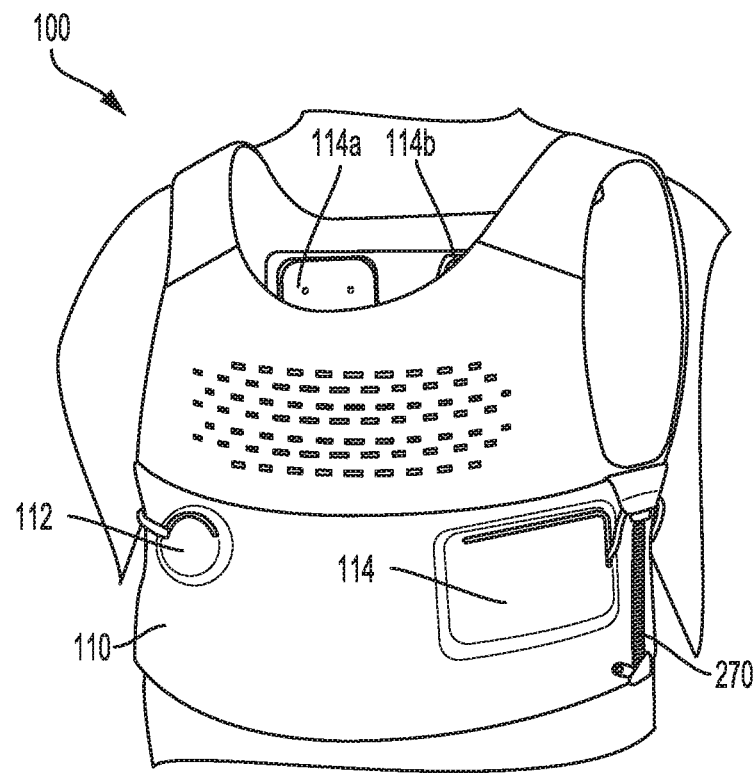
FIG. 36B depicts a front perspective view of the device of FIG. 36A.
Figure 36C:
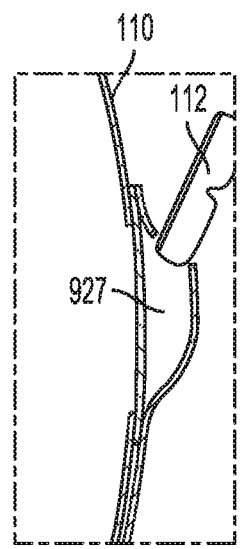
FIG. 36C depicts a magnified exploded view of a portion of the device of FIGS. 36A and 36B.

In yet another example, FIGS. 36A through 36C depict a garment 110 having a common and familiar-feeling clothing style for reducing patient anxiety with engaging with the device 100. The shirt-like embodiment of the garment 110 shown in FIGS. 36A through 36C defines a continuous loop designed for a patient to pull the garment 110 over the head to slip on and off the torso. The garment 110 includes one or more expandable (e.g., pleated and extendable) side panels 923 that provide garment compression in a closed state and, in an open state, loosens the garment for dressing and undressing. The one or more expandable side panels 923 are closed and opened with a fastener 270, such as a zipper, running the length of the expandable side panel 923. In implementations, the fastener 270 includes a disengagement sensor.

In embodiments, the fastener 270 provides a visible indicator and/or electrically sensed disengagement as described with regard to FIGS. 22A and 22B, and FIGS. 38A through 40C. For example, with the garment 110 fastened about the torso of the patient, one or more security tapes 830 such as those of FIGS. 38A through 39C may be applied at one or more positions across the fastener 270. For example, three security tapes 830 may be applied at the top, middle, and bottom positions of the fastener 270 to provide a visual indication of disengagement of partial or complete disengagement of the fastener 270. Alternatively, in implementations, as described with regard to FIGS. 22A and 22B, the fastener 270 includes one or more conductive snaps or buttons for closing the one or more accordion side panels 923. Mating a fastener 270, such as a conductive snap, to close the one or more accordion side panels 923 of the garment 110 completes an electrical circuit and establishes an electrical communication with a disengagement sensor 260, as depicted in FIGS. 5A and 5B.

Additionally, the garment 110 of FIGS. 36A through 36C includes thermoformed and laser-cut receptacles 927 that receive one or more of the sensing electrodes 112, therapy electrodes 114 and elements of the controller 120 (e.g., the sensing electrodes 112, the therapy electrodes 114, the one or more capacitors 403, the therapy delivery circuit 202, the processor 218, and the network interface 206) on the outside of the garment 110. In implementations, the garment 110 is constructed from lightweight, breathable materials. In implementations, the breathable garment 110 has a moisture vapor transmission rate (MVTR) of between 100 g/m2/day to 250 g/m2/day. In implementations, the breathable garment 110 has a moisture vapor transmission rate (MVTR) of between 250 g/m2/day to 20,000 g/m2/day. In implementations, the breathable garment 110 has a moisture vapor transmission rate (MVTR) of between 20,000 g/m2/day to 50,000 g/m2/day. In implementations, the breathable garment 110 is air permeable to promote ventilation through the garment 110.

Figure 37A:
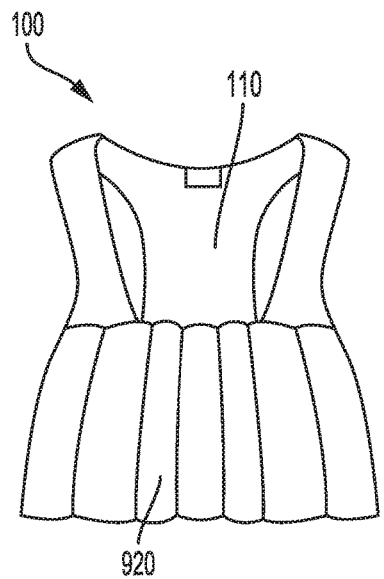
FIG. 37A depicts a front view of an embodiment of a patient-worn medical device.
Figure 37B:
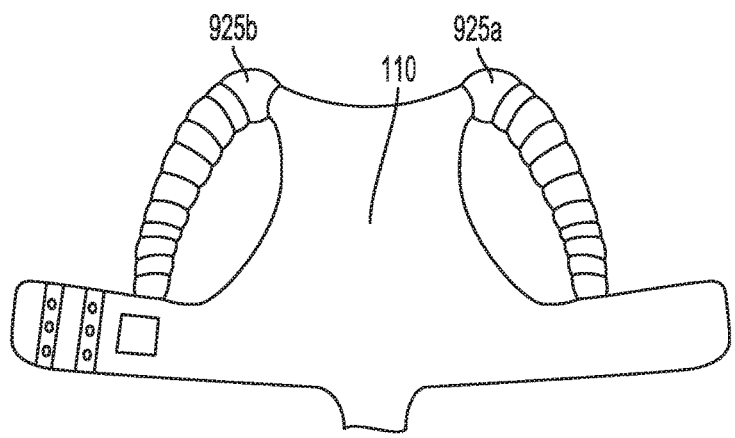
FIG. 37B depicts a back view of a patient-worn medical device in an unfastened state.
Figure 37C:
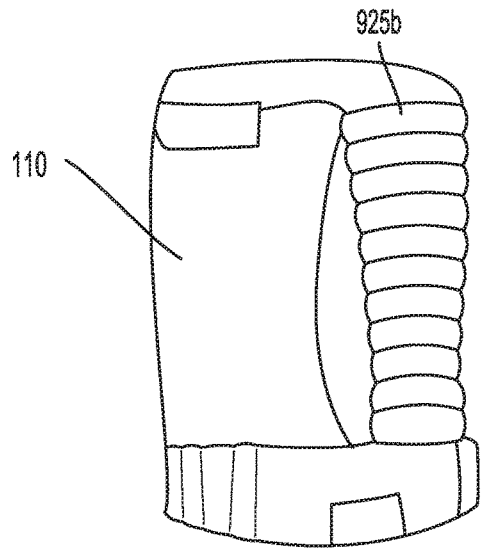
FIG. 37C depicts a portion of the device of FIG. 37B.

In another embodiment of the garment 110 shown in FIGS. 37A through 37C, a pleated torso panel 920 and/or pleated straps 925a, 925b passively adjust to anatomy while a patient is standing, or if the patient gains or loses weight. The pleated body 920 of the garment 110 allows a patient's weight to be distributed through pleats rather than push down between a waistband of an article of clothing and the bottom of garment 110. This also prevents the garment 110 from riding up the torso of the patient. The pleated torso panel 920 of the garment 110 eliminates the need for fasteners. The pleated straps 925*a*, 925*b* on the garment 110 prevent slippage and preventing straps from cutting into the patient's shoulders. In embodiments, the pleating is accordion-style and sewn to a loose, less-taut elastic so that the pleating expands and contracts during arm movements like flexing or hunching. In some implementations, the garment 110 includes both a pleated torso panel 920 and pleated straps 925*a*, 925*b*. In some implementations, the garment 110 comprises at least one of pleated straps 925*a*, 925*b* or a pleated torso panel 920. The pleated body 920 and pleated straps 925*a*, 925*b* of FIGS. 37A through 37C may be applied to any of the foregoing described implementations of the garment 110 having fasteners in various positions on the straps and body of the garment 110.

Although the subject matter contained herein has been described in detail for the purpose of illustration, it is to be understood that such detail is solely for that purpose and that the present disclosure is not limited to the disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

Other examples are within the scope and spirit of the description and claims. Additionally, certain functions described above can be implemented using software, hardware, firmware, hardwiring, or combinations of any of these. Features implementing functions can also be physically located at various positions, including being distributed such that portions of functions are implemented at different physical locations.

What is claimed is:

1. A wearable cardiac monitoring and treatment device, comprising:
   a garment configured to be worn continuously about a torso of a patient for an extended period of time;
   a plurality of electrocardiogram (ECG) sensing electrodes supported by the garment and configured to monitor an ECG signal of the patient;
   a plurality of therapy electrodes supported by the garment and configured to provide one or more therapeutic pulses to the patient;
   a fastener configured to secure the garment about the torso of the patient for at least a prescribed duration, wherein the fastener comprises a breakaway element comprising a color-changing element that permanently changes color in response to being stretched beyond a predetermined limit;
   a disengagement sensor configured to provide an indication of a disengagement of the fastener prior to expiration of at least the prescribed duration in which the garment is no longer secured about the torso of the patient;
   a therapy delivery circuit electrically configured to deliver the one or more therapeutic pulses to the patient through the plurality of therapy electrodes; and
   a controller electrically coupled to the plurality of ECG sensing electrodes and the therapy delivery circuit, the controller configured to
      detect an arrhythmia condition of the patient based on the monitored ECG signal of the patient, and
      cause the therapy delivery circuit to deliver the one or more therapeutic pulses to the patient on detecting the arrhythmia condition.

2. The device of claim 1, wherein the disengagement sensor is electrically coupled to the controller and configured to
   provide the indication of the disengagement of the fastener prior to the expiration of at least the prescribed duration by generating a signal in response to mechanical disengagement of the fastener.

3. The device of claim 2, wherein the controller is configured to receive the signal generated in response to the mechanical disengagement and provide an alert.

4. The device of claim 3, further comprising a conductive thread integrated into the garment and configured for coupling to at least one of the controller, the plurality of ECG sensing electrodes, the plurality of therapy electrodes, or the disengagement sensor.

5. The device of claim 3, wherein the controller is further configured to store a flag indicative of the mechanical disengagement in a memory of the device for later retrieval.

6. The device of claim 3, wherein the alert comprises a notification sent to a remote server.

7. The device of claim 3, further comprising at least one user interface communicatively coupled to the controller, wherein the alert comprises a notification that is at least one of displayed or transmitted at a user interface.

8. The device of claim 3, wherein the alert comprises at least one of a tactile alert, an audible alert, or a visual alert.

9. The device of claim 1, wherein the garment comprises at least one of a vest worn about the torso of the patient, a wrap-around garment, or a one-shoulder garment configured to be worn about one shoulder and wrap around an upper torso of the patient.

10. The device of claim 1, further comprising one or more capacitors wherein
    the one or more capacitors are coupled to the therapy delivery circuit, and
    the therapy delivery circuit is configured to deliver a discharge of energy from the one or more capacitors.

11. The device of claim 1, wherein the controller comprises a plurality of modules including one or more capacitors, the therapy delivery circuit, a processor, a user interface, and a network interface, and the plurality of modules are distributed about and secured within the garment.

12. The device of claim 1, wherein the disengagement sensor comprises at least one of a capacitive sensor, a hall effect sensor, a reed switch, or an optical proximity sensor.

13. A wearable cardiac monitoring and treatment device, comprising:
    a garment configured to be worn continuously about a torso of a patient for an extended period of time;
    a fastener configured to secure the garment about the torso of the patient for at least a prescribed duration of wear, wherein the fastener comprises a breakaway element comprising a color-changing element that permanently changes color in response to being stretched beyond a predetermined limit;
    a plurality of electrocardiogram (ECG) sensing electrodes supported by the garment and configured to monitor an ECG signal of the patient;

a plurality of therapy electrodes supported by the garment and configured to provide one or more therapeutic pulses to the patient;

a therapy delivery circuit electrically configured to deliver the one or more therapeutic pulses to the patient through the plurality of therapy electrodes;

one or more sensors supported by the garment, the one or more sensors configured to monitor one or more physiological signals of the patient; and a controller electrically coupled to the plurality of ECG sensing electrodes and the therapy delivery circuit, the controller configured to detect an arrhythmia condition of the patient based on the monitored ECG signal of the patient, cause the therapy delivery circuit to deliver the one or more therapeutic pulses to the patient on detecting the arrhythmia condition, detect that the garment is no longer worn about the torso of the patient prior to expiration of at least the prescribed duration of wear, and issue a notification that the garment is no longer worn about the torso of the patient.

14. The device of claim 13, wherein detecting that the garment is no longer worn about the torso comprises detecting a loss of signal for at least a threshold period of time from at least one of one or more of the plurality of ECG sensing electrodes or one or more of the one or more sensors prior to the expiration of at least the prescribed duration of wear.

15. The device of claim 14, wherein the detection of the loss of signal is preceded by continuous monitoring of the ECG signal without detecting an arrhythmia condition.

16. The device of claim 14, wherein the controller issues the notification that the garment is no longer worn about the torso of the patient in response to the detection of the loss of signal for at least the threshold period of time.

17. The device of claim 16, wherein the threshold period of time comprises a duration ranging from 1 to 5 minutes.

18. The device of claim 16, wherein the threshold period of time comprises 1-30 seconds, such that the controller is configured to immediately provide the notification upon detecting the loss of signal.

19. The device of claim 13, wherein the notification comprises at least one of an audible, visible, or haptic alert provided to at least one of the patient and a remote caregiver.

20. The device of claim 13, further comprising
a disengagement sensor configured to provide an indication of a disengagement of the fastener prior to the expiration of at least the prescribed duration of wear in which the garment is no longer secured about the torso of the patient.

* * * * *

UNITED STATES PATENT AND TRADEMARK OFFICE
CERTIFICATE OF CORRECTION

PATENT NO. : 11,160,972 B2
APPLICATION NO. : 16/369118
DATED : November 2, 2021
INVENTOR(S) : Gary A. Freeman et al.

It is certified that error appears in the above-identified patent and that said Letters Patent is hereby corrected as shown below:

On the Title Page

Abstract, Line 6, delete "to" after "sensor"

In the Specification

Column 3, Lines 49-50, delete "100 g/m2/day to 250 g/m2/day." and insert --100 $g/m^2$/day to 250 $g/m^2$/day.--
Column 3, Lines 51-52, delete "250 g/m2/day to 20,000 g/m2/day." and insert --250 $g/m^2$/day to 20,000 $g/m^2$/day.--
Column 3, Line 54, delete "20,000 g/m2/day to 50,000 g/m2/day." and insert --20,000 $g/m^2$/day to 50,000 $g/m^2$/day.--
Column 4, Line 35, delete "include" and insert --includes--
Column 4, Line 58, delete "a ECG" and insert --an ECG--
Column 5, Line 25, delete "defines" and insert --define--
Column 6, Lines 50-51, delete "100 g/m2/day to 250 g/m2/day." and insert --100 $g/m^2$/day to 250 $g/m^2$/day.--
Column 6, Lines 52-53, delete "250 g/m2/day to 20,000 g/m2/day." and insert --250 $g/m^2$/day to 20,000 $g/m^2$/day.--
Column 6, Line 55, delete "20,000 g/m2/day to 50,000 g/m2/day." and insert --20,000 $g/m^2$/day to 50,000 $g/m^2$/day.--
Column 7, Line 60, delete "pethysmographic" and insert --plethysmographic--
Column 10, Line 59, delete "an fastened" and insert --a fastened--
Column 10, Line 66, delete "an fastened" and insert --a fastened--
Column 11, Line 5, delete "an fastened" and insert --a fastened--
Column 11, Line 13, delete "device" and insert --device.--
Column 16, Line 61, delete "THERAPUETIC" and insert --THERAPEUTIC--
Column 18, Line 12, delete "link," and insert --link.--
Column 24, Line 32, delete "112A" and insert --112a--
Column 24, Line 36, delete "112A" and insert --112a--

Signed and Sealed this
Twentieth Day of September, 2022

*Katherine Kelly Vidal*
*Director of the United States Patent and Trademark Office*

Column 27, Line 61, delete "in in" and insert --in--
Column 28, Line 35, delete "the" after "appreciated that"
Column 30, Line 7, delete "direction" and insert --direction.--
Column 30, Line 11, delete "direction" and insert --direction.--
Column 33, Line 15, delete "the" after "For example,"
Column 34, Line 20, delete "quick-start" and insert --quick start--
Column 37, Line 55, delete "112" and insert --112.--
Column 37, Line 62, delete "an diameter" and insert --a diameter--
Column 40, Line 19, delete "1.0 lb-8.0 lbf" and insert --1.0 lbf-8.0 lbf--
Column 41, Line 27, delete "a"
Column 42, Line 31, delete "pethysmographic," and insert --plethysmographic,--
Column 43, Line 16, delete "a" after "includes"
Column 45, Line 56, delete "portion" and insert --portions--
Column 49, Line 11, delete "a" after "with"
Column 50, Line 30, delete "100 g/m2/day to 250 g/m2/day." and insert --100 $g/m^2/day$ to 250 $g/m^2/day$.--
Column 50, Line 32-33, delete "250 g/m2/day to 20,000 g/m2/day." and insert --250 $g/m^2/day$ to 20,000 $g/m^2/day$.--
Column 50, Lines 35-36, delete "20,000 g/m2/day to 50,000 g/m2/day." and insert --20,000 $g/m^2/day$ to 50,000 $g/m^2/day$.--
Column 51, Line 7, delete "100 g/m2/day to 250 g/m2/day." and insert --100 $g/m^2/day$ to 250 $g/m^2/day$.--
Column 51, Lines 9-10, delete "250 g/m2/day to 20,000 g/m2/day." and insert --250 $g/m^2/day$ to 20,000 $g/m^2/day$.--
Column 51, Lines 12-13, delete "20,000 g/m2/day to 50,000 g/m2/day." and insert --20,000 $g/m^2/day$ to 50,000 $g/m^2/day$.--
Column 51, Line 55, delete "100 g/m2/day to 250 g/m2/day." and insert --100 $g/m^2/day$ to 250 $g/m^2/day$.--
Column 51, Lines 57-58, delete "250 g/m2/day to 20,000 g/m2/day." and insert --250 $g/m^2/day$ to 20,000 $g/m^2/day$.--
Column 51, Line 60, delete "20,000 g/m2/day to 50,000 g/m2/day." and insert --20,000 $g/m^2/day$ to 50,000 $g/m^2/day$.--
Column 52, Lines 56-57, delete "100 g/m2/day to 250 g/m2/day." and insert --100 $g/m^2/day$ to 250 $g/m^2/day$.--
Column 52, Line 59, delete "250 g/m2/day to 20,000 g/m2/day." and insert --250 $g/m^2/day$ to 20,000 $g/m^2/day$.--
Column 52, Lines 61-62, delete "20,000 g/m2/day to 50,000 g/m2/day." and insert --20,000 $g/m^2/day$ to 50,000 $g/m^2/day$.--